United States Patent [19]
Bitter

[11] Patent Number: 6,048,693
[45] Date of Patent: Apr. 11, 2000

[54] PHENOTYPIC ASSAYS OF CYCLIN/CYCLIN-DEPENDENT KINASE FUNCTION

[75] Inventor: Grant A. Bitter, Agoura, Calif.

[73] Assignee: BitTech, Inc., Westlake Village, Calif.

[21] Appl. No.: 08/951,923

[22] Filed: Oct. 16, 1997

Related U.S. Application Data

[60] Provisional application No. 60/029,127, Oct. 16, 1996, and provisional application No. 60/031,968, Nov. 27, 1996.

[51] Int. Cl.$^7$ .............................. C12Q 1/68; C12N 15/63; C07H 21/02; C12P 21/00
[52] U.S. Cl. ......................... 435/6; 435/69.1; 435/172.3; 435/240.2; 435/320.1; 536/23.1; 536/24.3; 536/24.31; 530/350; 436/501
[58] Field of Search .......................... 435/6, 69.1, 172.3, 435/240.2, 320.1; 536/23.1, 24.3, 24.31; 530/350; 436/501

[56] References Cited

U.S. PATENT DOCUMENTS

| | | | |
|---|---|---|---|
| 5,283,173 | 2/1994 | Fields et al. ................................. | 435/6 |
| 5,443,962 | 8/1995 | Draetta et al. . | |
| 5,552,289 | 9/1996 | Sibley et al. ........................... | 435/7.21 |
| 5,580,736 | 12/1996 | Brent et al. .................................. | 435/6 |
| 5,667,987 | 9/1997 | Buckbinder et al. .................. | 435/69.1 |
| 5,776,502 | 7/1998 | Foulkes et al. .......................... | 424/617 |

FOREIGN PATENT DOCUMENTS

| | | |
|---|---|---|
| WO 96/01899 | 1/1996 | WIPO . |
| WO 96/30505 | 10/1996 | WIPO . |

OTHER PUBLICATIONS

Gstaiger et al, "BZLF1 (Zebra, Zta) protein of epstein–barr virus selected in a yeast one–hybrid system by binding to a consensus site in the IgH intronic enhancer: A role in immunoglobulin expression", Biol. Chem. 377:669–673, Oct. 1996.

Alberts et al., Molecular Bioology of the Cell, 2nd Edition, Garland Publishing, pp. 54–55 (1989).

Andreadis et al., "Nucleotide Sequence of Yeast LEU2 Shows 5'–Noncoding Region Has Sequences Cognate to Leucine," Cell, vol. 31:319–325 (1982).

Balzi et al., "PDR5, a Novel Yeast Multidrug Resistance Conferring Transporter Controlled by the Transcription Regulator PDR1," J. Biol. Chem., vol. 269(3):2206–2214 (1994).

Balzi et al., "The Multidrug Resistance Gene PDR1 from Saccharomyces cerevisiae," J. Biol. Chem., vol. 262:16871–16879 (1987).

Balzi et al, "Yeast Multidrug Resistance: The PDR Network," J. Bioenerg. Biomembr., vol. 27(1):71–76 (1995).

Berben and Hilger, Studies on the structure, expression and function of the yeast regulatory gene PHO2 Gene, vol. 66:307–312 (1988).

Bitter et al., "A mult–component upstream activation sequence of the Saccharomyces cerevisiae glyceraldehyde–3–phosphate dehydrogenase gene pormoter," Mol. Gen. Genet., 231:2232 (1991).

Colas et al., "Genetic selection of peptide aptamers that recognize and inhibit cyclin–dependent kinase 2," Nature, vol. 380:548–550 (1996).

Decottingies et al., "Identification and Characterization of SNQ2, a New Multidrug ATP Binding Cassette Transporter of the Yeast Plasma Membrane," J. Biol. Chem., vol. 270(30):18150–18157 (1995).

Delaveau et al., "PDR3, a new yeast regulatory gene, is homologous to PDR1 and controls the multidrug resistance phenomenon," Mol. Gen. Genet., vol. 244:501–511 (1994).

EI–Diery et al., "WAFI/CIP1 is Induced in p53–mediated G1 Arrest and Apoptosis," Cancer Res., vol. 54:1169–74 (1994).

Elledge, "Cell Cycle Checkpoints Preventing an Identity Crisis," Science, vol. 274:1664–1672 (1996).

Elledge and Spottswood, "A new human p34 protein kinase, CDK2, identified by complementation of a cdc28 mutation in Saccharomyces cerevisiae, is a homolog of Xenopus Eg1," EMBO J., vol, 10(9):2653–2659 (1991).

Endicott and Ling, "The Biochemistry of P–Glycoprotein–Mediated Multidrug Resistance," Ann. Rev. Biochem., vol. 58:137–171 (1989).

Espinoza et al., "Cell Cycle Control by a Complex of the Cyclin HCS26 (PCL1) and the Kinase PHO85," Science, vol. 266:1388–1391 (1994).

Fields and Song, "A Novel Genetic System to Detect Protein–Protein Interactions," Nature, vol. 340:245–246 (1989).

Freier et al., "Deconvolution of Combinatorial Libraries for Drug Discovery: A Model System," J. Medicinal Chem., vol. 38:344–52 (1995).

(List continued on next page.)

Primary Examiner—Jeffrey Fredman
Attorney, Agent, or Firm—Cooley Godward LLP

[57] ABSTRACT

A method of screening for a compound that affects mammalian cell cycle regulatory proteins, comprising (A) administering a compound to a cell line, wherein the cell line comprises genetic information comprising (1) a reporter gene operably linked to a gene expression control sequence, wherein the gene expression control sequence comprises an upstream activation sequence and a promoter, and the upstream activation sequence comprises a DNA region that binds to a transcription control factor that is regulated through phosphorylation by a cyclin/CDK phosphorylation system; and (2) a hybrid gene comprising a first coding region from a gene native to the cell line and a second coding region from a second gene, wherein the first gene encodes a gene product that affects phosphorylation by the cyclin/CDK phosphorylation system, and the second gene is mammalian and is homologous to the native gene, and the hybrid gene provides a gene product effective to permit normal cyclin/CDK regulation of the transcription control factor; and (B) analyzing expression of the reporter gene in the cell line, thereby determining whether the compound affects normal regulation. Specific cell lines and methods are also part of the present invention.

33 Claims, 8 Drawing Sheets

OTHER PUBLICATIONS

Frohlich et al., "Yeast Cell Cycle Protein CDC48p Shows Full Length Homology to the Mammalian Protein VCP and is a Member of a Protein Family Involved in Secretion, Peroxisome Formation, and Gene Expression," J. Cell Biol., vol. 114:443–449 (1991).

Galaktionov et al., "CDC25 Phosphatases as Potential Human Oncogenes," Science, vol. 260:1575–1577 (1995).

Harper et al., "The p21 Cdk–Interacting Protein Cip 1 is a Potent Inhibitor of G1 Cyclin–Dependent Kinases," Cell, vol. 75:805–816 (1993).

Hartwell and Kastan, "Cell Cycle Control and Cancer," Science,, vol. 266:1821–26 (1994).

Hatakeyama et al., "Collaboration of $G_1$ cyclins in the functional inactivation of the retinoblastoma protein," Genes Dev., vol. 8:1759–1771 (1994).

Higgins, "ABC Transporters: From Microorganisms to Man," Ann. Rev. Cell Biol., vol. 8:67–113 (1992).

Hirai and Sherr, "Interaction of D–Type Cyclins with a Novel myb–Like Transcription Factor, DMP1," Mol. Cell Biol., vol. 16:6457–6467 (1966).

Hunter, "Braking the Cycle," Cell, vol. 75:839–841 (1993).

Hunter and Pines, "Cyclins and Cancer II: Cyclin D and CDK Inhibitors Come of Age," Cell, vol. 79:573–582 (1994).

Ito et al., "Transformation of Intact Yeast Cells Treated with Alkali Cations," J. Bacteriol., 153:163–168 (1983).

Jayaraman et al., "The activation domain of a basic helix–loop–helix protein is masked by repressor interaction with domains distinct from that required for transcription regulation," EMBO J., vol. 13:2192–99 (1994).

Jeffrey et al., "Mechanism of CDK activation revealed by the structure of a cyclinA–CDK2 complex," Nature, vol. 376:313–20 (1995).

Johnston and Carlson, The Molecular and Cellular Biology of the Yeast Saccharomyces, vol. 2:193–281 (1992).

Kaffman et al., "Phosphorylation of the Transcription Factor PHO4 by a Cyclin–CDK Complex, PHO80–PHO85," Science, 263:1153–1156 (1994).

Kamb et al., "A Cell Cycle Regulatory Potentially Involved in Genesis of Many Tumor Types," Science, vol. 264:436–440 (1994).

Katzmann et al., "Expression of an ATP–Binding Cassette Transporter–Encoding Gene (YOR1) is Required for Oligmycin Resistance in Saccharomyces cervisiae," Mol. Cell. Biol., vol. 15:6875–6883 (1995).

King et al., "How Proteolysis Drives the Cell Cycle,"Science, vol. 274:1652–1659 (1996).

Koff et al., Science, "Negative Regulation of G1 in Mammalian Cells: Ingibition of Cyclin E–Dependent Kinase by TGF–$\beta$," vol. 260:536–539 (1993).

Kuchin et al., "Cyclin–dependent protein kinase and cyclin homologs SSN3 and SSN8 contribute to transcriptional control in yeast," Proc. Nat'l. Acad. of Sci., vol. 92:4006–10 (1995).

La Thangue, DP and E2F proteins: components of a heterodimeric transcription factor implicated in cell cycle control, Current Opinion in Cell Biology, vol. 6:443–50 (1994).

Lenburg et al., "Signaling phosphate starvation," TIBS, vol. 21:383–387 (1996).

Liao et al., "A kinase–cyclin pair in the RNA polymerase II holoenzyme," Nature, vol. 374(9):193–96 (1995).

Madden et al., Structure and expression of the PHO80 gene of Saccharomyces, Nucl. Acids Res., vol. 16:2625–2637 (1988).

Marger and Saier, "A major superfamily of transmembrane facilitators that catalyse uniport, symport, and antiport," Trends Biochem. Sci., vol. 18:13–20 (1993).

Marx, "How p53 Suppresses Cell Growth," Science, vol. 262:1644–1645 (1993).

Marx, "How Cells Cycle Toward Cancer," Science, vol. 263:319–321 (1994).

Measday et al., "The PCL2 (ORFD)–PHO85 Cyclin–Dependent Kinase Complex: A Cell Cycle Regulator in Yeast," Science, vol. 266:1391–1395 (1994).

Morgan, "Principles of CDK regulation," Nature, vol. 374:131–134 (1995).

Morosetti et al., "Alterations of the $p27^{KIP1}$ Gene in Non–Hodgkin's Lymphomas and Adult T–Cell Leukemia/Lymphoma," Blood, vol. 86:1924–30 (1995).

Mumberg et al., "Regulate promoters of Saccharamycs cerivisiae: comparison of transcriptional activity and their use for heterologous expression," Nucleicc Acids Research, vol. 22:5767–5768 (1994).

Murray, "Creative blocks: cell–cycle checkpoints and feedback controls," Nature, vol. 359:599–604 (1992).

Nakayama et al., "Disappearance of Lymphoid System in Bcl–2 Homozygous Mutant Chimeric Mice," Science, vol. 261:1584–1588 (1993).

Nigg, "Cellular substrates of $p34^{cds2}$ and its companion cyclin–dependent kinases," Trends Cell Biol., vol. 3:296–301 (1993).

Nobori et al., "Deletions of the cyclin–dependent kinase–4 inhibitor gene in multiple human cancers," Nature, vol. 368:753–756 (1994).

Nurse P., "Universal control mechanism regulating onset of M–phase," Nature, vol. 344:503–508 (1990).

O'Connell and Baker, "Possible Cross–Regulation of Phosphate and Sulfate Metabolism in Saccharomyces cerevisiae, "Genetics, 132:63–73 (1992).

Ogas et al., "Transcriptional Activation of CLN1, CLN2, and a Putative New G1 Cyclin (HCS26) by SWI4, a Positive Regulator of G1–Specific Transcription," Cell., vol. 66:1015–1020 (1991).

Ogawa et al., "Functional Domains of Pho81p, an Inhibitor or Pho85p Protein Kinase, in the Transduction Pathway of $P_i$ Signals in Saccharmoyces cerevisiae," Mol. Cell. Biol., vol. 15:997–1004 (1995).

O'Neill et al., "Regulation of PHO4 Nuclear Localiztation by the PHO80–PHO85 Cyclin–CDK Complex," Science, vol. 271:209–212 (1996).

Oshima, The Molecular Biology of the Yeast Saccharomyces: Metabolism and Gene Expression, pp. 159–180 (1982).

Paulovich et al., "When Checkpoints Fail," Cell, vol. 88:315–321 (1997).

Peter and Herskowitz, "Joining the Complex: Cyclin–Dependent Kinase Inhibitory Proteins and the Cell Cycle," Cell, vol. 79:181–184 (1994).

Pines, "Cyclins and Cyclin–dependent Kinases: Take Your Partners," Trends Biochem. Sci., vol. 18:195–197 (1993).

Pines, "Arresting Developments in Cell–Cycle Control," Trends Biochem. Sci., vol. 19:143–145 (1994).

Roberts et al., "Cyclins, Cdks, and Cyclin Kinase Inhibitors," CSH Symp. Quant. Biol. LIX, pp. 31–38(1994).

Rose et al., Structure and function of the yeast URA3 gene: expression in Escherichia coli, Gene, vol. 29:113–124 (1984).

Russo, A.A., et al., "Crystal Structure of the p27$^{Kip1}$ Cyclin–dependent–kinase inhibitor bound to the cyclin A–Cdk2 complex," Nature, vol. 382:325–331 (1996).

Santos et al., "Structure–Function Relationships of the Yeast Cyclin–Dependent Kinase Pho85," Mol. Cell. Biol., vol. 15(1):5482–91 (1995).

Schneider et al., "Phosphate–Regulated Inactivation of the Kinase PHO80–PHO85 by the CDK Inhibitor PHO81," Science, vol. 266:122–126 (1994).

Senstag and Hinnen, "The Sequence of the Saccharomyces cerevisiae gene PHO2 codes for a regulatory protein with unusual aminoacid composition," Nucleic Acids Res., vol. 15:233, 241 (1987).

Sherr, "Mammalian $G_1$ Cyclins," Cell, vol. 73:1059–1965 (1993).

Sherr, "Cancer Cell Cycles," Science, vol. 274:1672–1677 (1996).

Shiekhattar, R. et al., "Cdk–activating kinase complex is a component of human transcription factor TFIIH," Nature, vol. 374:283–287 (1995).

Sikorski and Hieter, "A System of Shuttle Vectors and Yeast Host Strains Designed for Efficient Manipulation of DNA in Saccharmyces cerevisiae," Genetics, 122:19–27 (1989).

Stotz and Linder, "The ADE2 gene from *Saccharmyces cerevisiae*: sequence and new vectors," Gene, vol. 95:91–98 (1990).

Toh–e et al., "PHO85, a negative regulator of the PHO system, is a homolog of the protein kinase gene, CDC28, a *Saccharomyces cerevisiae*," Mol. Gen. Genet., vol. 214:162–164 (1988).

Uesono et al., "Negative regulators of the PHO system in *Saccharomyces cerevisiae*: isolation and structural characterization of PHO85," Nucl. Acids Res., vol. 15:10299–10309 (1987).

Vogel and Hinnen, "The Two Positively Acting Regulatory Proteins PHO2 and PHO4 Physically Interact with PHO5 Upstream Activation Regions,"Mol. Cell. Biol., vol. 9(5):2050–57 (1989).

Wolfel, "A p16$^{INK4a}$–Insensitive CDK4 Mutant Targeted by Cytolytic T Lymphocytes in a Human Melanoma," Science, vol. 269:1281–1283 (1995).

Xiong et al., "p21 is a universal inhibitor of cyclin kinases," Nature, vol. 366:701–704 (1993).

Yoshida et al., "Mode of expression of the positive regulatory genes PHO2 and PHO4 of the phosphatase regulon in *Saccharomyces cervisiae*," Mol. Gen. Genet., vol. 217:31–33 (1989).

Zuo et al., "Germline Mutations in the p16$^{INK4a}$ Binding Domain of CDK4 in Familial Melanoma," Nature Genetics, vol. 12:97–99 (1996).

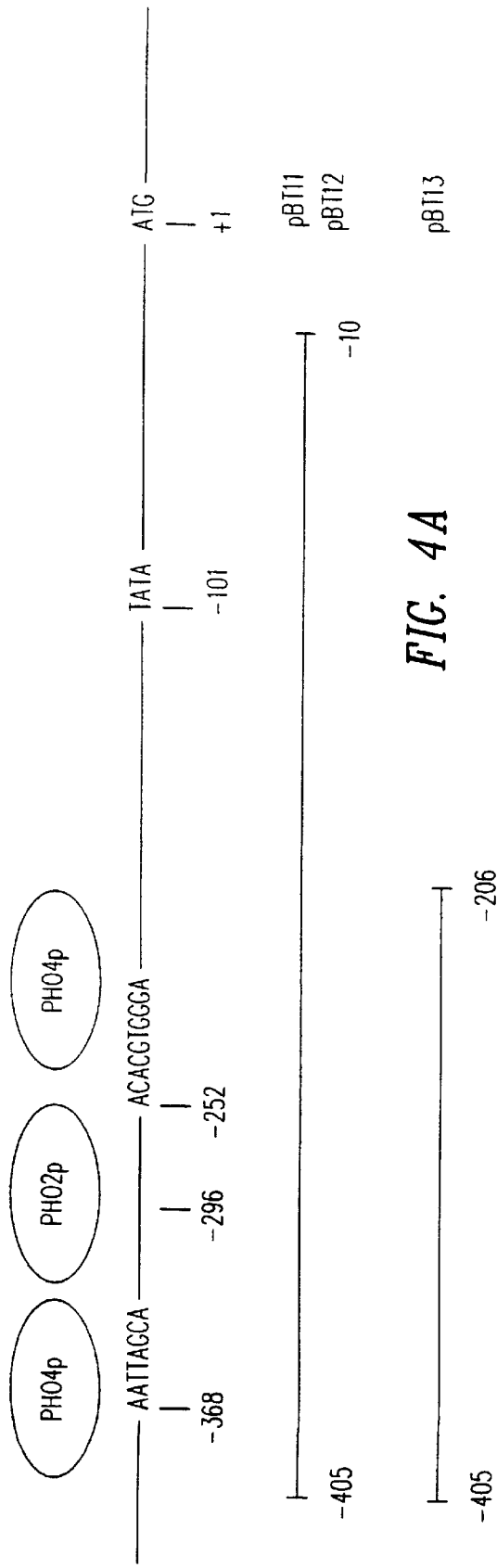
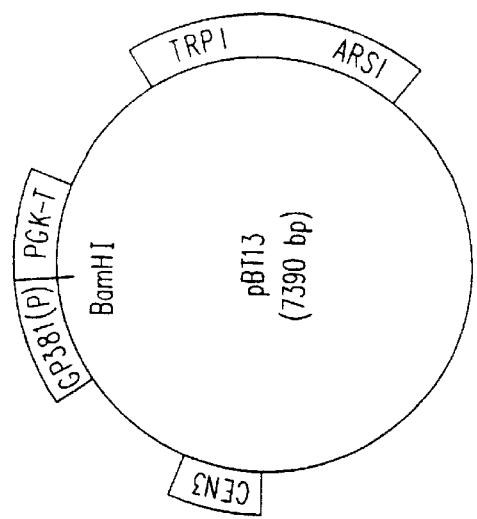
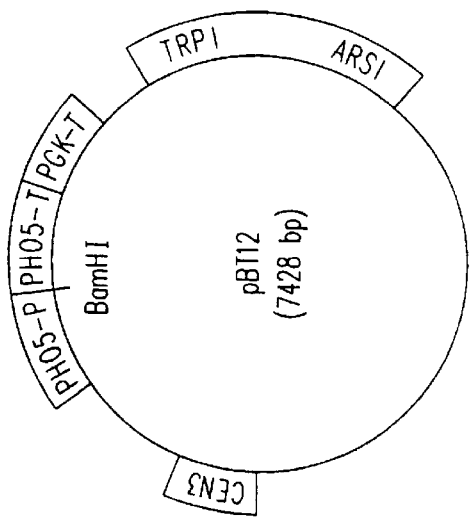
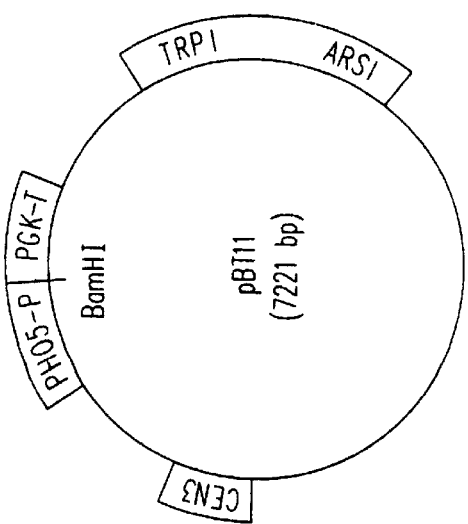
FIG. 4A
FIG. 4B

PHENOTYPIC ASSAYS OF CYCLIN/CYCLIN-DEPENDENT KINASE FUNCTION

The present application is a continuation-in-part of provisional application Ser. No. 60/029,127, filed on Oct. 16, 1996, and provisional application Ser. No. 60/031,968, filed on Nov. 27, 1996.

ACKNOWLEDGEMENTS

This invention was supported in part by grants from the National Cancer Institute (1R43CA67504-01; 1R44CA67504-02). The U.S. Government has certain rights in this invention as a result of such support.

INTRODUCTION

1. Technical Field

This invention relates to methods of identifying inhibitors and activators of mammalian cell cycle regulatory proteins, especially inhibitors and activators of cyclins, cyclin-dependent kinases (CDKs), cyclin/CDK complexes, cyclin kinase inhibitors (CKIs), and cyclin/CDK/CKI complexes, by a functional assay in vivo; to cell lines and vectors useful for these methods; and to cell cycle regulatory products identified by these methods.

2. Background

Cyclin-dependent kinases (CDKs) are serine/threonine protein phosphorylation enzymes that are activated through interaction with cyclins and that phosphorylate (and thus control the activity of) various molecules associated with cell growth and division, thereby controlling progression through various stages of the eukaryotic cell cycle (reviewed in Morgan, 1995, *Nature* 374:131–134; Pines, 1993, *Trends Biochem. Sci.* 18:195–197; Sherr, 1993, *Cell*, 73:1059–1965). CDKs and their regulatory proteins have become a focus of great interest, as understanding their function sheds light on normal cellular growth controls as well as cellular proliferation defects associated with diseases such as cancer. The family of known CDKs is characterized by similar size (35–40 KDa), sequence homology (>40% identity) and, primarily, a phosphorylating ability that is activated by cyclin. The interacting cyclins are correspondingly characterized by the ability to bind and activate CDKs. This binding may be mediated via a relatively conserved, 100-amino-acid, CDK-interacting domain called the "cyclin box." In some cases, the cyclin box constitutes the chief extent of homology among cyclins. Counterposing the activation function of cyclins, a number of proteins have been found to inhibit cyclin/CDK complexes (reviewed in Morgan, 1995; Peter and Herskowitz, 1994, *Cell* 79:181–184; Pines, 1994, *Trends Biochem. Sci.* 19:143–145; Roberts et al., 1994, *CSH Symp. Quant. Biol.* LIX). Although some of the cyclin kinase inhibitors (CKIs) share sequence homology, many CKIs appear to be structurally distinct, revealing further complexities in CDK regulation. The differential synthesis of cyclins during the cell cycle controls the specificity and activity of CDKs, and the abundance of both cyclins and CKIs has been shown to be controlled by differential proteolysis (reviewed in King et al., 1996, *Science* 274:1652–1659). Finally, CDK activity itself can also be regulated positively and negatively by phosphorylation.

Cell cycle regulatory genes were first identified and studied in model eukaryotic systems such as *X. laevis* and the two yeast species *S. cerevisiae* and *S. pombe* (for review, see Murray, 1992, *Nature* 359:599–604). These systems afforded the experimental flexibility to extensively characterize interactions among cyclins, CDKs and CKIs, as well as interactions between these and other proteins. These initial studies provided valuable information to construct models for cell cycle regulation, but the relevance of these models to mammalian cell cycle regulation remained speculative until homologs of these genes were identified in mammalian cells.

Prior to a review of CDKs, it will be helpful to briefly consider the different stages of a normal mammalian cell cycle in order to understand how and at what points the cell cycle can be regulated by CDK activity. Normal mammalian cells pass through a series of stages between cell divisions that are referred to (sequentially) as the first gap phase (G1), synthesis (S), the second gap phase (G2) and mitosis (M). These stages of cell growth and division are associated (generally) with characteristic cellular functions (reviewed in Elledge, 1996, *Science* 274:1664–1672). G1 follows the cell division, or mitosis, that generates the cell. Within the G1 phase, a critical decision is made regarding whether to proceed to S phase and synthesize DNA for another mitosis, or to arrest in G1 phase and postpone cell division until damaged DNA is repaired or, in certain instances, indefinitely. This checkpoint is termed the "restriction point" in mammalian cells and "start" in yeast. Once a commitment to synthesize DNA is made, the cell duplicates its genetic material during S phase and synthesizes necessary proteins in preparation for mitosis during G2. Another decision point exists in G2, when cellular machinery determines if the DNA has been completely replicated and if adequate protein components have been produced to support mitosis. Progression through this checkpoint leads to mitosis, cell division and the next cell cycle. The G1/S phase transition and the G2/M phase transition accordingly serve as crucial checkpoints to monitor appropriate progression through the cell cycle. Further details on cellular activity for each stage of the cell cycle are set out below in connection with the various activities of CDKs and related molecules.

The major CDKs discovered to date in mammalian and yeast cells, as well as the cyclins with which they interact in different phases of the cell cycle, are listed in FIG. 1. In mammalian cells, there are three cyclins referred to as "D-cyclins" which exhibit cell-type-specific expression. Most mammalian cells express cyclin D3 and either cyclin D1 or D2. The D cyclins associate with CDK4 and, in some cell types, also with CDK6 (not shown) and function in G1 phase to promote progression through the restriction point. Other cyclin types (with different reference letters) exhibit different cellular or functional specifications. The cyclin E/CDK2 complex is believed to function after the D cyclins at the G1 to S transition to promote DNA replication. The cyclin A/CDK2 and cyclin B/Cdc2 complexes function during S phase. Cdc2 continues to associate with cyclin B in G2 phase and subsequently with cyclins B and A in mitosis. Several mammalian CKIs have been identified, including p15 (also known as $p15^{INK4b}$, INK4b and MTS2), p16 (also known as $p16^{INK4a}$, INK4a and MTS1), p18 (also known as $p18^{INK4c}$ and INK4c), p19 (also known as $p19^{INK4d}$ and INK4d), p21 (also known as $p21^{CIP1}$, CIP1, SDI1 and WAF1), p27 (also known as $p27^{KIP1}$ and KIP1) and p57 (also known as $p57^{KIP2}$ and KIP2). It should be noted that the cyclins and CDKs depicted in FIG. 1 represent the major species identified to date. Additional species may be known or discovered in the future.

In addition to being regulated by differential synthesis of cyclins and CKIs, CDK activation is also regulated by feedback mechanisms which prevent entry of cells into the next phase of the cell cycle prior to completion of the appropriate macromolecular events (reviewed in Murray, 1992; Hunter and Pines, 1994, *Cell* 79:573–582; Hartwell and Kastan, 1994, *Science* 266:1821–26; Elledge, 1996; Paulovich et al., 1997, *Cell* 88:315–321). The first major checkpoint occurs in G1 and, in *S. cerevisiae*, requires that the cell achieve a minimum size. If this size is achieved and environmental conditions are appropriate, the cell passes Start and proceeds into S phase. In both *S. cerevisiae* and mammalian cells, Start (Restriction Point) is the major checkpoint of the cell cycle, and once this point is passed, the cell is committed to a mitotic division cycle. The second checkpoint at the G2-to-M phase transition ensures that the cell has completed all DNA replication and DNA repair prior to initiating mitosis. While many of the molecular details of the checkpoint mechanisms are incompletely understood, they appear at least in part to involve cyclin-CDK activation. For example, in vertebrates the G1 phase cyclin/CDKs phosphorylate retinoblastoma (Rb) and other related proteins, resulting in activation of genes required for DNA synthesis (reviewed in Nigg, 1993, *Trends Cell Biol.* 3:296–301). Cells do not pass the G1 checkpoint if they contain extensive DNA damage. This is due to p53-dependent induction of p21, a CKI which inhibits the cyclin E/CDK2 complex. Similarly, the G2/M checkpoint appears to directly affect cyclin/CDK activation. Blocks of unreplicated vertebrate DNA inhibit cyclin B1/Cdc2 activation by preventing dephosphorylation of Cdc2, halting further progression through the cell cycle. Thus, cell cycle regulation of cyclin and CKI expression controls the specificity and activity of CDKs, and this regulation is integrated with the major cell cycle checkpoints.

While multiple CDKs have been identified in mammalian cells, yeast appear to have one major CDK (CDC28 in *S. cerevisiae*, and CDC2 in *S. pombe*). In *S. cerevisiae*, CDC28 interacts with cyclins CLNI or CLN2 during G1 and with CLB1, CLB2, CLB3 or CLB4 during G2. The *S. cerevisiae* PCL1/PHO85 and PCL2/PHO85 cyclin/CDK complexes have also been shown to contribute to, but not be required for, cell cycle regulation (Measday et al., 1994, *Science* 266:1391–1395; Espinoza et al., 1994, *Science* 266:1772–1786).

Recent discoveries that human CDKs, cyclins and CKIs are mutated or abnormally expressed in a number of cancerous cells confirm the centrality of these gene products and their functions to mammalian cell cycle regulation (reviewed in Hunter, 1993, *Cell* 75:839–841; Marx, 1993, *Science* 262:1644–1645; Marx, 1994, *Science* 263:319–321; Hunter and Pines, 1994; Hartwell and Kastan, 1994; Sherr, 1996, *Science* 274:1672–1677). For example, abundant evidence now exists that cyclin D1 is equivalent to the bcll oncogene. The amplifications of the genetic region at 11q13, the chromosomal region that includes cyclin D1, suggest that overexpression of the cyclin D1 gene contributes to B cell lymphoma as well as breast and esophageal cancer. Aberrant expression of cyclins D2, D3 and E has likewise been correlated with cancer cells. The CDC25A and CDC25B phosphatases, which remove an inhibitory phosphate from both CDK2 and Cdc2, have been implicated as potential human oncogenes (Galaktionov et al., 1995, *Science* 260:1575–1577). These proteins, in conjunction with either a mutant Ha-RAS or loss of RB1, promote oncogenic focus formation in a rodent model. Overexpression of CDC25B was observed in 32% of human primary breast tumors tested. The interaction between CDKs and CKI proteins in particular has been highlighted by studying cancerous cells. The p16$^{INK4a}$ CKI protein, which binds to CDK4, appears to function directly as a tumor suppressor; p16$^{INK4a}$ is deleted in cell lines derived from a variety of different tumors (Kamb et al., 1994, *Science* 264:436–440; Nobori et al., 1994, *Nature* 368:753–756). Moreover, certain human melanomas have been shown to contain missense mutations in the CDK4 gene that encode proteins that are refractory to inhibition by p16$^{INK4a}$ (Wolfel, 1995, *Science* 269:1281–1283; Zuo et al., 1996, *Nature Genetics* 12:97–99). Alterations of the CKI p27$^{Kip1}$ have also been implicated in the pathogenesis of some hematologic malignancies (Morosetti et al., 1995, *Blood* 86:1924–30). Finally, TGF-β, which inhibits mammalian cell growth in a manner similar to that observed with contact inhibition in cell culture, prevents assembly and activation of cyclin E/CDK2 complexes (Koff et al., 1993, *Science* 260:536–539). It has also been speculated that the tumor suppressor gene p53 exerts part of its effect through cell cycle control. Over 50% of human cancers harbor a mutation in p53. As mentioned earlier, the wild type p53 protein stimulates expression of a 21 kilodalton protein (p21), a CKI which inhibits CDK2. CDK2 activity is required for a mammalian cell to pass the restriction point and begin DNA replication (El-Diery et al., 1994, *Cancer Res.* 54:1169–74; Harper et al., 1993, *Cell* 75:805–816; Xiong et al., 1993, *Nature* 366:701–704).

TABLE I

| Cancer Defect | Associated Cell Cycle Proteins | Desired Therapeutic Activity |
| --- | --- | --- |
| p16$^{INK4a}$ | cyclin D1, D2, D3, CDK4, CDK6, PCNA, Rb | Restore p16$^{INK4a}$ function, or p16$^{INK4a}$ mimetic, or cyclin D/CDK4 inhibitor |
| CDK4 | cyclin D1, D2, D3, PCNA, Rb | Restore p16$^{INK4a}$ function, or p16$^{INK4a}$ mimetic, or cyclin D/CDK4 inhibitor |
| Cyclin D1, D2, D3 | CDK4, CDK6, Rb | cyclin D/CDK4 inhibitor or cyclin D/CDK6 inhibitor |
| p53 | p21, CDK4, CDK2 | p21 mimetic, or cyclin E/CDK2 inhibitor |
| p21 | CDK4, CDK2, p107, E2F | Restore p21 function, or p21 mimetic, or cyclin E/CDK2 inhibitor |
| TGF-β Receptor | p27, CDK2, CDK4 | p21 mimetic, or cyclin D/CDK4 inhibitor or cyclin E/CDK2 inhibitor |
| Cyclin E | p21, p27, CDK2, p107, E2F | cyclin E/CDK2 inhibitor |
| CDC25 | cyclin A, CDK2 p107, E2F | CDC25 inhibitor, or a cyclin A/CDK2 inhibitor or a Cdc2 inhibitor |
| Cyclin A | CDK2, Cdc2, p107, E2F | cyclin A/CDK2 inhibitor or cyclin A/Cdc2 inhibitor |

Table I summarizes the cell cycle related genes that have been documented to be defective in various cancers. These defects are either mutations in, or aberrant expression of, genes encoding cyclins, CDKs, CKIs or other proteins that affect the activity of these cell cycle regulatory proteins. For the majority of cancers exhibiting cell cycle defects, the loss of cellular growth control appears to reflect the failure to inhibit a particular CDK. Specifically CDK2, CDK4 or CDK6 appears to be inappropriately active due to the lack of normal CDK inhibition controls.

Most cancer therapeutics currently in use are cytotoxic compounds which were frequently identified by their ability to kill rapidly growing tumor cells in culture. The strategy in utilizing these compounds for therapy has been to attempt to kill cancer cells while limiting the toxicity for the patient. These antineoplastic agents generally function by damaging DNA, inhibiting DNA replication or precursor synthesis, inhibiting DNA topoisomerases or by disrupting function of the mitotic apparatus. Chemotherapeutic agents currently in use are effective against certain cancers but, in general, have been of limited therapeutic value. Since these cytotoxic compounds are frequently ineffective and generally have significant adverse effects on the patient, considerable need exists for the development of more efficacious therapies.

To date, only limited technology has been described for identifying compounds that affect the activity of cell cycle regulatory proteins. Colas et al. (1996, *Nature* 380:548–550) recently described a two-hybrid (Fields and Song, 1989, *Nature* 340:245–246) selection which identified peptide aptamers from a random sequence library that are capable of interacting with human CDK2. Some of the aptamers so identified were shown in vitro to inhibit cyclin E/CDK2 phosphorylation of the non-specific substrate, histone H1. Because this screen is limited to identifying peptides which physically associate with CDK2, it does not select for compounds with functional activity nor does it accommodate screening for non-peptide inhibitors such as small molecules and various combinatorial libraries. Moreover, in vitro assays do not mimic physiological conditions under which therapeutics are administered.

Cell-based screening technology has the potential to identify lead compounds that affect cell cycle regulatory proteins and that may have therapeutic utility. Draetta et al. (U.S. Pat. No. 5,443,962) disclose one method of identifying cell cycle regulatory proteins that inhibit CDC25 phosphatase. This screen only detects proteins acting through CDC25, and is dependent on the use of cells that have been manipulated to have a hypermitotic phenotype.

As discussed earlier, the majority of cancer-associated cell cycle defects identified thus far involve a failure to inhibit the activity of a CDK. While specific cyclin/CDK inhibitors may thus be therapeutically indicated, identifying such inhibitors in cell-based screens poses a challenge in that these inhibitors are expected to exhibit the phenotype of arresting cell cycle progression. Because any toxic compound added to a proliferating culture will similarly cause inhibition of growth, an initial screen would not be effective to distinguish the numerous non-specific toxic compounds from those that specifically target the cyclin/CDK of interest. There exists a need for a cell-based assay for identifying inhibitors of specific cyclin/CDK complexes that is amenable to high throughput screening.

PHO5 Regulation

The PHO5 gene of *S. cerevisiae* encodes a secreted acid phosphatase. Transcription of the gene is repressed when yeast are grown in high concentrations of inorganic phosphate, and transcription of the PHO5 gene is induced in response to phosphate starvation. The secreted acid phosphatase generates inorganic phosphate from extracellular nutrients, thus allowing the cells to grow in phosphate depleted medium. Genetic studies (reviewed in Oshima, 1982, In: The Molecular Biology of the Yeast Saccharomyces: Metabolism and Gene Expression, pp. 159–180; Johnston and Carlson, 1992, In: The Molecular and Cellular Biology of the Yeast Saccharomyces, Vol. 2: 193–281) have identified positive regulatory genes PHO2, PHO4 and PHO81 and negative regulatory genes PHO80 and PHO85 comprising this regulon. PHO2 and PHO4 encode transcription factors that bind to an upstream activation sequence ($UAS_{PHO5}$) in the PHO5 expression control sequences to activate transcription (Senstag and Hinnen, 1987, *Nucleic Acids Res.* 15:233, 241; Berber and Hilger, 1988, *Gene* 66:307–314; Vogel and Hinnen, 1989, *Mol. Cell. Biol.* 9:2050–56; Yoshida et al., 1989, *Mol. Gen. Genet.* 217:31–33). Both PHO80 and PHO85 are required for repression of PHO5 gene transcription. The PHO85 gene sequence shows that the encoded protein has significant amino acid sequence homology to the major yeast CDK, CDC28p (Toh-e et al., 1988, *Mol. Gen. Genet.* 214:162–164). Furthermore, the PHO80 gene product is homologous to two yeast cyclins. Within a 120 amino acid cyclin homology region that contains residues conserved in all cyclins, PHO80p is 33% identical to both PCL1p (HCS26p; Ogas et al., 1991, *Cell* 66:1015–1020) and PCL2p (ORFDp; Frohlich et al., 1991, *J. Cell. Biol.* 114:443–449).

The negative regulators of PHO5 gene expression, PHO80p and PHO85p, satisfy the biochemical definition of an interacting cyclin-CDK pair (Kaffman et al., 1994, *Science* 263:1153–1156). PHO80p and PHO85p form a complex, and the purified PHO80p/PHO85p complex can interact with purified PHO4p in vitro. The purified PHO80p/PHO85p complex phosphorylates PHO4p in vitro, creating a phosphorylation pattern similar to the in vivo phosphorylation pattern of PHO4p (O'Neill et al., 1996, *Science* 271:209–212). The positive regulator PHO81 has been shown to encode a protein that binds to and inactivates the PHO80p/PHO85p complex (Schneider et al., 1994, *Science* 266:122–126. Transcription of PHO81 is induced by phosphate starvation. Increased synthesis of PHO81p, in conjunction with an apparent post-translational modification in low phosphate, results in inactivation of the PHO80p/PHO85p cyclin/CDK causing derepression of PHO5 (Ogawa et al., 1995, *Mol. Cell. Biol.* 15:997–1004). Thus, the PHO81 encoded protein appears to function as a CKI, inactivating the PHO80p/PHO85p kinase and thereby preventing phosphorylation of PHO4p. Although PHO80, PHO85 and PHO81 satisfy the biochemical definition of a cyclin, CDK and CKI, respectively, they do not appear be required for normal cell cycle control since the genes can be deleted individually or in combination without major effects on cell growth properties.

CDKs are a highly conserved family of proteins. For example, the major *S. cerevisiae* CDK, CDC28p, shares over 51% amino acid homology with PHO85p (Toh-e et al., 1988). Although the native CDC28p does not complement a deletion of the PHO85 gene, Santos et al., 1995, *Mol. Cell. Biol.* 15:5482–91) demonstrated that chimeric yeast CDKs, wherein various regions of PHO85p were substituted by the homologous region from CDC28p, retained PHO85p function with respect to PHO5 promoter regulation. Thus, among these two yeast CDKs, regions of the homologous CDKs are to some extent functionally conserved.

The functions of certain mammalian cell cycle regulatory proteins have been analyzed in yeast. The human cdc2 gene product is able to functionally replace the *S. pombe* cdc2 gene product (Lee et al., 1987, *Nature* 344:503–508), while the human CDK2 gene can complement a *S. cerevisiae* temperature sensitive cdc28 mutation (Elledge and Spottswood, 1991, *EMBO J.* 10:2653–2659). The cell cycle-dependent phosphorylation of human retinoblastoma protein (pRB) is faithfully reproduced in *S. cerevisiae* (Hatakeyama et al., 1994, *Genes Dev.* 8:1759–1771). This phosphorylation is dependent on yeast CLN3 and either CLN1 or CLN2. Furthermore, the functions of yeast CLN2p and CLN3p in pRB hyperphosphorylation can be complemented by expression of human cyclin E and cyclin D1, respectively. Thus, the function of native mammalian cyclins, CDKs and other cell cycle regulatory proteins may be measured in vivo by complementation of specific yeast mutations.

The convergence of cancer research and cell cycle research has presented the opportunity to develop novel cancer therapeutic agents by targeting specific proteins that are mutant or aberrantly regulated in cancer cells. This opportunity has highlighted the absence of adequate screening methods for identifying agents that specifically influence the activity of cell cycle regulatory proteins. The need exists for in vivo, cell-based screening methods that are amenable to high throughput screening for new drug discovery. In particular, the need exists for a screen that distinguishes specific cyclin/CDK inhibitors from general cytotoxic compounds.

DEFINITION OF TERMS

Cell cycle regulatory genes are genes that control and coordinate progression from one stage of a cell cycle to the next stage or to the next cell cycle. These genes include cyclins, cyclin-dependent kinases, cyclin-dependent kinase inhibitors, cyclin and/or CDK phosphatases, and genes whose protein products regulate the activity of these genes or proteins.

Transcription control factors are regulatory proteins that bind to DNA expression control sequences, RNA Polymerase or other transcription factors to modulate the activity of the RNA Polymerase complex and to control transcription of DNA into messenger RNA.

Promoter sequences are functionally defined DNA sequences that direct transcription of DNA. At a minimum, RNA Polymerase interacts with promoter sequences to initiate transcription of a gene.

Homologous is used to define two sequences that have substantial similarity to each other. Substantial similarity may be determined by using computer programs known in the art such as those provided by the Genetics Computer Group, Inc. For example, the homology of a given sequence with individual members of a sequence database may be established using the FastA program. For a group of related sequences, the PileUp program creates a multiple sequence alignment showing regions of homology. The Compare program identifies segments of homology between two sequences while the BestFit program determines the optimal alignment of two sequences. A preferred determination of homology compares two amino acid sequences over a stretch comprising at least 20 amino acids, and alignment reveals amino acid identity or amino acid conservation in at least 30% of the amino acid positions. Amino acid conservation refers to amino acids that are different but have similar chemical properties (see Alberts et al., 1989, Molecular Biology of the Cell, 2nd Edition, *Garland Publishing*, pp. 54–55). Similarly, a preferred determination of nucleotide sequence homology compares two nucleotide sequences over a stretch comprising at least thirty nucleotides, and alignment of the sequences reveals nucleotide identity in at least 30% of the nucleotide positions.

Hybrid gene is a gene comprising sequences from two or more original genes. Accordingly, hybrid proteins are the gene products encoded by hybrid genes.

Target gene is herein used to describe a mammalian cell-cycle regulatory gene, also referred to herein as the "second" gene, whose activity is measured by the methods of the current invention.

Chromosomal mutation is an alteration of a chromosomal gene that causes the gene to be incapable of producing a functional gene product; the alteration can be one or more point mutations, an insertional mutation such as a gene disruption, or the deletion of all or part of the gene.

SUMMARY OF THE INVENTION

Accordingly, it is an object of the present invention to provide methods, compositions, and systems that allow the discovery of compounds, methods and systems that provide additional manipulation of cell cycles or cell cycle regulatory proteins. These and other objects of the invention as will hereinafter be readily apparent have been accomplished by providing, in part, a method of screening for a compound that affects cell cycle control of a target cell, comprising administering a compound to a host cell line, wherein the host cell line comprises genetic information comprising a reporter gene operably linked to a gene expression control sequence, wherein the gene expression control sequence comprises an upstream activation sequence and a promoter, and the upstream activation sequence comprises a DNA region that binds to a transcription control factor that is regulated directly or indirectly through phosphorylation by a cyclin/CDK phosphorylation system; and a hybrid gene comprising a first coding region from a first gene native to the host cell line and a second coding region from a second gene, wherein the first gene encodes a gene product that affects phosphorylation by the cyclin/CDK phosphorylation system, and the second gene is from the target cell and is homologous to the first gene, and the hybrid gene provides a gene product effective to permit normal cyclin/CDK regulation of the transcription control factor; and analyzing expression of the reporter gene in the host cell line, thereby determining whether the compound affects target cell cycle regulation. There are a number of related aspects of the invention that are described in more detail below, including entirely different methods that allow identification of mutations and compounds that affect the same, or different, molecular components of cell cycle control systems, methods that actually control cell cycles, and compositions that find use in some or all of the methods. All of the methods, compositions and systems described below that allow identification of any factor that affects a cell cycle control mechanism or that themselves actually affect a cell cycle control mechanism are aspects of the present invention.

BRIEF DESCRIPTION OF THE DRAWINGS

The invention now being generally described, the same will be better understood by reference to the following drawings, which illustrate various aspects of the invention when considered in combination with the corresponding sections of the specification.

FIGS. 4A and 4B are schematic representations of the PHO5 expression control sequences and the plasmids pBT11, pBT12 and pBT13.

DESCRIPTION OF SPECIFIC EMBODIMENTS

Figure 1:
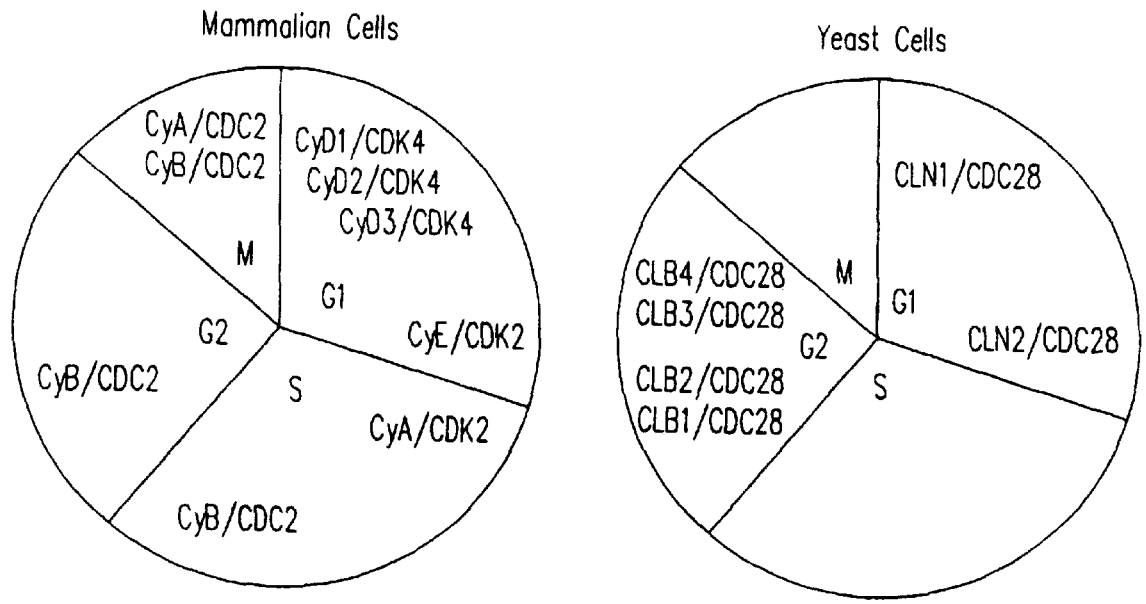
FIG. 1 is a diagram showing the major CDKs known to exist in mammalian and *S. cerevisiae* cells, the cyclins with which each CDK interacts, and the different phases of the cell cycle in which they act.

The present invention provides a number of related techniques for controlling cell cycle regulation for a variety of purposes, such as stimulating growth of cells (as in wound healing) or regulating excessive cell growth and division (as in cancer therapy). There are a number of aspects of the invention that can be separately practiced, such as processes useful for the discovery of compounds that will be effective in regulating cell growth (e.g., drug discovery), as well as the application of the discovered compounds to either up-regulate or down-regulate cell growth, so that it is not necessary (or even desirable) to practice all of the aspects of the invention at the same time. Routine testing is part of practicing the invention. Each of the aspects of the invention can be understood by reference to the details of the individual components and methods used in the practice of the different aspects of the invention. The components and method steps will accordingly be discussed in detail, as well as being discussed to show their interaction with other steps and components of the invention.

Cyclin/CDK complexes phosphorylate an array of proteins within a cell. One class of substrates for these complexes comprises transcription control factors. In appropriately chosen cases, the genes regulated by these transcription factors owe their expression to strict control by one specific cyclin/CDK pair. By linking the expression control sequences of these regulated genes to reporter genes, functionality of the specific cyclin/CDK pair can be studied in in vivo assays. The present invention provides assays and reagents for identifying circumstances, including those involving genes, mutations and compounds, that affect the activity of mammalian cell cycle regulation gene products. For example, in one embodiment a cell line is provided in which functional sequences from a mammalian gene are substituted for sequences of a native yeast cell cycle regulatory gene that regulates transcription. Because the mammalian sequences impart the function of the native cell cycle regulatory gene sequences being replaced, agents that interfere with or alter the functionality of the peptides encoded by the mammalian gene sequences (and thus affect the cell cycle of the cell from which the mammalian DNA sequence is obtained) can be identified by analyzing expression of a reporter gene that is operably linked to the expression control sequences.

Reporter Genes

The invention uses a reporter gene whose activity will indicate the integrity of the cyclin/CDK phosphorylating system used in the assay. The reporter gene can be any gene whose expression is detectable, for example by an enzymatic activity assay, a nutritional assay, a structural assay, as by an immunoassay, or by antibiotic resistance or other selection. A variety of reporter genes are commonly utilized and well known in the art (See Example 1). For example, the reporter gene is selected from the group consisting of the *E. coli* LacZ (encoding β-galactosidase), the *E. coli* tn5 neo gene, the LEU2, URA3, HIS3, and LYS2 genes of *S. cerevisiae*, the jelly fish (*Aequorea victoria*) green fluorescent protein gene, the firefly (*Photinus pyralis*) luciferase gene and the chloramphenicol-acetyl transferase (CAT) gene. LEU2, URA3, HIS3, and LYS2 are preferred for their ability to provide a positive selection for yeast cells expressing the reporter gene, where promoter activity confers the ability of cells that are mutant in the corresponding genes to grow in culture media lacking leucine, uracil, histidine or lysine, respectively. For example, if LEU2 is used as a reporter gene in a system where phosphorylation by the cyclin/CDK inactivates a positively acting transcription factor, a cyclin kinase-inhibitor that antagonizes the cyclin/CDK will induce transcription of LEU2 under specific conditions. Under conditions where the native inhibitor is not expressed, leu2$^-$ cells in leucine-depleted medium will only grow if the LEU2 reporter gene is caused to be expressed. Thus, agents that inhibit the cyclin/CDK phosphorylation system can be identified by their ability to promote cell growth in leucine-depleted media. The tnS neo gene likewise is preferred as a reporter gene for conferring to bacterial, yeast or mammalian cells the ability to grow in medium containing the antibiotic G418 (neomycin or geneticin).

URA3 and LYS2 genes are more preferred for their additional ability to provide a positive selection for cells that do not appropriately activate transcription of the particular CDK-responsive promoter. Yeast cells expressing the URA3 gene are not viable in media containing 5-fluoroorotic acid (FOA), while those expressing the LYS2 gene are not viable in media containing α-aminoadipate (AAD). These reporter genes are thus useful to select for cells that acquire the ability to repress transcription from the particular CDK-responsive promoter. For example, if phosphorylation by the cyclin/CDK inactivates a positively acting transcription factor in the system and thus represses transcription of the reporter gene, a mutation or compound that incapacitates cyclin/CDK phosphorylation activity will allow transcription of the reporter gene under conditions where transcription would normally be repressed. Cells expressing URA3 as a reporter gene will not be viable in a medium containing FOA. Similarly, cells expressing LYS2 as a reporter gene will not be viable in medium containing AAD. Therefore, by using URA3 or LYS2 as reporter genes, agents that compensate for the defect in cyclin/CDK activity can be identified by their ability to confer viability to cells grown in FOA or AAD, respectively.

Alternatively, this type of positive selection can be used with the above mentioned reporter genes to identify inhibitors of a CKI that inhibits a specific cyclin/CDK. Under conditions where expression of active CKI derepresses transcription, cells having a URA3 reporter gene will not grow in the presence of FOA, while cells having a LYS2 reporter gene will not grow in the presence of AAD. Inhibitors of CKI will reinstate the repressed state and allow growth in FOA or AAD, respectively. In other embodiments, the LacZ gene, firefly luciferase gene, the jelly fish green fluorescent protein gene and the CAT gene encode proteins that allow optical quantitation of the activity of the cyclin/CDK-responsive promoter. Expression of these reporter genes can be monitored by optical sensors and are particularly suited for automated high throughput screening. It will be apparent to those skilled in the art that if the transcription factor that positively regulates reporter gene expression is activated, rather than repressed, by a specific cyclin/CDK, then the phenotypes conferred by the above reporter genes in this strain will reflect the opposite state of the cyclin/CDK (active or inhibited) than the examples above. Similarly, a transcriptional repressor whose activity is regulated by a cyclin/CDK will confer specific phenotypes from each reporter gene dependent on whether the cyclin/CDK activates or inhibits the transcriptional repressor.

CDK Responsive Expression Control Sequences for Expressing Reporter Genes

Expression control sequences of the current invention comprise upstream activation sequences and promoter sequences. Transcription regulatory factors and RNA polymerase bind to these sequences to regulate the timing and extent of transcription of the downstream gene sequences. The upstream activation sequences used in the present invention include various DNA regions that bind transcription factors, the activities of which are controlled, either directly or indirectly, by a cyclin/CDK phosphorylating complex. The complex can regulate transcription through directly phosphorylating a DNA-binding transcription factor, where the phosphorylation state of the transcription factor corresponds to its ability to activate or repress transcription. Alternatively, the cyclin/CDK complex can regulate transcription indirectly through phosphorylating a protein that interacts with a DNA-binding transcription factor, where an interaction regulates the activity of the transcription factor. Examples of such upstream activation sequences are known in the art (Dynlacht et al., 1995, Nature 374:114). In another embodiment the RNA polymerase itself can be regulated directly or indirectly by a cyclin/CDK phosphorylating complex (Liao et al., 1995, Nature 374:193–96).

Figure 8:
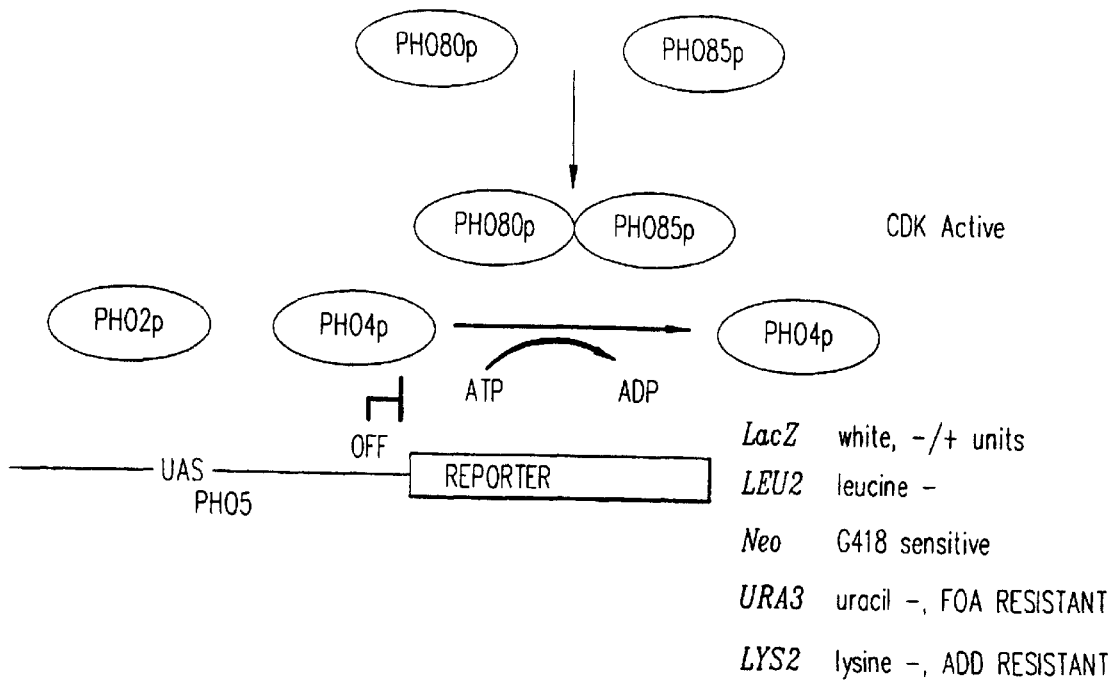
FIG. 8 is a diagram of the proteins of the PHO5 regulon controlling expression of various reporter genes.
Figure 8:
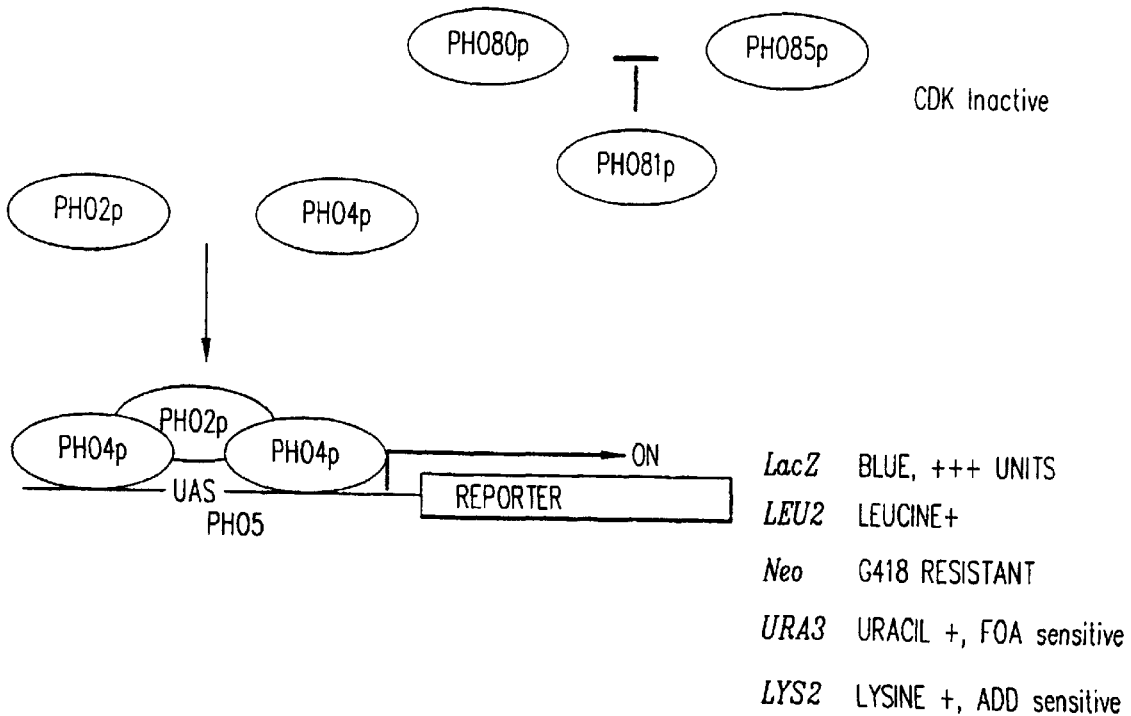

The upstream activation sequences of the current invention are most preferably from the PHO5 gene of S. cerevisiae. In this embodiment, preferred cell lines are strains of S. cerevisiae. The PHO5 gene encodes a secreted acid phosphatase, and regulation of PHO5p expression is dependent on concentrations of inorganic phosphate. Specifically, the PHO5 expression control sequences are activated by the yeast transcription factor PHO4p, whose activity is regulated by the cyclin/CDK pair PHO80p/PHO85p. In high concentrations of inorganic phosphate, the PHO80p/PHO85p complex phosphorylates PHO4p to a hyperphosphorylated, inactive state; when yeast are starved for inorganic phosphate, transcription of the CKI gene PHO81 is induced, preventing phosphorylation of PHO4p and allowing PHO4p to activate the PHO5 gene promoter. Thus, expression of the reporter gene from the PHO5 expression control sequences is a direct reflection of PHO4p activity and an indirect reflection of the phosphorylating activity of the PHO80p/PHO85p kinase (FIG. 8).

Upstream activating sequences can be identified using methods well known in the art. Generally, these control sequences reside upstream of the gene coding region and bind to the transcription factors regulated by the relevant cyclin/CDK complex. Minimally, these sequences are also characterized by their ability to confer the transcriptional regulation of the particular gene to a heterologous gene. The upstream activation sequences may be utilized in the same promoter context as found in the native gene. For example, the DNA region at −405 to −10 relative to the PHO5 initiation codon contains the full expression control sequence of the PHO5 gene. The current inventor has cloned this region into a plasmid; the region confers phosphate-dependent regulation to a reporter gene cloned downstream. Alternatively, hybrid expression control sequences may be used in the present invention, wherein the minimal upstream activating sequence of a particular gene may be combined with a promoter sequence from a heterologous gene to regulate transcription of a reporter gene. A wide array of heterologous gene promoters is available in the art. For example, a portion of the PHO5 UAS sequence extending from −405 to −206 relative to the initiation codon is sufficient to confer phosphate-dependent regulation to the TDH3 promoter downstream region, resulting in repression of reporter gene expression in high phosphate and efficient reporter gene expression when cells are grown in low phosphate (See Example 2).

Specific Expression Control Sequences

The PHO5 regulatory system, or regulon, in S. cerevisiae provides a number of advantages for assessing cyclin/CDK activity. First, the in vivo phosphorylation substrate of the PHO80p/PHO85p kinase is known to be PHO4p, a positive transcriptional activator of PHO5 gene transcription. Second, unlike other cyclin/CDK pairs, the PHO80p/PHO85p pair is not required for cell viability, nor does it appear to be required for normal cell cycle control (except in a cln1cln2 mutant background). These properties allow extensive genetic modification of these proteins without adverse effects on yeast viability and growth. Third, cell synchronization is not required in the screening system. Fourth, in yeast cells, mammalian cell cycle regulatory proteins can be introduced and studied in the absence of other mammalian proteins (albeit in the presence of homologous and, potentially, functionally similar yeast proteins). Finally, the ease of plating and genetic selection in yeast make for a simple and economical high-throughput phenotypic screening regimen.

Many of these advantages may also be provided by other yeast cyclin/CDK systems which are encompassed by the current invention. In particular, Kuchin et al., 1995, Proc. Nat'l. Acad. of Sci. 92:4006–10, have demonstrated that the S. cerevisiae SSN8 and SSN3 genes encode, respectively, cyclin and CDK homologs which also interact biochemically as a cyclin/CDK complex. The SSN8p/SSN3p kinase contributes to transcriptional repression of a variety of genes. This and other S. cerevisiae CDKs that regulate the activity of a specific transcription factor can also be used in the current invention. Utilization of different cyclin/CDK systems expands the scope of native and hybrid proteins that can be synthesized and broadens the number of potential targets for screening for anti-cancer and anti-proliferation compounds or lead compounds. In addition to the S. cerevisiae system described, the methods of the present invention may be applied to cyclin/CDK screening systems in S. pombe.

It is appreciated that the method of the current invention can encompass use of expression control sequences native to mammalian genes and other desirable target gene systems. Where mammalian expression control sequences are used, the cell line of the current invention is preferably a mammalian cell line. Various mammalian transcription factors have been shown to be regulated by a cyclin/CDK phosphorylation complex. Expression control sequences responsive to these transcription factors can be operably linked to reporter genes to monitor the activity of a cyclin/CDK complex. For example, the E2F mammalian transcription factors (also referred to as DRTF1) constitute a family of (at least) five related proteins. E2F1 is the best characterized of these and, as a heterodimer with the homologous DP-1 protein, is capable of activating expression control sequences containing E2F binding sites (reviewed in La Thangue, 1994, Current Opinion in Cell Biology 6:443–50). A number of growth regulatory proteins have been shown to associate with E2F. These include Retinoblastoma protein (Rb), p107, cyclin E/CDK2 and cyclin A/CDK2. E2F binds preferentially (both in vitro and in vivo) to the underphosphorylated form of the Rb protein and dissociates when Rb is phosphorylated by cyclin E/CDK2 (Dynlacht et al., 1995). Phosphorylation of Rb in G1 phase by cyclin E/CDK2 allows E2F1 to dissociate, complex with DP-1, bind to an E2F-responsive expression control sequence and activate transcription. Subsequently, cyclin A/CDK2 phosphorylates E2F1 in S phase and abolishes its ability to bind DNA and activate transcription. Since cyclin E/CDK2 is activated prior to DNA synthesis but cyclin A/CDK2 is not activated until S phase, an E2F-regulated expression control sequence will exhibit cell cycle dependent expression. A reporter gene operably linked to such a control sequence will be activated late in G1 phase. This cell cycle dependent transcription can be measured in synchronized cell cultures, such as those synchronized by a double thymidine block. Alternatively, reporter gene expression can be measured in asynchronous cultures where the fraction of cells transcribing the reporter gene will be equivalent to the fraction of the cell cycle in which cyclin E/CDK2 is active prior to the activation of cyclin A/CDK2. Depending on the half-life of the reporter gene product, reporter gene expression in asynchronous cultures will be proportionately less than that measured at the optimal time in synchronous cultures.

To adapt E2F-regulated expression control sequences to use in the methods of the present invention, the assay system can be optimized (1) to be independent of cell cycle regulation and (2) to isolate the effect of a single cyclin/CDK pair. For example, cyclin E and/or E2F1 might be constitutively produced or overexpressed in the cell, generating cell lines in which regulation of the reporter gene promoter is independent of the cell cycle.

Alternatively, the E2F system can be exploited to provide an assay system that confers cyclin/CDK regulated transcription to an expression control sequence that originally exhibits no cyclin/CDK regulation. For example, a cell line can be provided with a reporter gene operably linked to an expression control sequence comprising a promoter and the upstream activation sequence for yeast GAL4p transcription factor. Such expression control systems are activated by GAL4p or hybrid mammalian/yeast GAL4p molecules, expressed in mammalian cells. The cells are further provided with a fusion gene encoding a hybrid protein comprising GAL4p DNA binding and transcription activation domains fused to the RB binding domain of E2F1. The modular functions of transcription factors will allow the fusion gene product to retain the RB-mediated regulation of E2F1. That is, phosphorylation of RB by cyclin E/CDK2 will release RB from its interaction with a fusion gene product and allow the GAL4p domains of the fusion gene product to bind the GAL4 UAS. Reporter gene expression is thus rendered dependent on cyclin E/CDK2 phosphorylation of Rb, but expression of the fusion gene is independent of cyclin A/CDK2 mediated phosphorylation of E2F and inactivation. These modifications optimize the E2F/cyclin E/CDK2 regulatory system to allow screening for agents that affect only cyclin E/CDK2-dependent regulatory interactions. Either synchronous or asynchronous cultures may be utilized in this system, depending on the efficiency of E2F mediated reporter gene expression and the stability of the encoded protein. It is appreciated that candidate compounds identified using the E2F embodiment of the invention will be re-examined in secondary experiments, confirming in vitro which cyclin/CDK pair is affected.

It is appreciated that other mammalian transcription factors might also be utilized to place reporter gene expression under control of a specific cyclin/CDK. For example, the recently identified mouse DMP1 is a myb-like transcription factor which activates promoters containing the sequences CCCG(G or T)ATGT. DMP1 binds to cyclin D in vitro and when coexpressed with cyclin D in insect cells and, furthermore, is phosphorylated by cyclin D/CDK4 under these conditions (Hirai and Sherr, 1966, *Mol. Cell. Biol.* 16:6457–6467). If the ability of DMP1 to activate promoters is dependent on its phosphorylation state, then expression of reporter genes containing DMP1 binding sites in the promoter may be used as an indirect measurement of cyclin D/CDK4 function.

Hybrid Genes

The invention can be practiced with hybrid gene products in order to achieve certain advantages. The hybrid genes used with the current invention comprise a first coding region and a second coding region from different sources (discussed below) that are operably linked together. The first coding region is derived from a first gene that is native, or endogenous, to the cell line being used in the screen and which affects phosphorylation by the cyclin/CDK phosphorylation system that regulates transcription of the reporter gene in the cell line. To determine whether the first gene affects phosphorylation by the particular cyclin/CDK system, the chromosomal copy of the first gene can be mutated or disrupted and expression of the reporter gene analyzed using techniques well known in the art (Kaiser et al., 1994, In Methods in Yeast Genetics, Cold Spring Harbor Laboratories Press). Changes in transcriptional regulation of the reporter gene indicate that the normal version of the first gene is a necessary component in transcriptional control. Additionally, the wild-type version of the first gene can be overexpressed, or a mutated version of the gene can be expressed extrachromosomally in the cell, using methods well known in the art, to determine whether the first, native gene influences expression of the reporter gene. Preferably, the first gene has sequence homology to at least one gene known to be involved in cell cycle regulation. More preferably, the first gene encodes a protein selected from the group consisting of cyclins, CDKs and cyclin kinase inhibitors.

The second coding region of a hybrid gene of the current invention is from a second, non-native, target (often mammalian) gene, wherein the target gene displays homology to the first gene. The coding regions from the first and second genes are chosen according to information available in the art, preserving the portions of the first gene that are required to exert its regulation over expression of the reporter gene. For example, genes encoding hybrids between yeast CDC28p and PHO85p have been constructed, providing preliminary data regarding residues of PHO85p that are required to retain PHO85p specific kinase function in a yeast hybrid protein (Santos et al., 1995). Furthermore, crystal structure determination of the human cyclin A/CDK2 complex has identified regions of interaction between human cyclin A and CDK2 (Jeffrey et al., 1995, *Nature* 376:313–20).

The binding of cyclin A alters the structure of free CDK2 in several ways expected to confer enzymic activity. First the T loop (residues 146 to 166) moves away from the catalytic cleft allowing substrate proteins to bind. In this conformation, Thr 160 is also more accessible, and it is known that phosphorylation of this residue by CAK is required for CDK activity. The structure of amino acids in the catalytic site (Arg 33, Glu 51, Asp 145) is altered by cyclin A binding such that the β-γ bond of ATP is moved into a position favorable for nucleophilic attack from a bound substrate protein. The structure determination by Jeffrey et al. (1995) also reveals the regions of contact between human cyclin A and CDK2. The cyclin makes primary contact to the PSTAIRE region of CDK2 and also binds to the T loop region. The differences between the crystal structure of the cyclin A/CDK2 complex and that previously determined for free CDK2 illustrates the conformational changes in the CDK induced upon cyclin binding which confer catalytic activity to the complex. The structure of human cyclin A/CDK2 complexed with the N-terminal inhibitory domain of the CKI, p27$^{Kip1}$, has also been determined (Russo, A. A., et al., 1996, *Nature* 382:325–331). On cyclin A, it binds in a groove formed by the conserved cyclin box residues, while on CDK2 it binds to the amino terminal lobe and catalytic cleft, suggesting that it may compete with ATP for binding.

Although these structural results are limited to human cyclin A/CDK2 and p27$^{Kip1}$, the highly conserved amino acid sequence of CDKs and the (more limited) sequence homology of cyclins suggest that the major structural features observed in the above analyses may be conserved in other cyclin/CDK complexes. Thus, these results may be utilized in the design of hybrid cyclins, CDKs or CKIs where retention or deletion of certain properties is desired.

The choice of this second, target gene is also informed by knowledge in the art regarding key cyclin/CDK related proteins associated with cancer and other proliferative disorders. The second, target gene of this invention is homologous to the first gene, thus the target gene preferably is or has sequence homology to a gene known to be involved in cell cycle regulation. More preferably, the second, target gene encodes a protein selected from the group consisting of cyclins, CDKs and cyclin kinase inhibitors. Most preferably, the target is a mammalian gene and is cyclin A, cyclin E, a human D-type cyclin, CDK2, CDK4, CDK6, p16$^{INK4a}$, p21 or p27.

The general strategy for constructing functional hybrid genes of the current invention is as follows. A hybrid gene is constructed to include a region of a first, native gene that is deduced, based on structural and functional studies and assays available in the art, to be necessary for transcriptional control of the expression control sequences linked to the reporter gene. The hybrid gene is expressed in a cell line harboring a reporter gene construct, where the chromosomal copy of the first, native gene is mutant or disrupted. Reporter gene expression is examined to determine whether the hybrid gene product has functionally substituted for the first gene to effect normal regulation of reporter gene expression. If the hybrid gene product properly regulates reporter gene transcription, it can further be determined whether the hybrid gene product utilizes the other components (cyclin/CDK/CKI) of the particular assay system or if the hybrid gene uses other homologous genes native to the cell line. If the hybrid gene product does not properly regulate transcription of the reporter gene, the hybrid gene can be expressed in the same yeast strain together with cDNAs encoding the cyclin/CDK/CKI components that natively associate with the target gene. If the hybrid, e.g., mammalian/yeast, gene, in conjunction with native mammalian components, reinstates normal transcriptional regulation of the reporter gene, the resulting phosphorylating system can be used according to the present invention.

Hybrid CDK proteins have previously been constructed between two homologous yeast CDKs, PHO85 and CDC28 (Santos et al., 1995, *Mol. Cell. Biol.* 15:5482–91). Analyses of these hybrids determined that the critical regions of PHO85p required to retain transcription regulation function are residues 155 to 254. The current invention capitalizes on the new demonstration that a target/host, e.g., mammalian/yeast, hybrid protein can substitute for the function of an endogenous gene involved in cyclin/CDK regulation. Preferably, the hybrid gene has sequence homology to genes known to be involved in cell cycle regulation. More preferably, the hybrid gene encodes a hybrid protein homologous to proteins selected from the group consisting of cyclins, CDKs and cyclin kinase inhibitors.

In one particularly preferred embodiment, the first, native gene is PHO85 and the corresponding first coding region used in the hybrid gene encodes amino acids 155 to 302 of PHO85; and the second, target gene is human CDK2 and the corresponding second coding region used in the hybrid gene encodes amino acids 1 to 151 of human CDK2 (CK2-P85#1). In another embodiment, the hybrid gene is comprised of a first coding region encoding amino acids 155 to 251 from PHO85, a second coding region encoding amino acids 1 to 151 from human CDK2, and a third coding region encoding amino acids 256–298 of CDK2 (CK2-P85#2). The particular coding regions are joined in a relative order consistent with their native positions within their respective genes, forming the hybrid genes depicted in FIG. 2. The structure of the hybrid CDKs constructed are depicted with regions derived from human CDK2 depicted as solid bars and regions derived from PHO85p represented as open bars. The amino acid position, from the native protein sequences, at the amino and carboxyl ends of each region of the hybrids is indicated.

In constructing hybrid CDKs, convenient restriction sites in the PHO85 gene can be employed. Examples are HindIII, which cleaves at codon 9 in the amino terminus; BglII, which cleaves at codon 51, just on the carboxy end of the PSTAIRE motif; and EcoRI, which cleaves at codon 80 between the amino and carboxyl lobes of the CDK. Alternatively, genes encoding specific hybrid mammalian/yeast or other target/host CDKs can be assembled using two-step PCR procedures utilizing appropriately designed primers, as is demonstrated in Example 4.

Minimally, the hybrid gene is comprised of one region of the first, native gene and one region of the second, target gene. However, it is well appreciated that the hybrid gene can contain numerous discontinuous regions of each of the first and second gene. Using recombinant DNA technology well known in the art, selected regions of the protein may be identified which retain the sequences of the first gene necessary to preserve transcription regulatory function, while all remaining sequences can be replaced by sequences from a homologous target mammalian gene.

It is appreciated that hCDK2 is a cell cycle regulation protein that is capable of alternately forming complexes with cyclin E or cyclin A. A number of cancers have been identified in which mutations in p53 or failure to produce functional p21 alters regulation the cyclin E/CDK2 complex (reviewed in Hunter and Pines, 1994; Sherr, 1996). By manipulating a cell line of the current invention such that reporter gene expression is jointly dependent on cyclin E sequences and CDK2 sequences, agents that inhibit cyclin E/CDK2 function, such as p21 mimetics, can be identified. Similarly, several cancers are associated with defects in cyclin A, which affects cell cycle regulation through the cyclin A/CDK2 complex. Manipulation of a yeast cell strain such that reporter gene expression is jointly dependent on cyclin A sequences and CDK2 allows identification of inhibitors of the cyclin A/CDK2 complex.

The human CKI and tumor suppressor p16$^{INK4a}$ is mutated or deleted in a variety of tumor cell lines and primary tumors. The suppressor p16$^{INK4a}$ inhibits CDK4, and compounds that mimic the effect of p16$^{INK4a}$ may be useful cancer therapeutic agents. Suppressor p16$^{INK4a}$ exhibits significant homology to the yeast CKI PHO81p in an ankyrin repeat domain. The observation that the PHO81p ankyrin domain alone (amino acids 584 to 724) is capable of inhibiting PHO80p/PHO85p in vivo (Ogawa et al., 1995, *Mol. Cell. Biol.* 15:997–1004) indicates that a hybrid CKI gene including the PHO81p ankyrin domain can retain the functions necessary for appropriate transcriptional regulation of the PHO5 expression control sequences. In one embodiment of the invention, the native p16$^{INK4a}$ protein may functionally replace the PHO81p CKI. In another aspect of the current invention, the hybrid gene is a CKI, where the first, native gene is PHO81 and the second, target gene is p16$^{INK4a}$. In an alternative embodiment the ankyrin repeat domain of PHO81 is used in the hybrid gene. The functional hybrid gene is identified by its ability to inhibit the PHO80p/PHO85p phosphorylation of PHO4p transcription factor. Because phosphorylation leads to transcriptional repression, a pho81 disruption strain represses transcription in both high and low phosphate. A functional hybrid CKI gene restores this strain's ability to derepress transcription.

Mutations in CDK4 have also been correlated with cancer. For example, human melanomas have been demonstrated to have CDK4 missense mutations that render the CDK non-responsive to CKI p16$^{INK4a}$. In another embodiment of the invention, the hybrid gene is a CDK, where the first gene is PHO85p and the second gene is CDK4. Functional hybrids can be identified by the ability to confer PHO5 promoter repression in high phosphate in a pho85 mutant host.

In another embodiment of the invention, a mutation or deletion can be introduced in a hybrid gene, where the hybrid gene in the absence of the mutation provides a gene product effective to permit normal phosphorylation control of reporter gene transcription. Example 4 illustrates such a mutation, CK2-P85m1, which has a single-codon deletion in the hybrid gene CK2-85#1. The hybrid gene mutation or deletion preferably corresponds to a mutation associated with a disease state. Use of the mutated hybrid gene in the screens of the current invention allows targeted screening for agents that overcome specific mutations in cell cycle regulatory proteins. For example, the assay system using a PHO85p/CDK4p hybrid gene can be used to screen for compounds which restore p16$^{INK4a}$ responsiveness to mutant CDK4. Alternatively, novel inhibitors of the mutant CDK4 can be identified, which would be useful therapeutically to treat these melanomas.

A preferred embodiment of the current invention allows measurement of the activity of hybrid mammalian/yeast proteins. It is appreciated, however, that native human cell cycle regulatory proteins can in some cases substitute for the first, native gene product that affects cyclin/CDK mediated transcriptional regulation of the reporter gene. This substitution, or complementation, can easily be tested using the same assay methods as described for testing hybrid genes. That is, the chromosomal copy of the first, native gene is disrupted, and the human cell cycle regulatory gene is expressed in a cell that harbors a reporter gene construct that is transcriptionally regulated by the first, native gene. Control of expression of the reporter gene can be analyzed to determine whether the human gene can complement a mutation in the first gene.

The hybrid and native mammalian genes of the current invention can be expressed from DNA incorporated into the chromosome. However, more preferably, these genes are expressed extrachromosomally, preferably from a plasmid. Whether present as chromosomal or extrachromosomal DNA, the hybrid and native mammalian genes are preferably expressed from expression control sequences that are derived from the first, native gene, which is complemented by the hybrid or full-length mammalian gene. In one embodiment of the invention, use of expression control sequences from the first, native gene, which is homologous to the hybrid or full-length mammalian gene, allows expression of hybrid and full-length mammalian genes at the levels and times similar to the native expression for the cyclin/CDK phosphorylation system being utilized. For example, when the first gene is PHO85, a hybrid or full-length mammalian gene is preferably expressed from PHO85 gene expression control sequences. In another embodiment, expression vectors are used which allow high-level constitutive expression of the hybrid or full-length mammalian gene; an especially preferred vector is pBT6, which uses the efficient TDH3 gene promoter. Expression vectors facilitating cloning and expression from appropriate expression control sequences are provided in the current invention and explained in detail in Example 3. These vectors are useful when the PHO5 controlling cyclin/CDK regulon is utilized; the vectors contain expression control sequences from PHO85 (pBT16), PHO80 (pBT15) and PHO81 (pBT17) and are provided for expression, respectively, of CDKs, cyclins and CKIs.

Chromosomal Disruptions

In several embodiments of the invention, a cell line can be manipulated to mutate or otherwise disrupt chromosomal genes. For example, when hybrid or full-length mammalian genes are assayed for whether they confer the transcription regulatory function of the first gene, the assays can be performed with haploid cells in which the chromosomal copy of the first gene is mutant or disrupted. Similarly, when a first, native gene is substituted for by a hybrid or full-length mammalian gene, the cell line is most preferably made mutant for the first, native gene. Genetic and molecular techniques for targeting chromosomal genes for disruption or mutation are well known in the art (Kaiser et al., 1994, Methods in Yeast Genetics, Cold Spring Harbor Laboratory Press; Nakayama et al., 1993, *Science* 261:1584–1588). Mutant strains display the expected phenotype as explained herein. For example, a pho81 disruption strain fails to derepress reporter gene expression in low phosphate, and a pho85 and/or pho80 disruption strain fails to repress reporter gene expression in high phosphate. Phenotypic indications that the desired gene was disrupted are to be confirmed by molecular analysis.

Positive Selections

The components of the current invention as described above provide an assay system that allows for selective growth, or positive selection, of cells exhibiting the desired cyclin/CDK transcriptional control. In one embodiment of the invention, cells with an intact, functional cyclin/CDK complex are used to select for agents that impair the functional cyclin/CDK activity. In another embodiment, cells with functional cyclin/CDK/CKI regulons are used to select for agents that impair the functional CKI activity. Another embodiment allows selection for cells having mutations in cyclin or CDK that disrupt the normal regulation of phosphorylation by the complex. Example 7 details two positive selection regimens encompassed by the current invention.

Assays involving selection rather than screening afford the ability to assay the effects of a large number of candidate agents. Candidate agents can be from any source, such as small molecule chemical libraries, combinatorial libraries, cDNA libraries, random peptide libraries, and random RNA libraries. In the case of DNA encoded products (e.g. cDNA libraries), selections allow the purification (cloning), from a complex mixture, of DNA encoding the molecule with the desired biological activity. Such libraries and methods of preparing them are available in the art (Freier et al., 1995, *J. Medicinal Chem.* 38: 344–52). Cell growth can be measured by visual inspection, by spectrophotometric analysis of cell density of liquid cultures, or by plating for single colonies on the appropriate selective plates. Preferably, sources for agents tested in selection regimens include cDNA libraries, random peptide libraries, and random RNA libraries.

Screens

As described above, multiple embodiments of the current invention utilize reporter genes whose gene products can be readily detected. Preferably, the screens of the current invention utilize reporter genes whose gene products are detectable by a spectrophotometric or colorimetric assay, such as genes encoding β-galactosidase, green fluorescent protein, luciferase and CAT. It is appreciated that these reporter genes allow rapid, automated screening of a wide range of candidate agents. As with the selection regimens described above, sources of candidate agents include extracts from natural sources, synthetic compounds, small molecule chemical libraries, combinatorial libraries, cDNA libraries, random peptide libraries, and random RNA libraries. Preferably, small molecule libraries and combinatorial libraries are applied to the screens of the current invention. Additionally, products of rational design programs can be assayed for activity in these screens.

The percentage of pharmacologically active compounds identified in a cell-based screen can be increased by maximizing cellular uptake and retention of test compounds. In one embodiment of the invention, the screening cell line's ability to import and/or retain test compounds is enhanced by altering one or more of the genes involved in transporting molecules across the plasma membrane, thus causing increased or decreased activity or levels of transport proteins. In eukaryotes, polar molecules are transported by membrane proteins which are generally classified within three categories: channels, facilitators (also termed permeases, carriers or transporters) and pumps. Of the transport proteins identified to date, most mediate uptake of solutes across the plasma membrane, while others catalyze transport of molecules from the cytoplasm into the extracellular medium.

Many species, from bacteria to humans, demonstrate acquired resistance to cytotoxic compounds, and this resistance appears to be mediated by proteins from either the facilitators superfamily (Marger and Saier, 1993, *Trends Biochem. Sci.* 18:13–20) or the ATP binding cassette (ABC) transporters family, a group of nonproton ATPases in the pump class (reviewed in Higgins, 1992, *Ann. Rev. Cell Biol.* 8:67–113). For example, tumor cells that acquire resistance to a variety of chemotherapeutic agents display the multidrug resistance (MDR) phenotype, which is due to overexpression of the mammalian P-glycoprotein, an ABC transporter that pumps drugs out of the cell (reviewed in Endicott and Ling, 1991, *Ann. Rev. Biochem.* 58:137–171). The *S. cerevisiae* pleiotropic drug resistance (PDR) phenotype (reviewed in Balzi and Goffeau, 1995, *J. Bioenerg. Biomembr.* 27:71–76) is similar to mammalian cell MDR and is caused by overexpression of the PDR5, SNQ2 and YOR1 genes (Balsi et al., 1994, *J. Biol. Chem.* 269:2206–2214; Decottingies et al., 1995, *J. Biol. Chem.* 270:18150–18157; Katzmann et al., 1995, *Mol. Cell. Biol.* 15:6875–6883). These three genes encode ABC transporters that are yeast homologs of the mammalian P-glycoprotein. Since each of the three proteins transports a different class of compounds out of the yeast cell, inactivation of these genes increases the intracellular concentrations of the compounds. Because transcription factors PDR1p and PDR3p are required for expression of the PDR5, SNQ2 and YOR1 genes (Balzi et al., 1987, *J. Biol. Chem.* 262:16871–16879; Delaveau et al., 1994, *Mol. Gen. Genet.* 244:501–511), inactivation of the yeast PDR1 and/or PDR3 genes decreases the levels of the PDR5p, SNQ2p, YOR1p proteins (and possibly other ABC transporters). By altering expression of these and other genes involved in transport, either individually or in various combinations, strains optimized for screening libraries of particular chemical classes of compounds may be generated.

Secondary Screening

Agents that demonstrate activity in a screening or selection assay of the current invention are subjected to secondary screens to confirm activity and specificity. For example, compounds identified as inhibitors of a cyclin and a hybrid CDK2/PHO85p complex are tested in a secondary screen using the native yeast PHO80p/PHO85p system. This secondary screen distinguishes compounds that are specific to the human CDK2 epitopes from those targeted to both CDK2 and PHO85p or specifically to PHO85p epitopes. Secondary screening may also be useful, when necessary, to demonstrate that the agent acts through the cyclin/CDK complex and does not exert a direct effect on the transcription factor(s) in the assay. Experimental techniques used to conduct secondary testing utilize similar techniques as those described above and will be apparent to those of ordinary skill in the art.

There are a number of specific embodiments of the invention that will be understood by those skilled in the art to be possible based on the disclosure set out above and in the examples below. A number of specific embodiments are set out immediately below along with a number of variations. For example, the invention includes a method of screening for a compound that affects mammalian cell cycle regulatory proteins, comprising administering a compound to a cell line, wherein the cell line comprises genetic information comprising a reporter gene operably linked to a gene expression control sequence, wherein the gene expression control sequence comprises an Upstream Activation Sequence and a promoter, and the Upstream Activation Sequence comprises a DNA region that binds to a transcription control factor that is regulated through phosphorylation by a cyclin/CDK phosphorylation system; and an effector gene providing a gene product effective to permit normal cyclin/CDK regulation of the transcription control factor; and analyzing expression of the reporter gene in the cell line, thereby determining whether the compound affects the normal regulation.

Another method of the invention is a method of identifying a gene that affects mammalian cell cycle regulatory proteins, comprising providing a cell line that comprises genetic information comprising a reporter gene operably linked to a gene expression control sequence, wherein the gene expression control sequence comprises an Upstream Activation Sequence and a promoter, and the Upstream Activation Sequence comprises a DNA region that binds to a transcription control factor that is regulated through phosphorylation by a cyclin/CDK phosphorylation system; and an effector gene providing a gene product effective to permit normal cyclin/CDK regulation of the transcription control factor; introducing into the cell line expression of an exogenous gene; and analyzing expression of the reporter gene, thereby determining whether the exogenous gene affects the normal regulation.

An alternative embodiment of the invention is a method of identifying a gene that affects mammalian cell cycle regulatory proteins, comprising providing a cell line that comprises genetic information comprising a reporter gene operably linked to a gene expression control sequence, wherein the gene expression control sequence comprises an Upstream Activation Sequence and a promoter, and the Upstream Activation Sequence comprises a DNA region that binds to a transcription control factor that is regulated through phosphorylation by a cyclin/CDK phosphorylation system; and an effector gene providing a gene product effective to permit normal cyclin/CDK regulation of the transcription control factor; introducing a mutation in a chromosomal test gene; and analyzing expression of the reporter gene, thereby determining whether the test gene affects the normal regulation.

Variations of the methods described above include those in which the effector gene is a hybrid gene comprising a first coding region from a gene native to the cell line and a second coding region from a second gene, wherein the native gene encodes a gene product that affects phosphorylation by the cyclin/CDK phosphorylation system, and the second gene is mammalian and is homologous to the native gene; the cell line further comprises a chromosomal mutation in the native gene; the effector gene is a mammalian gene; the mammalian gene is homologous to a native gene; the mammalian gene is a cyclin-dependent kinase; the mammalian gene encodes hCDK2; the mammalian gene encodes the amino terminus of hCDK2.

The invention also includes a method of screening for a compound that affects mammalian cell cycle regulatory proteins, comprising administering a compound to a cell line, wherein the cell line comprises genetic information comprising a reporter gene operably linked to a gene expression control sequence, wherein the gene expression control sequence comprises an upstream activation sequence and a promoter, and the upstream activation sequence comprises a DNA region that binds to a transcription control factor that is regulated, directly or indirectly, through phosphorylation by a cyclin/CDK phosphorylation system; and a hybrid gene comprising a first coding region from a gene native to the cell line and a second coding region from a second target gene, wherein the native gene encodes a gene product that is involved in phosphorylation by the cyclin/CDK phosphorylation system, and the second gene is mammalian and is homologous to the native gene, and the hybrid gene provides a gene product effective to permit normal cyclin/CDK regulation of the transcription control factor; and analyzing expression of the reporter gene in the cell line, thereby determining whether the compound affects the normal regulation.

Also part of the invention is a cell line comprising genetic information comprising a reporter gene operably linked to a gene expression control sequence, wherein the gene expression control sequence comprises an upstream activation sequence and a promoter, and the upstream activation sequence comprises a DNA region that binds to a transcription control factor that is regulated, directly or indirectly, through phosphorylation by a cyclin/CDK phosphorylation system; and a hybrid gene comprising a first coding region from a gene native to the cell line and a second coding region from a second gene, wherein the native gene encodes a gene product that affects phosphorylation by the cyclin/CDK phosphorylation system, and the second gene is mammalian and is homologous to the native gene, and the hybrid gene provides a gene product effective to permit normal cyclin/CDK regulation of the transcription control factor.

A different method of the invention provides a method of identifying a gene that affects mammalian cell cycle regulatory proteins, comprising providing a cell line that comprises genetic information comprising a reporter gene operably linked to a gene expression control sequence, wherein the gene expression control sequence comprises an upstream activation sequence and a promoter, and the upstream activation sequence comprises a DNA region that binds to a transcription control factor that is regulated, directly or indirectly, through phosphorylation by a cyclin/CDK phosphorylation system; and a hybrid gene comprising a first coding region from a gene native to the cell line and a second coding region from a second gene, wherein the native gene encodes a gene product that affects phosphorylation by the cyclin/CDK phosphorylation system, and the second gene is mammalian and is homologous to the native gene, and the hybrid gene provides a gene product effective to permit normal cyclin/CDK regulation of the transcription control factor; and introducing into the cell line expression of an exogenous gene; analyzing expression of the reporter gene, thereby determining whether the exogenous gene affects the normal regulation.

Screening tests of the invention include a method of identifying a gene that affects mammalian cell cycle regulatory proteins, comprising providing a cell line that comprises genetic information comprising a reporter gene operably linked to a gene expression control sequence, wherein the gene expression control sequence comprises an upstream activation sequence and a promoter, and the upstream activation sequence comprises a DNA region that binds to a transcription control factor that is regulated, directly or indirectly, through phosphorylation by a cyclin/CDK phosphorylation system; and a hybrid gene comprising a first coding region from a gene native to the cell line and a second coding region from a second gene, wherein the native gene encodes a gene product that affects phosphorylation by the cyclin/CDK phosphorylation system, and the second gene is mammalian and is homologous to the native gene, and the hybrid gene provides a gene product effective to permit normal cyclin/CDK regulation of the transcription control factor; and introducing a mutation in a chromosomal test gene; analyzing expression of the reporter gene, thereby determining whether the test gene affects the normal regulation.

Other screening methods include a method of screening for a compound that inhibits mammalian CDKs, comprising administering a compound to a cell line, wherein the cell line comprises genetic information comprising a reporter gene, wherein expression of the reporter gene confers to the cell line the ability to grow in certain media; the reporter gene is operably linked to a gene expression control sequence, wherein the gene expression control sequence comprises an upstream activation sequence and a promoter, and the upstream activation sequence is from the PHO5 gene, wherein the gene expression control sequence is transcriptionally regulated by a cyclin/CDK phosphorylation system; and a hybrid gene comprising a first coding region from a gene native to the cell line and a second coding region from a second gene, wherein the native gene affects regulation by the cyclin/CDK phosphorylation system, and the second gene is mammalian and is homologous to the native gene, and the hybrid gene provides a gene product effective to permit normal cyclin/CDK regulation of the transcription control factor; and growing cells under conditions that select for cells that inappropriately express the reporter gene, thereby identifying compounds that inhibit the CDK from normally repressing transcription from the PHO5 expression control sequence.

Variations of the above-described methods and cell line, as well as other embodiments of the invention involving hybrid genes, include those in which the hybrid gene is expressed from a plasmid; the hybrid gene is a cyclin-dependent kinase; the native gene is PHO85; the second gene is hCDK2; the chromosomal PHO85 gene is non-functional; the hybrid gene is selected from the group consisting of CK2-P85#1, CK2-P85#2, CK2-P85m1, CK2-P85ΔC and CK4-P85#1; the cell line has a chromosomal mutation in the native gene; the hybrid gene is expressed from a PHO85 promoter; the hybrid gene is expressed from the plasmid expression vector pBT1, pBT6, pYES2 or pBT16; the hybrid gene encodes a hybrid cyclin; the native gene is PHO80; the second gene is human cyclin A; the second gene is human cyclin E; the second gene is a human D-type cyclin; the chromosomal PHO80 gene is non-functional; the hybrid gene is expressed from a PHO80 promoter; the hybrid gene is expressed from the plasmid expression vector pBT1, pBT6, pYES2 or pBT15; the hybrid gene encodes a hybrid cyclin kinase inhibitor; the native gene is PHO81; the second gene encodes a protein selected from the group consisting of p15, p16, p18, p19, p21, p27 and p57; the chromosomal PHO81 gene is non-functional; the hybrid gene is expressed from a PHO81 promoter; the hybrid gene is expressed from the plasmid expression vector pBT1, pBT6, pYES2 or pBT17; and the second coding region harbors a mutation.

The invention also includes a method of screening for a compound that affects mammalian cell cycle regulatory proteins, comprising administering a compound to a cell line, wherein the cell line comprises genetic information comprising a reporter gene operably linked to a gene expression control sequence, wherein the gene expression control sequence comprises an upstream activation sequence and a promoter, and the upstream activation sequence comprises a DNA region that binds to a transcription control factor that is regulated, directly or indirectly, through phosphorylation by a cyclin/CDK phosphorylation system; and a mammalian gene homologous to a gene native to the cell line, wherein the native gene affects the regulation by the cyclin/CDK phosphorylation system and the mammalian gene is effective to permit normal phosphorylation control of the transcription factor; and analyzing expression of the reporter gene in the cell line, thereby determining whether the compound affects the normal regulation.

Also part of the invention is a cell line comprising genetic information comprising a reporter gene operably linked to a gene expression control sequence, wherein the gene expression control sequence comprises an upstream activation sequence and a promoter, and the upstream activation sequence comprises a DNA region that binds to a transcription control factor that is regulated, directly or indirectly, through phosphorylation by a cyclin/CDK phosphorylation system; and a mammalian gene homologous to a gene native to the cell line, wherein the native gene affects the regulation by the cyclin/CDK phosphorylation system and the mammalian gene is effective to permit normal phosphorylation control of the transcription factor.

A different method of the invention provides a method of identifying a gene that affects mammalian cell cycle regulatory proteins, comprising providing a cell line that comprises genetic information comprising a reporter gene operably linked to a gene expression control sequence, wherein the gene expression control sequence comprises an upstream activation sequence and a promoter, and the upstream activation sequence comprises a DNA region that binds to a transcription control factor that is regulated, directly or indirectly, through phosphorylation by a cyclin/CDK phosphorylation system; and a mammalian gene homologous to a gene native to the cell line, wherein the native gene affects the regulation by the cyclin/CDK phosphorylation system and the mammalian gene is effective to permit normal phosphorylation control of the transcription factor; and introducing into the cell line expression of an exogenous gene; analyzing expression of the reporter gene, thereby determining whether the exogenous gene affects the normal regulation.

Screening tests of the invention include a method of identifying a gene that affects mammalian cell cycle regulatory proteins, comprising providing a cell line that comprises genetic information comprising a reporter gene operably linked to a gene expression control sequence, wherein the gene expression control sequence comprises an upstream activation sequence and a promoter, and the upstream activation sequence comprises a DNA region that binds to a transcription control factor that is regulated, directly or indirectly, through phosphorylation by a cyclin/CDK phosphorylation system; and a mammalian gene homologous to a gene native to the cell line, wherein the native gene affects the regulation by the cyclin/CDK phosphorylation system and the mammalian gene is effective to permit normal phosphorylation control of the transcription factor; and introducing a mutation in a chromosomal test gene; analyzing expression of the reporter gene, thereby determining whether the test gene affects the normal regulation.

Variations on all of the above-described methods, cell lines, and screening tests include those in which the gene expression control sequence comprises sequences native to the cell line; the reporter gene is selected from the group consisting of $E.$ $coli$ β-galactosidase, $E.$ $coli$ tn5 neo, the $S.$ $cerevisiae$ genes LEU2, URA3, HIS3, LYS2, $A.$ $Victoria$ green fluorescent protein gene, the $P.$ $pyradis$ luciferase gene and chloramphenicol-acetyl transferase gene; the host cell has a chromosomal mutation in the native gene; the host cell line is a yeast cell line; the host cell line is a strain of $Saccharomyces$ $cerevisiae$; the cell line has a genetic alteration impairing export of molecules from the cell; the cell line has a genetic alteration enhancing transport of molecules into the cell; the cell line is a yeast cell line with a chromosomal mutation in the PDR5, SN22, YOR1, PDR1 or PDR3 genes; the expression control sequence is from the PHO5 gene of $S.$ $cerevisiae$; the upstream activation sequence is from the PHO5 gene of $S.$ $cerevisiae$; the CDK is PHO85; the chromosomal PHO85 gene is non-functional; the cell line is a mammalian cell line; the transcription control factor is selected from the group consisting of the E2F family of mammalian transcription factors; the CDK is CDK2; and selecting for strains that express or fail to express the reporter gene.

A compound or gene affecting mammalian cell cycle regulatory proteins that is obtained by a method described above is also an embodiment of the invention.

The invention now being generally described, the same will be better understood by reference to the following detailed examples, which are provided for the purpose of illustration only and are not to be considered limiting of the invention unless otherwise specified.

EXAMPLES

Example 1

CELL LINES, PLASMIDS, GENES AND EXPRESSION VECTORS

Strains and Culture Media. Constructed plasmids were cloned in $E.$ $coli$ HB101 or DH5α, using ampicillin selection on LB plates. $Saccharomyces$ $cerevisiae$ strains used in these examples are CM-1 (MATα pep4-3 trp1Δ ura3; Bitter et al., 1991, $Mol.$ $Gen.$ $Genet.$ 231:22–32), YPH499 (MAT a ura3-52 lys2-801 ade2-101 trp1-Δ63 his3-Δ200 leu2-Δ1; Sikorski and Hieter, 1989, $Genetics$ 122:19–27) and YPH500 (MAT α ura3-52 lys2-801 ade2-101 trp1-Δ63 his3-Δ200 leu2-Δ1; Sikorski and Hieter, 1989). Selective yeast media is SD (0.67% yeast nitrogen base without amino acids, 2% dextrose) containing the appropriate nutritional supplements. Plasmids pBT1, pBT3 and pBT5 contain a URA3 selectable marker while plasmids pBT11, pBT12 and pBT13 include a TRP1 selectable marker gene (below). Yeast were transformed by the lithium acetate procedure (Ito et al., 1983, *J. Bacteriol.* 153:163–168). Low and high phosphate media were prepared as follows. Phosphate was precipitated as $MgNH_4PO_4$ from a 10X stock (1.7% w/v) of yeast nitrogen base without amino acids and without ammonium sulfate (YNB w/o aa and AS) as described by O'Connell and Baker (1992, *Genetics* 132:63–73). Low phosphate media consisted of 0.17% phosphate depleted YNB w/o aa and AS, 0.5% $(NH_4)_2SO_4$, 2% dextrose, any required nutritional supplements and 20 mg/L $KH_2PO_4$. High phosphate media contained, instead, 1500 mg/L $KH_2PO_4$.

Yeast strain YBT1, containing a disruption of the chromosomal PHO85 gene, was constructed as follows. The PHO85 gene was PCR amplified as a ~949 bp fragment (below), restricted and cloned into the BamHI site of pRS405 (Sikorski and Hieter, 1989) to generate the plasmid pRS405/PHO85. The PCR amplified HIS3 gene fragment (below) was digested with BamHI and ligated into the BglII site (codon 49 of the PHO85 gene) in pRS405/PHO85 to generate pRS405/pho85::HIS3. This plasmid was digested with BamHI to release the linear pho85::HIS3 gene disruption fragment and transformed into strain YPH500, selecting for histidine prototropy. Strain YBT1 has the genotype MAT α ura3-52 lys2-801 ade2-101 trp1-Δ63 his3-Δ200 leu2-Δ1 pho85::HIS3.

Yeast strain YBT3, containing a disruption of the chromosomal PHO80 gene, was constructed as follows. The PHO80 gene was PCR amplified as a ~922 bp fragment (below), restricted and cloned into the BamHI site of pRS403ΔC (pRS403 in which the ClaI site was deleted by restriction, end-filling with Taq DNA polymerase, and religation) to generate the plasmid pRS403ΔC/PHO80. The PCR amplified ADE2 gene fragment (below) was digested with ClaI and ligated into the ClaI site (codon 101 of the PHO80 gene) in pRS403ΔC/PHO80 to generate pRS403ΔC/pho80::ADE2. This plasmid was digested with BamHI to release the linear pho80::ADE2 gene disruption fragment and transformed into strain YPH499, selecting for adenine prototropy. Strain YBT3 has the genotype MAT α ura3-52 lys2-801 ade2-101 trp1-Δ63 his3-Δ200 leu2-Δ1 pho80::ADE2.

Yeast strain pdr5::URA3 is an improved cell line which, due to a disruption of the PDR5 gene encoding a yeast homologue of a mammalian multidrug resistance pump protein, has impaired ability to transport certain compounds out of the cell. The PDR5 gene was disrupted as follows. The 5' end of the PDR5 gene was amplified from *S. cerevisiae* S288C DNA using the 5' primer, SEQ ID NO:42 and the 3' primer, SEQ ID NO:43. The 3' end of the PDR5 gene was PCR amplified with the 5' primer, SEQ ID NO:44, and the 3' primer, SEQ ID NO:45. The 5' end of SEQ ID NO:44 is complementary to the 5' end of SEQ ID NO:43. An overlap extension reaction of the two PCR products thus results in a polynucleotide having 260 bp of 5' flanking DNA plus the first four amino acid codons of the PDR5 gene fused to the last 8 amino acid codons of PDR5 plus 253 bp of 3' flanking DNA. Approximately equimolar amounts of each product were mixed and PCR amplified in the presence of terminal 5' primer, SEQ ID NO:42, and terminal 3' primer, SEQ ID NO:45. The predominant PCR overlap extension product was the approximately 582 bp fusion polynucleotide which contains internal XbaI and BglII sites. The fragment was digested with KpnI and HindIII and cloned into pUC19 to generate the pUC19/PDR5 plasmid, which was subsequently digested with XbaI and BglII. Then, the yeast URA3 gene was excised from pBT1 as an approximately 1260 bp XbaI to BglII fragment, gel purified, and cloned between the XbaI and BglII sites within the PDR5 portion of the pUC19/PDR5 plasmid. The pdr5::URA3 gene disruption fragment was excised with KpnI and HindIII and used to transform yeast strain YBT1 containing pBT11/Z, and uracil prototrophs were selected. Disruption of the chromosomal PDR5 gene was confirmed by PCR analysis of chromosomal DNA using appropriate primers.

From the pdr5::URA3 strain, a strain was isolated which was resistant to 5-fluoroorotic acid due to an uncharacterized mutation in ura3. This pdr5::ura3 strain can be used for introduction of plasmids with a URA3 marker gene.

Yeast strain pdr5Δ, which contains a null mutation of the PDR5 gene and lacks the URA3 gene was derived from the pdr5::URA3 strain as follows. The pdr5::URA3 strain was transformed with the 582 bp PDR5 overlap extension product which was excised from pUC19/pdr5 with KpnI and HindIII and selected on plates containing 5-fluoroorotic acid. As a result of homologous recombination, 5-fluoroorotic acid resistant cells have deleted the URA3 gene and flanking PDR5 DNA. Generation of the pdr5Δ null mutation was confirmed by PCR analysis of chromosomal DNA using appropriate primers.

Yeast strain pdr1::URA3 is an improved cell line which, due to a disruption of the PDR1 gene encoding a zinc finger protein required for expression of the PDR5, SNQ2 and YOR1 genes, has impaired ability to transport certain compounds out of the cell. The PDR1 gene was disrupted as follows. The 5' end of the PDR1 gene was amplified from *S. cerevisiae* S288C DNA using 5' primer, SEQ ID NO:46, and 3' primer, SEQ ID NO:47. The 3' end of the PDR1 gene was PCR amplified with the 5' primer, SEQ ID NO:48, and the 3' primer, SEQ ID NO:49. The 5' end of SEQ ID NO:48 is complementary to the 5' end of SEQ ID NO:47. An overlap extension reaction of the two PCR products thus results in a polynucleotide having 273 bp of 5' flanking DNA plus the first seven amino acid codons of the PDR1 gene fused to the last nine codons of PDR1 plus 373 bp of 3' flanking DNA. Approximately equimolar amounts of each product were mixed and PCR amplified in the presence of terminal 5' primer SEQ ID NO:46 and terminal 3' primer SEQ ID NO:49. The predominant PCR overlap extension product was the approximately 730 bp fusion polynucleotide which contains internal XbaI and BglII sites. The fragment was digested with KpnI and HindIII and cloned into pUC19 to generate pUC19/PDR1, which was subsequently digested with XbaI and BglII. Then, the yeast URA3 gene was excised from pBT1 as an approximately 1260 bp XbaI to BglII fragment, gel purified and cloned between the XbaI and BglII sites within the PDR1 portion of the pUC19/PDR1 plasmid. The pdr1::URA3 gene disruption fragment is excised with KpnI and HindIII and used to transform yeast strain YBT1 containing pBT11/Z, and uracil prototrophs were selected. Disruption of the chromosomal PDR1 gene in the resulting pdr1::URA3 strain is confirmed by PCR analysis of chromosomal DNA using appropriate primers.

From the pdr1::URA3 strain, a strain is isolated which is resistant to 5-fluoroorotic acid due to an uncharacterized mutation in ura3. This pdr1::ura3 strain can be used for introduction of plasmids with a URA3 marker gene.

Yeast strain pdr1Δ, which contains a null mutation of the PDR1 gene and lacks the URA3 gene is derived from the pdr1::URA3 strain as follows. The pdr1::URA3 strain is transformed with the 730 bp PDR1 overlap extension product which was excised from pUC19/pdr1 with KpnI and HindIII and selected on plates containing 5-fluoroorotic acid. Homologous recombination gives rise to 5-fluoroorotic acid resistant cells lacking the URA3 gene and flanking PDR1 DNA. Generation of the pdr1Δ null mutation is confirmed by PCR analysis of chromosomal DNA using appropriate primers.

Plasmids, Expression Vectors. The yeast integrative plasmids pRS403 and pRS405 (Sikorski and Hieter, 1989) were purchased from Stratagene, the yeast expression vector pYES2 was purchased from Invitrogen and plasmid pCI-neo was purchased from Promega.

Yeast expression vectors pBT1, pBT3 and pBT5 were constructed from, respectively, pGPD(s), pGPD(ΔGPE) and pGP381 as follows. The parent vectors are identical except for the DNA sequence included in the promoter region (Bitter et al., 1991), and the same assembly strategy was used to generate each of the new expression vectors. The ~666 bp BglII to XbaI fragment, containing most of TRP1 and a portion of ARS1, was replaced with the PCR amplified yeast URA3 gene (below; URA3 promoter on the XbaI side). The ~859 bp BamHI to XbaI fragment of the resulting vectors, containing the PGK terminator region, some of pBR322 and the remaining 5' portion of the TRP1 gene, was replaced with the yeast PGK gene transcription termination region, which was PCR amplified from pGPD(s)/Z (Bitter et al., 1991) as a ~303 bp fragment using the primers, SEQ ID NO:1 and SEQ ID NO:2. The ~599 bp BglII to EcoRI fragment of the resulting vectors was replaced with the yeast ARS1 element, which was PCR amplified as a ~280 bp fragment from pGPD(s)/Z using the primers, SEQ ID NO:3 and SEQ ID NO:4. This final step completed the construction of yeast expression vectors pBT1, pBT3 and pBT5.

Figure 3:
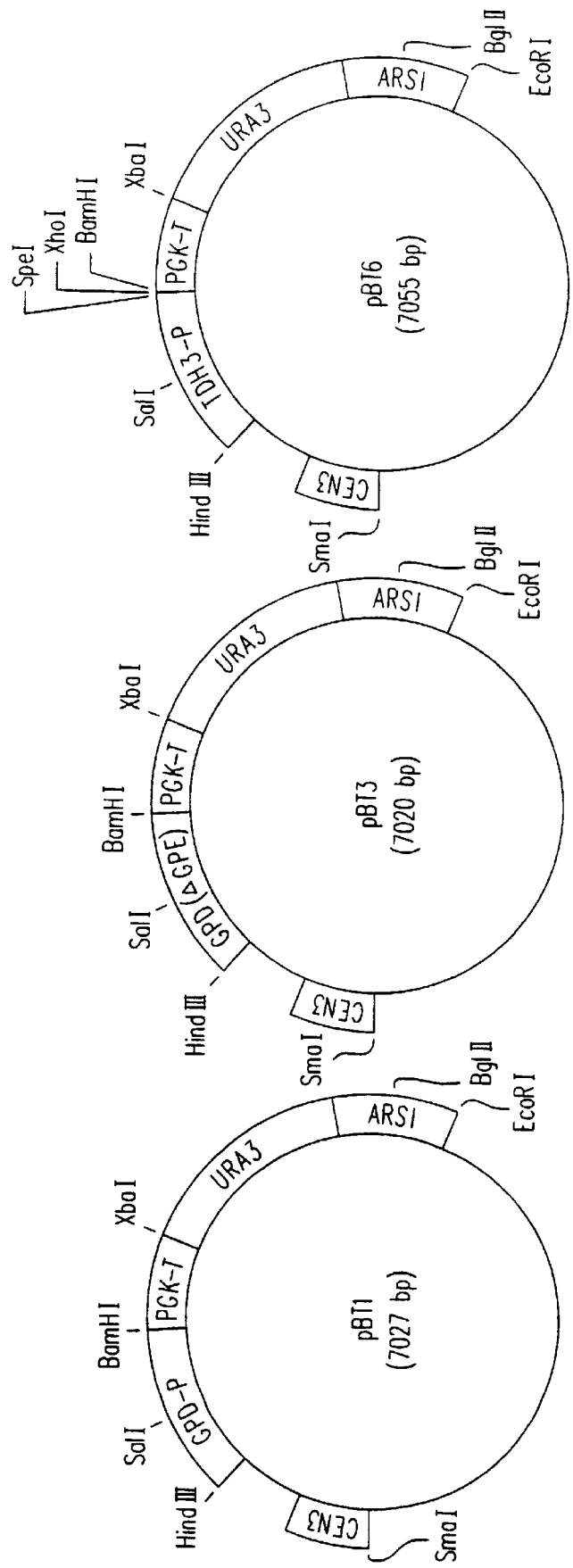
FIG. 3 is a schematic representation of basic expression vectors pBT1, pBT3 and pBT6.

Yeast expression vector pBT6 was constructed from pBT 1 by cloning the oligonucleotide obtained by annealing SEQ ID NO:5 and SEQ ID NO:41, as a BglII to BamHI fragment into the BamHI site and selecting a clone which regenerates the BamHI site adjacent to the PGK terminator region. FIG. 3 depicts several of these expression vectors.

Yeast expression vectors regulated by phosphate concentration were constructed as follows. The ~375 bp KpnI to BamHI promoter fragment of pGP381 was replaced with the PCR amplified PHO5 gene promoter region (below) to generate the vector pBT11. The PCR amplified PHO5 gene transcription termination region (below) was cloned into pBT11, in the correct orientation relative to the promoter, as a BamHI to BglII fragment to generate pBT12. The UAS region from the PHO5 gene promoter was PCR amplified (below) and ligated between the KpnI and SalI sites of pGP381/Z (Bitter et al., 1991) to generate the plasmid pBT13/Z. The PHO5 gene promoter (nucleotides −405 to −10 relative to the translation initiation site) was PCR amplified from S. cerevisiae S288C DNA using the 5' primer, SEQ ID NO:6, and the 3' primer, SEQ ID NO:7. The yeast PHO5 gene promoter UAS (nucleotides −405 to −206) was PCR amplified from S. cerevisiae S288C DNA using the same 5' primer, SEQ ID NO:6, and the 3' primer, SEQ ID NO:8. The yeast PHO5 gene transcription termination region was PCR amplified from S. cerevisiae S288C DNA using the 5' primer, SEQ ID NO:9, and the 3' primer, SEQ ID NO:10.

The following yeast genes, including the promoter regions, were PCR amplified for use as selectable markers on expression vectors or for gene disruptions (above). The URA3 gene (Rose et al., 1984, Gene 29:113–124) coding region plus ~216 bp of 5' and ~77 bp of 3' flanking sequence was PCR amplified from pYES2 with primers which introduced an XbaI site and BglII site at the 5' and 3' ends, respectively. The HIS3 gene coding region plus ~495 bp of 5' and ~138 bp of 3' flanking sequence was PCR amplified from a commercially available expression vector with primers which introduced BamHI sites at the ends. The ADE2 gene coding region (Stotz and Linder, 1990, Gene 95:91–98) plus ~642 bp of 5' and ~128 bp of 3' flanking DNA was PCR amplified from S. cerevisiae S288C DNA with primers which introduced a ClaI site at each end.

The following genes were PCR amplified and ligated into the above expression vectors as follows. The yeast PHO85 gene coding region (Uesono et al., 1987, Nucl. Acids Res. 15:10299–10309), including ~20 bp of 5' and ~20 bp of 3' untranslated region, was PCR amplified from S. cerevisiae S288C genomic DNA (Promega) using the 5' primer, SEQ ID NO:11, and the 3' primer, SEQ ID NO:12. After digestion with BamHI, the fragment was cloned into BamHI restricted pBT1 to generate pBT1/PHO85 (correct orientation relative to promoter) and pBT1/PHO85R (reverse orientation). The native S. cerevisiae PHO85p expressed in these studies corresponds to coding sequence 2 of GenBank Accession #Y00867, X13515 and encodes a 302 amino acid protein. It differs from the 305 amino acid protein encoded by the putative exon containing coding sequence 1 only at the amino terminus (Met Ser Ser Ser Gln Phe Lys Gln Leu . . . in cds1; Met Asn Arg Phe Lys Gln Leu . . . in cds2).

The yeast PHO80 gene coding region (Madden et al., 1988, Nucl. Acids Res. 16:2625–2637), including ~20 bp of 5' and ~18 bp of 3' untranslated region, was PCR amplified from S. cerevisiae S288C genomic DNA using the 5' primer, SEQ ID NO:13, and the 3' SEQ ID NO:14. After digestion with BamHI, the fragment was cloned into BamHI restricted pBT1 to generate pBT1/PHO80 (correct orientation relative to promoter) and pBT1/PHO80R (reverse orientation). The amplified fragment was also cloned into pBT3 to generate pBT3/PHO80 (correct orientation) and pBT3/PHO80R (reverse orientation). Finally, the fragment was also cloned in the correct orientation in the BamHI site of pYES2 to generate pYES2/PHO80.

The E. coli tn5 neo gene coding region, including ~25 bp of 5' flanking and ~23 bp of 3' flanking untranslated region, was PCR amplified from pCI-neo (Promega) using the 5' primer, SEQ ID NO:15, and the 3' primer, SEQ ID NO:16. After digestion with BamHI, the fragment was cloned in the correct orientation into BamHI digested pBT12 to generate pBT12/NEO.

The yeast LEU2 gene coding region (Andreadis et al., 1982, Cell 31:319–325), including approximately 27 bp of 5' and approximately 40 bp of 3' untranslated region, was PCR amplified from S. cerevisiae 288C DNA using the 5' primer, SEQ ID NO:17, and the 3' primer, SEQ ID NO:18. After digestion with BamHI, the fragment was cloned in the correct orientation into BamHI digested pBT12 to generate pBT12/LEU2.

The E. coli LacZ gene was subcloned from pGP171/Z (Bitter et al., 1991) as a BamHI fragment in the correct orientation relative to the promoter in pBT11 to generate pBT11/Z.

Example 2
REGULATED EXPRESSION OF LACZ LINKED TO PHO5 DERIVED PROMOTERS

TABLE II

| Vector | Strain | Units β-Galactosidase | |
|---|---|---|---|
| | | Low Phosphate | High Phosphate |
| pBT11/Z | CM-1 | 288 | 18 |
| pBT11/Z | YPH500 | 175 | 16 |
| pBT13/Z | CM-1 | 292 | 12 |
| pBT13/Z | YPH500 | 161 | 18 |
| pGPD(s)/Z | CM-1 | 384 | 301 |
| PGPD(s)/Z | YPH500 | 188 | 122 |
| pGPD(ΔGPE)/Z | CM-1 | 133 | 104 |
| pGP381/Z | CM-1 | 23 | 30 |
| pGP381/Z | YPH500 | 17 | 18 |

The indicated expression vectors were transformed into strain CM-1 or YPH500 and grown to an $OD_{595}$ of approximately 1.0 in either low or high phosphate medium. Cells were permeabilized and β-galactosidase assayed as described (Bitter et al., 1991). One unit equals an increase of 1 $A_{420}$ divided by the product of (minutes incubated, $OD_{595}$ of the permeabilized cell suspension, and mL of suspension assayed).

Two yeast promoters regulated by inorganic phosphate concentration (Pi) through the action of a cyclin-dependent kinase were assembled in expression vectors (Example 1). FIG. 4A schematically depicts the 5' flanking region of the yeast PHO5 gene. FIG. 4B depicts key features of the plasmid vectors pBT11, pBT12 and pBT13.

The *E. coli* LacZ gene was used as a reporter gene and was inserted into the unique BamHI site of pBT11 or pBT13 (Example 1). The native PHO5 promoter incorporated in pBT 11 is regulated by the $P_i$ concentration in the growth medium, being repressed in high phosphate and induced by phosphate starvation (See Table II). Similarly, the hybrid TDH3($UAS_{PHO5}$) promoter in pBT13/Z is regulated by the phosphate concentration of the growth medium. In low phosphate, the $UAS_{PHO5}$ functions as an enhancer with pBT13/Z yielding 10 times more β-galactosidase activity than the pGP381/Z vector from which it was derived but which has no PHO5 regulatory sequences. Both the pBT11 and pBT13 promoters are repressed in high phosphate and induced by a factor of 10 to 20 when grown in medium containing low phosphate. Such transcriptional regulation by phosphate concentration is not observed for the native TDH3 gene promoter (pGPD(s)/Z) or two TDH3 promoter deletion variants (pGPD(ΔGPE)/Z and pGP381/Z). Under derepressed conditions, the level of β-galactosidase produced from pBT11/Z and pBT13/Z is 75–90% the level produced by the efficient TDH3 gene promoter.

Example 3
REGULATION OF REPORTER GENE EXPRESSION BY PHO85P AND PHO80P

TABLE III

| Strain | Vector(s) | Units β-Galactosidase | |
|---|---|---|---|
| | | Low Phosphate | High Phosphate |
| YPH500 | pGPD(s)/Z | 229 | 135 |
| YPH500 | pBT11/Z | 189 | 16 |
| YBT1 | pBT11/Z | 272 | 152 |
| YBT1 | pBT11/Z, pBT1 | 500 | 259 |
| YBT1 | pBT11/Z, pBT1/PHO85 | 276 | 40 |
| YBT1 | pBT11/Z, pBT1/PHO85R | 315 | 42 |
| YBT3 | pBT11/Z | 300 | 179 |
| YBT3 | pBT11/Z, pBT1/PHO80 | 14 | 17 |
| YBT3 | pBT11/Z, pBT1/PHO80R | 244 | 23 |
| YBT3 | pBT11/Z, pBT3/PHO80 | 15 | 14 |
| YBT3 | pBT11/Z, pBT3/PHO80R | 127 | 18 |
| YBT3 | pBT11/Z, pYES2/PHO80 Glu | 243 | 33 |
| YBT3 | pBT11/Z, pYES2/PHO80 Gal | 28 | 19 |

Transformed cells were grown to $OD_{595}$ approximately equal to 1.0 in either low or high phosphate medium. Cells were permeabilized and β-galactosidase activity assays were performed as in Bitter et al., 1991.

Dependence on PHO85 and PHO80

To confirm that the inorganic phosphate-dependent reporter gene expression demonstrated in Example 2 is mediated by PHO85p and PHO80p, genetic experiments were performed. Haploid yeast strains were constructed containing disruptions of either the chromosomal PHO85 or PHO80 gene (Example 1). Regulation of LacZ reporter gene expression from pBT11 was tested in each of these yeast strains. The data in Table III demonstrate that repression of the promoter in pBT11/Z by high levels of phosphate is dependent on both the PHO85 and PHO80 gene products. In haploid yeast strains with either the PHO85 gene (strain YBT1) or PHO80 gene (strain YBT3) disrupted, the PHO5 promoter is not repressed in high phosphate. Dependence of high phosphate repression on both the PHO80 and PHO85 gene products is a characteristic expected of cyclin/CDK complexes.

Restoration of Phosphate Repression by Expressing PHO80 or PHO85 Genes from a Plasmid Expression of the PHO85 gene from a plasmid restores the phosphate regulation of a PHO5 promoter to the pho85 chromosomal deletion strain YBT1. Similarly, the phosphate regulation of PHO5 promoter activity in the pho80 mutant strain YBT3 can be restored by expression of the wild type PHO80 gene from a plasmid.

Interestingly, for both PHO80 and PHO85, complementation of the corresponding chromosomal disruption mutation occurs if the gene is present in the incorrect orientation relative to the promoter in the expression vector (Table III, pBT1/PHO85R, pBT1/PHO80R and pBT3/PHO80R). Because no complementation occurs with the pBT1 vector lacking a PHO85 gene, it appears that a low level of transcription occurs on the antisense strand of the genes in pBT1 and pBT3, and this results in synthesis of sufficient PHO80p or PHO85p for complementation. In these strains, regulation is restored so that the PHO5 promoter is repressed in high phosphate. Thus, only low levels of PHO80p or PHO85p expression appear to be required for complementation of the respective chromosomal gene disruption.

Surprisingly, when the PHO80 gene is in the correct orientation and expressed from the efficient TDH3 gene promoter in pBT1, derepression of the PHO5 promoter in low phosphate is not observed. Derepression in low phosphate is likewise not observed when the PHO80 gene is expressed from pBT3, which has 20–30% transcriptional activity of pBT1 (Bitter et al., 1991; Table III). High level expression of PHO80p appears to prevent inhibition of the PHO80p/PHO85p kinase in low phosphate. This interpretation is corroborated by expression of the wild type PHO80 gene from a galactose inducible promoter (pYES2; Table III). The high phosphate repression of PHO5 promoter activity in the pho80 gene disruption strain, YBT3, is restored if cells are grown in either galactose (inducing conditions for the pYES2 promoter) or glucose (repressing for the pYES2 promoter). Induction of the PHO5 promoter is observed in low phosphate if cells are grown in glucose (very low level expression of PHO80p) but is not observed when cells are grown in galactose (high level expression of PHO80p). Cumulatively, these results demonstrate that only small amounts of PHO80p are required for complementation of the pho80 gene disruption and that production of excess PHO80p prevents derepression of the PHO5 promoter in low phosphate. Thus, it appears that excess PHO80p titrates the inhibitor PHO81p, such that inhibition of the PHO80p/ PHO85p kinase by PHO81p does not occur. This interpretation, if correct, suggests that PHO80p alone and complexed with PHO85p is capable of interacting with PHO81p. Alternatively, excess PHO80p may bind to PHO4p (Jayaram et al., *EMBO J.* 13:2192–99). Whatever the mechanism responsible for failure to derepress the PHO5 promoter in the presence of high PHO80p expression levels, this phenomenon has been overcome by expressing PHO80p from the PHO80 promoters as described below.

Expression Vectors Utilizing Native PHO Regulon Gene Promoters

New yeast expression vectors were constructed incorporating the native PHO80 promoter (pBT15), PHO85 promoter (pBT16) or PHO81 (pBT17) promoter. These vectors allow cyclins, CDKs, and CKIs respectively to be expressed appropriately to restore high phosphate repression and low phosphate derepression of the PHO5 promoter to a cell disrupted for a cyclin, CDK or CKI. The HindIII to BamHI fragment of vector pBT5 (identical to pBT1, except for the TDH3 promoter segment incorporated) contains the GP381 promoter. This fragment was replaced with the PHO80, PHO85, or PHO81 promoter. The PHO promoters were PCR amplified from *S. cerevisiae* S288C genomic DNA using the primers indicated below. HindIII (AAGCTT) and BamHI (GGATCC) sites in the primers are underlined. Each PCR product was digested with HindIII and BamHI and cloned into a pBT5 plasmid vector that had been digested with HindIII and BamHI. Clones containing a vector in which the GP381 promoter was replaced with the indicated promoters were identified using standard techniques.

Figure 5:
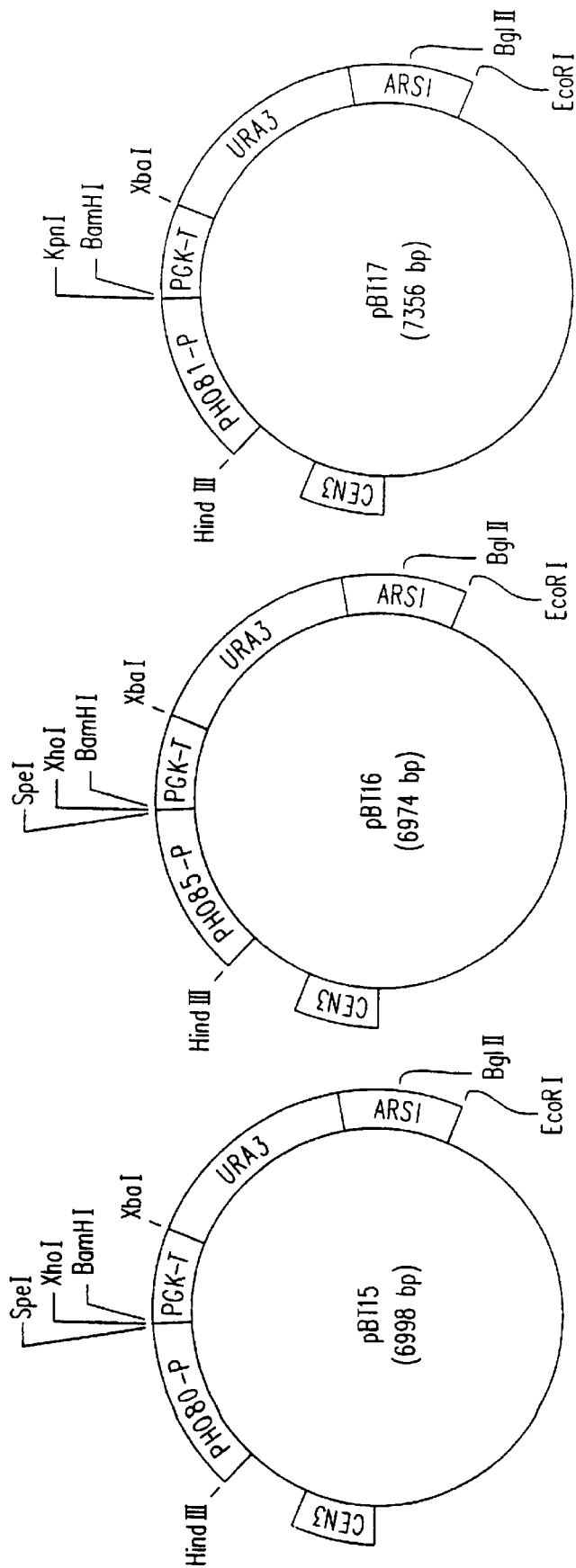
FIG. 5 is a restriction map of the expression vectors, pBT16, pBT15 and pBT17.

Vector pBT15 includes approximately 637 bp from the PHO80 gene promoter region (−638 to −2 relative to ATG initiation codon), isolated using the 5' primer, SEQ ID NO:19 and the 3' primer, SEQ ID NO:20. Vector pBT16 includes approximately 613 bp from the PHO85 gene promoter (−616 to −4 relative to ATG initiation codon), isolated using the 5' primer, SEQ ID NO:21, and the 3' primer, SEQ ID NO:22. Vector pBT17 includes approximately 1008 bp from the PHO81 gene promoter (−1011 to −4 relative to the ATG initiation codon), isolated using the 5' primer, SEQ ID NO:23, and the 3' primer, SEQ ID NO:24. These vectors are useful for expressing, respectively, cyclins, CDKs or CKIs at levels and under similar regulation as the native PHO80, PHO85 and PHO8 genes. Each of these vectors includes multiple cloning sites for genes to be inserted and expressed, and the restriction endonuclease map of each appears in FIG. 5.

The native PHO85 gene was expressed from pBT16 in strain YBT1, and the native PHO80 gene was expressed from pBT15 in strain YBT3. The results (Table IV) demonstrate complementation of the appropriate chromosomal disruption by each expression vector. Expression of the native PHO80 gene from pBT15 does not result in aberrant regulation as observed previously for high level expression of PHO80. That is, expression of PHO80 from pBT15 complements the chromosomal pho80 disruption, repressing the PHO5 promoter of pBT11/Z in high phosphate and allowing derepression of the PHO5 promoter in low phosphate.

TABLE IV

| | | Units β-galactosidase | |
|---|---|---|---|
| Strain + pBT11/Z | Expression Vector | Low Phosphate | High Phosphate |
| YPH500 | | 19.2 | 0.2 |
| YBT1 | | 95.6 | 118.2 |
| YBT1 | pBT16/PHO85 | 52.7 | 0.4 |
| YPH500 | | 13.0 | 1.1 |
| YBT3 | | 43.4 | 87.7 |
| YBT3 | pBT15/PHO80 | 24.3 | 0.8 |

Example 4
CONSTRUCTION OF MAMMALIAN-YEAST HYBRID GENES

Figure 2:
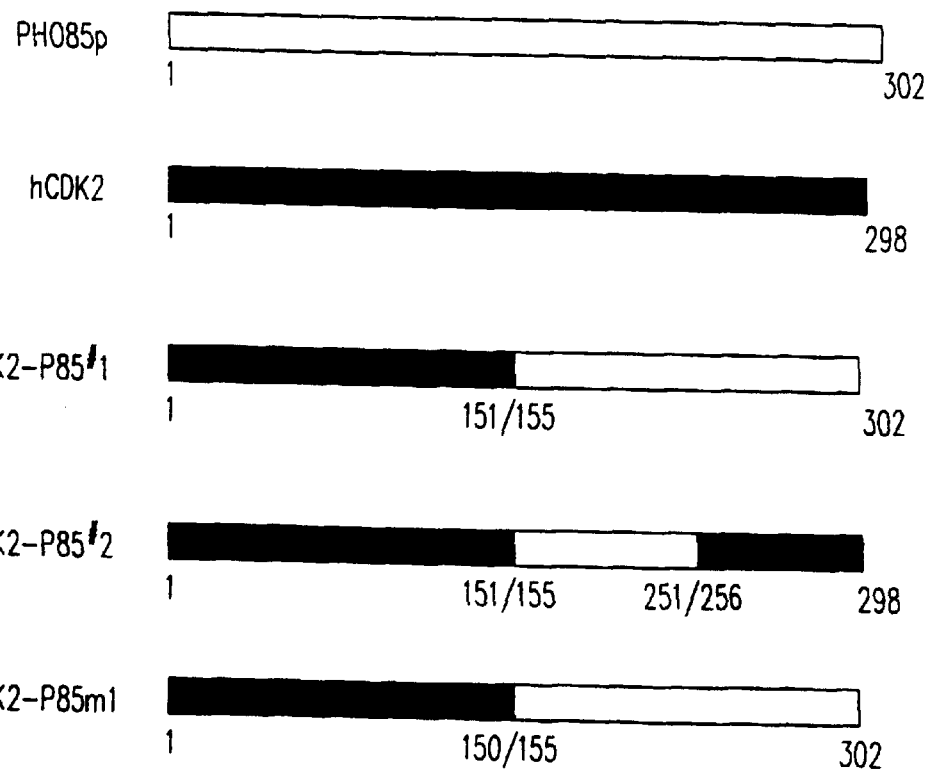
FIG. 2 is a schematic representation of three CDK2-PHO85 hybrid proteins.

The hybrid proteins having in frame fusions between human CDK2 and yeast PHO85 are depicted in FIG. 2. The CK2-P85#1 gene encodes amino acids 1 to 151 of hCDK2 fused to amino acids 155 to 302 of PHO85p. The CK2-P85#2 gene encodes amino acids 1 to 151 of hCDK2 fused in frame to amino acids 155 to 251 of PHO85p which in turn is fused in frame to amino acids 256 to 298 of hCDK2. The CK2-P85m1 gene is identical to CK2-P85#1 except for the deletion of the second alanine in the conserved GLARA motif (see amino acid sequences of fusion regions at end of this Example). The first two gene fusions were expressed from vector pBT6, while CK2-P85m1 was expressed from pYES2. Specific coding regions of the human CDK2 (hCDK2) and *S. cerevisiae* PHO85 used were obtained by PCR amplification, and hybrid genes were constructed using the overlap extension PCR amplification technique as described below.

The human CDK2 gene was obtained (ATCC #65967) in plasmid pSE1000. This yeast replicating plasmid with a URA3 marker has an approximately 1500 bp cDNA, including all of the coding region of human CDK2, cloned downstream of the yeast GAL1 promoter (Elledge and Spottswood, 1991, *EMBO J.*, 10:2653–2659).

Construction of CK2-P85#1.

Codons 1 to 151 of hCDK2 were PCR amplified from plasmid pSE1000 using the 5' primer, SEQ ID NO:25, and the 3' primer, SEQ ID NO:26. Codons 155 to 302 of PHO85 were PCR amplified from *S. cerevisiae* S288C genomic DNA using the 5' primer, SEQ ID NO:27, and the 3' primer, SEQ ID NO:28. The 5' end of the PHO85 5' primer is complementary to the hCDK2 3' primer. An overlap extension reaction of the two PCR products thus results in a full length hybrid gene, including codons 1–151 of hCDK2 fused in frame to codons 155–302 of PHO85. Approximately equimolar ratios of the two purified PCR products were mixed and PCR amplified in the presence of the hCDK2 5' primer and the PHO85 3' primer. The predominant amplification product in this second reaction was the full length approximately 961 bp hCDK2-PHO85 gene fusion. The purified PCR reaction products were digested with BamHI and SpeI and cloned into vector pBT6, which had been digested with BamHI and SpeI to generate pBT6/ CK2-P85#1.

Construction of CK2-P85#2

Codons 1 to 151 of hCDK2 were PCR amplified from pSE1000 DNA as described for construction of CK2-P85#1 to isolate the amino terminal coding portion of hCDK2. Codons 155 to 251 of PHO85 were PCR amplified from *S. cerevisiae* S288C genomic DNA using the 5' primer, SEQ ID NO:27, and the 3' primer, SEQ ID NO:29. The carboxy terminal codons 256–298 of hCDK2 were PCR amplified using the 5' primer, SEQ ID NO:30, and the 3' primer, SEQ ID NO:31. The 5' end of the PHO85 5' primer is complementary to the amino terminal hCDK2 (codons 1–151) 3' primer, while the 5' primer for the hCDK2 carboxy terminal region (codons 256–298) is complementary to the PHO85 3' primer. An overlap extension reaction of the three PCR products results in a full length hybrid gene, including codons 1–151 of hCDK2 fused in frame to codons 155–251 of PHO85, which is fused in frame to codons 256–298 of hCDK2. Approximately equimolar ratios of the three purified PCR products were mixed and PCR amplified in the presence of the hCDK2 amino terminal 5' primer and the hCDK2 carboxyl terminal 3' primer. The predominant amplification product in this second reaction was the full length approximately 1057 bp hCDK2-PHO85-hCDK2 gene fusion. The purified PCR reaction products were digested with BamHI and SpeI and cloned into a pBT6 plasmid vector that has been digested with BamHI and SpeI to generate pBT6/CK2-P85#2.

Construction of CK2-P85m1

A mutated version of CK2-P85#1, CK2-P85m1, was constructed as follows. Codons I to 149 of hCDK2 were PCR amplified from pSE1000 using the 5' primer, SEQ ID NO:32, and the 3' primer, SEQ ID NO:33. Codons 154 to 302 of PHO85 were PCR amplified from *S. cerevisiae* S288C genomic DNA using the 5' primer, SEQ ID NO:34 and the 3' primer, SEQ ID NO:28.

Fusion Junctions

The amino acid sequence of hCDK2 and PHO85p in the region of the first in frame fusion is represented respectively by SEQ ID NO:35 and SEQ ID NO:36. The amino acid sequence at the first fusion junction is depicted in SEQ ID NO:37. The amino acid sequence of hCDK2 and PHO85p in the region of the second in frame fusion is represented, respectively, by SEQ ID NO:38 and SEQ ID NO:39. The amino acid sequence at the second fusion junction is depicted in SEQ ID NO:40.

Construction of CK4-P85#1, a Hybrid of hCDK4 and PHO85

Codons 1–163 of human CDK4 (hCDK4) were PCR amplified from plasmid pCMV/CDK4 (constructed by Sander van den Huevel, Massachusetts General Hospital and obtained from Raymond Deshaies, California Institute of Technology) using the 5' primer, SEQ ID NO:50, and the 3' primer, SEQ ID NO:51. Codons 154 to 302 of PHO85 were PCR amplified using the 5' primer, SEQ ID NO:52, and the 3' primer, SEQ ID NO:28. The 5' end of SEQ ID NO:52 is complementary to SEQ ID NO:51. Approximately equimolar ratios of the two PCR products were mixed and PCR amplified in the presence of primers SEQ ID NO:50 and SEQ ID NO:28. The predominant PCR overlap extension product was an approximately 950 bp hCDK4-PHO85 fusion gene which encodes amino acids 1–163 of human CDK4 fused in-frame to amino acids 154 to 302 of yeast PHO85. The fusion gene was digested with SpeI and BamHI and cloned into pBT6 which had been digested with SpeI and BamHI. The fusion gene was excised from this intermediate plasmid by digestion with SpeI and BamHI, and cloned into pYES2 which had been digested with XbaI and BamHI, thus generating plasmid pYES2/CK4-P85#1. Plasmid pYES2/CK4-P85#1 was transformed into strain YBT1 containing plasmid pBT11/Z, and histidine, tryptophan and uracil prototrophs were selected.

Example 5
FUNCTION OF MAMMALIAN-YEAST HYBRIDS

Figure 6:
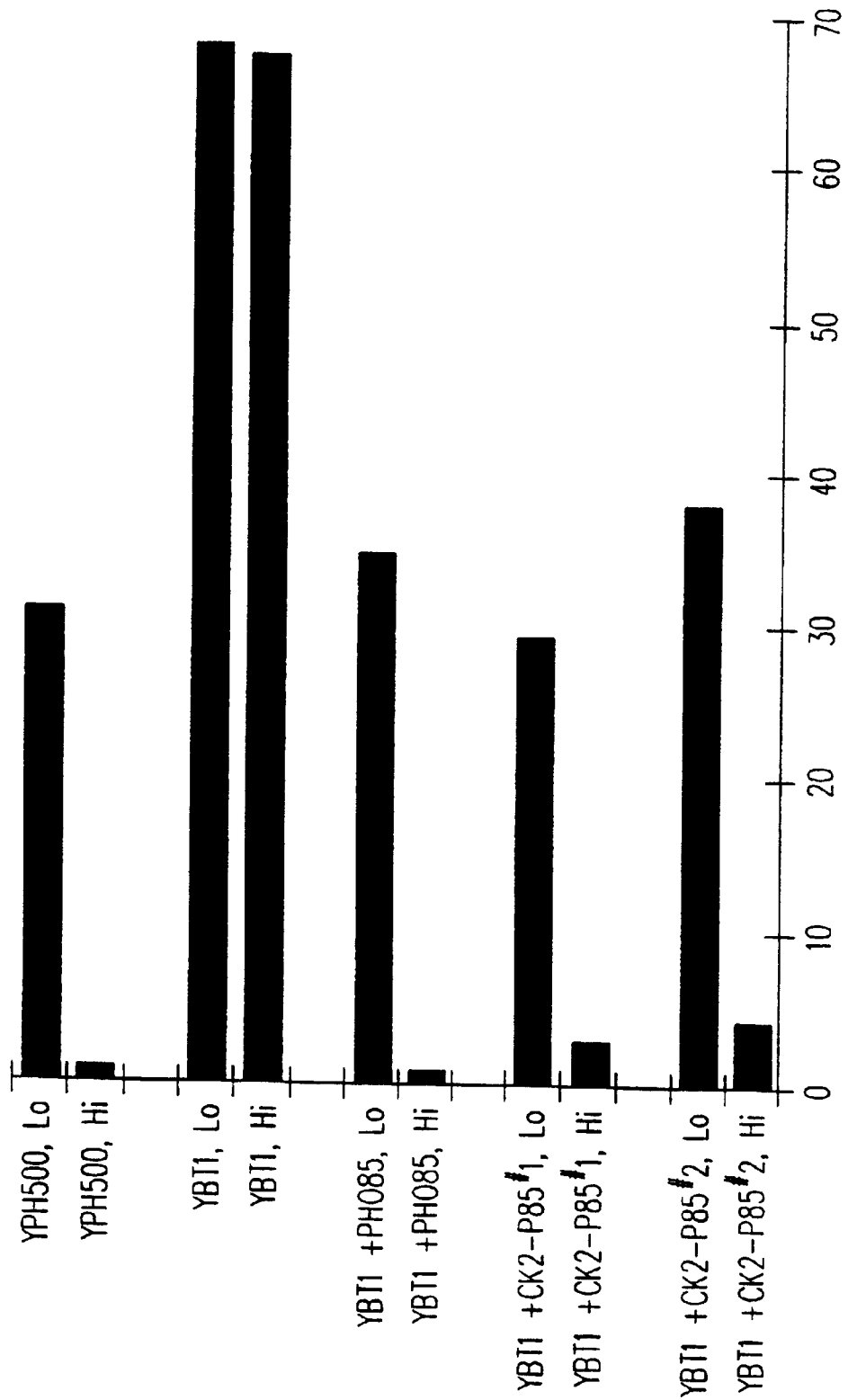
FIG. 6 is a graphical representation of comparative expression levels of reporter gene in different yeast strains.

The relative expression levels of various strains containing the pBT11/Z expression vector (LacZ reporter gene expressed from the native PHO5 promoter) is depicted in FIG. 6. The indicated yeast strains containing pBT11/Z were grown in either low or high phosphate medium. Where indicated, the strains expressed either the native yeast PHO85 gene from vector pBT1, or the hybrid CK2-P85#1 or CK2-P85#2 genes from vector pBT6. Cells were permeabilized and units β-galactosidase produced in each strain quantitated as described in Bitter et al. 1991. The data represent the average of four independent experiments for each strain. The wild type strain, YPH500, produces 38-fold more β-galactosidase units when grown in low phosphate than when grown under repressing conditions in high phosphate. In contrast, strain YBT1 which contains a pho85::HIS3 chromosomal gene disruption is not repressed in high phosphate. If the native yeast PHO85 gene is expressed (from vector pBT1/PHO85) in strain YBTI, the phosphate repression of pBT11/Z is restored. This demonstrates that a plasmid expressed PHO85 gene can complement the chromosomal pho85 disruption. The data in FIG. 6 further demonstrate that the hybrid proteins, CK2-P85#1 and CK2-P85#2, are each capable of complementing the pho85 disruption. Thus, CK2-P85#1 results in a 10.3 fold repression of reporter gene expression in high phosphate. Expression of hybrid gene CK2-P85#2 in the pho85 disruption strain results in a 9.2 fold repression in high phosphate.

Figure 7A:
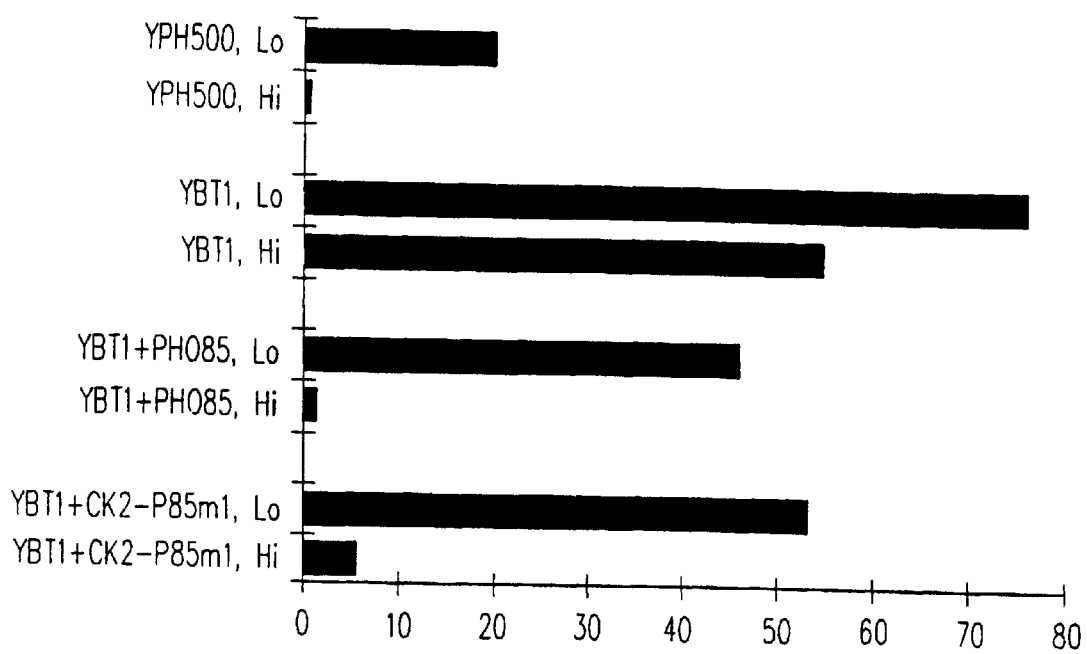
FIGS. 7A and 7B are graphical representations of experiments relating to CK2-P85m1 activity.
Figure 7B:
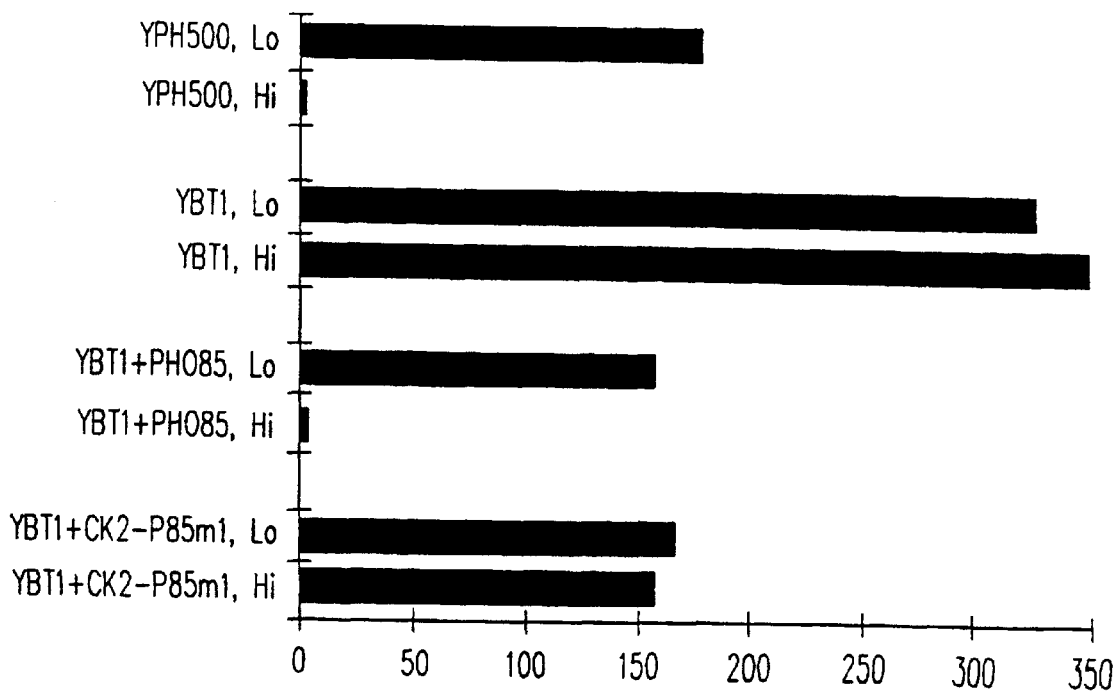

The hybrid CK2-P85m1 gene is also capable of complementing the pho85 disruption, as shown in FIG. 7. The indicated yeast strains containing pBT11/Z were grown in either low or high phosphate medium using either galactose or glucose as a carbon source. Where indicated, the strains expressed either the native yeast PHO85 gene from vector pBT1, or the hybrid CK2-P85m1 gene from vector pYES2. Units β-galactosidase produced in each strain was quantitated. When cells are grown in galactose (inducing conditions for the GAL1 promoter in vector pYES2), the CK2-P85m1 restores repression (9.8 fold) of the pBT11/Z reporter gene in high phosphate. In contrast, high phosphate repression is not observed when the cells are grown in glucose as the carbon source (repressing conditions for pYES2/CK2-P85m1) (FIG. 7B). The native PHO85 gene expressed from pBT1 complements a pho85 disruption strain when cells are grown in either galactose or glucose, since the promoter in pBT1/PHO85, derived from the TDH3 gene, is not regulated by carbon source.

The strain transformed with pYES2/CK4-P85#1, a plasmid encoding a hCDK4-PHO85 hybrid gene, was grown in either low or high phosphate medium using galactose as a carbon source. Cells were permeabilized and β-galactosidase quantitated as in Example 3. The strain produced 46.8 units β-galactosidase in low phosphate medium and 1.73 units in high phosphate medium. These results indicate that the hybrid CDK4-PHO85 protein encoded by pYES2/CK4-P85#1 complements the chromosomal pho85 gene disruption in yeast strain YBT1.

Example 6
CONSTRUCTION OF MAMMALIAN-YEAST HYBRID DELETION MUTANTS

Various deletion mutants of the CK2-P85#2 hybrid gene depicted in FIG. 2 were constructed as follows.

Construction of pBT6/P85-I

Codons 154 to 251 of PHO85 were PCR amplified from *S. cerevisiae* S288C DNA using the 5' primer, SEQ ID NO:53, which introduces an in frame ATG codon upstream of the alanine codon at position 154, and the 3' primer, SEQ ID NO:54, which introduces a termination codon after the leucine codon at position 251. The approximately 300 bp PCR product was digested with SpeI and BamHI and cloned into pBT6, which had been digested with SpeI and BamHI, to generate pBT6/P85-I.

Construction of pBT6/P85-N

Codons 1 to 153 of PHO85 were PCR amplified from *S. cerevisiae* S288C DNA using the 5' primer, SEQ ID NO:55, and the 3' primer, SEQ ID NO:56, which introduces a termination codon after the arginine codon at position 153. The approximately 470 bp PCR product was digested with SpeI and BamHI and cloned into pBT6, which had been digested with SpeI and BamHI, to generate pBT6/P85-N.

Construction of PBT6/CK2-P85ΔN

CK2-P85ΔN was constructed by overlap extension PCR. Codons 154 to 251 of PHO85 were PCR amplified from *S. cerevisiae* S288C DNA using the 5' primer, SEQ ID NO:53, and the 3' primer, SEQ ID NO:29; the amplification product includes an in-frame ATG upstream of codon 154 of PHO85. Codons 256 to 298 of hCDK2 were PCR amplified from pSE1000 using the 5' primer, SEQ ID NO:30, and the 3' primer, SEQ ID NO:31. The PHO85 3' primer is complementary to the 5' primer for the hCDK2 carboxy terminal region (codons 256–298). An overlap extension reaction of the two PCR products results in a full length hybrid gene, including codons 154–251 of PHO85 fused in frame to codons 256–298 of hCDK2. Approximately equimolar amounts of the PCR products were mixed and PCR amplified in the presence of primers SEQ ID NO:53 and SEQ ID NO:31. The predominant product in this overlap extension PCR was the approximately 460 bp gene fusion which was digested with SpeI and BamHI and cloned into pBT6, which had been digested with SpeI and BamHI, to generate pBT6/CK2-P85ΔN.

Construction of PBT6/CK2-P85ΔC

CK2-P85ΔC was constructed by overlap extension PCR. Codons 1 to 151 of hCDK2 were PCR amplified from plasmid pSE1000 using the 5' primer, SEQ ID NO:25, and the 3' primer, SEQ ID NO:26. Codons 155 to 251 of PHO85 were PCR amplified from *S. cerevisiae* S288C DNA using the 5' primer, SEQ ID NO:27, and the 3' primer, SEQ ID NO:54; the amplification product has a termination codon after leucine at position 251. The 5' end of SEQ ID NO:26 is complementary to the 5' end of SEQ ID NO:27. An overlap extension reaction of the two PCR products thus results in a truncated hybrid gene, including codons 1–151 of hCDK2 fused in frame to codons 155–251 of PHO85. Approximately equimolar amounts of the PCR products were mixed and PCR amplified in the presence of primers SEQ ID NO: 25 and SEQ ID NO:54. The predominant product in this overlap extension PCR was the approximately 750 bp gene fusion which was digested with SpeI and BamHI and cloned into pBT6, which had been digested with SpeI and BamHI, to generate pBT6/CK2-P85ΔC.

Construction of pBT6/CK2-N

Codons 1–151 of hCDK2 were PCR amplified from pSE1000 using the 5' primer, SEQ ID NO: 25, and the 3' primer, SEQ ID NO:57, which introduced a termination codon after the alanine codon at position 151. The approximately 460 bp PCR product was digested with SpeI and BamHI and cloned into pBT6, which had been digested with SpeI and BamHI, to generate pBT6/CK2-N.

Example 7

FUNCTION OF MAMMALIAN-YEAST HYBRID DELETION MUTANTS AND HOMOLOGOUS HUMAN GENE

The plasmids described in Example 6 were transformed into yeast strain YBT1 containing pBT11/Z selecting for uracil prototrophs. Plasmid pBT6/CK2-N was also transformed into strain YBT13 containing pBT11/Z. Plasmid pSE1000 (Elledge and Spottswood, 1991; ATCC #65967) contains the entire coding region of the human CDK2 cDNA cloned downstream of the yeast GAL1 promoter in a yeast replicating vector with a URA3 gene selectable marker. This plasmid was transformed into yeast strain YBT1 containing plasmid pBT11/Z, and uracil prototrophs were selected.

Cells were grown in either low or high phosphate medium containing a carbon source (YBT1/pSE1000 contained galactose) and units β-galactosidase produced were quantitated as in Example 2. The results are depicted in Table V.

TABLE V

| Yeast Strain + pBT11/Z | Expression Vector | Units β-galactosidase | |
|---|---|---|---|
| | | Low Phosphate | High Phosphate |
| YBT1 | none | 147.0 | 198.0 |
| YBT1 | pBT6/P85-I | 114.0 | 139.0 |
| YBT 1 | pBT6/P85-N | 185.1 | 114.0 |
| YBT 1 | pBT6/CK2-P85ΔN | 127.6 | 88.2 |
| YBT1 | pBT6/CK2-P85ΔC | 74.2 | 12.9 |
| YBT1 | pBT6/CK2-N | 67.0 | 7.3 |
| YBT 13 | pBT6/CK2-N | 169.6 | 191.7 |
| YBT1 | pSE1000 | 50.1 | 5.4 |

Example 5 demonstrated the ability of CK2-P85#2 to restore high-phosphate repression of reporter gene expression in strain YBT1 (which has a disrupted PHO85 gene). The abilities of deletion mutants of the CK2-P85#2 hybrid to restore phosphate-dependent differential expression of LacZ are shown in Table V. Vectors pBT6/CK2-P85ΔN and pBT6/P85-I differ from CK2-P85#2 in that both deletion mutants lack amino acids 1–151 of hCDK2; pBT6/P85-I additionally lacks amino acids 256–298 of hCDK2. Neither of these vectors restores high-phosphate repression to strain YBT1. In contrast, pBT6/CK2-P85ΔC, a vector in which the carboxyl terminus of CK2-P85#2 (amino acids 256–298 of hCDK2) is deleted, retains the high-phosphate repression capability of the parent hybrid.

Surprisingly, pBT6/CK2-N enables high phosphate repression of LacZ expression in YBT1. The pBT6/CK2-N protein contains amino acids 1–151 of hCDK2 (which is approximately one half of the native human molecule); it lacks the remainder of hCDK2 as well as any region of yeast PHO85p. Since complementation with CK2-N does not occur in strain YBT13, this truncated protein requires the yeast PHO80 gene product for regulation of the PHO5 promoter. Although the first 151 amino acids of hCDK2 can substitute for PHO85p function, a protein having the amino terminal 153 amino acids of PHO85p alone (the gene product of P85-N) does not complement the pho85 chromosomal disruption. The ability of pSE1000, which encodes full-length hCDK2, to restore high-phosphate repression of pBT11/Z expression in strain YPT1 demonstrates that hCDK2 can functionally replace yeast PHO85p. Therefore, methods of this invention can be used to identify compounds or proteins that affect native human CDKs.

Example 8

POSITIVE GENETIC SELECTION FOR PI REGULATED PROMOTER ACTIVITY

Two reporter genes were evaluated for suitability to allow positive selections for cyclin/CDK inhibition. The *E. coli* tn5 neo gene product confers resistance to the antibiotic G418, while the yeast LEU2 gene is involved in leucine biosynthesis. Each gene was PCR amplified and cloned into phosphate regulated yeast expression vectors (Example 1) to generate pBT11/NEO and pBT12/LEU2. Cells containing these expression vectors were cultured in either low or high phosphate medium to approximately $1 \times 10^7$ cells/mL. The cells were diluted and plated on either low or high phosphate plates with or without G418 (Table IV) or with or without leucine (Table VII). Plates were incubated for 3 days at 30° C. and the colonies arising from these plated cells were counted. The "total colonies per plate" represents the average of duplicate platings; "percentage G418 resistant colonies" represents total colonies per plate under selective conditions as a percentage of total colonies arising on duplicate plates under non-selective conditions.

TABLE VI

| Vector | Strain | $P_i$ level; cell dilution | Colonies per plate, G418$^R$ | Colonies per plate, NO selection | % G418$^R$ colonies per plate |
|---|---|---|---|---|---|
| pBT11/NEO | CM-1 | Low; $1 \times 10^{-3}$ | 270 | 307 | 88% |
| pBT11/NEO | CM-1 | Low; $4 \times 10^{-3}$ | 70 | 103 | 68% |
| pBT11/Z | CM-1 | Low; $1 \times 10^{-3}$ | 0 | 270 | 0 |
| pBT11/NEO | CM-1 | High, $1 \times 10^{-3}$ | 33 | 364 | 9% |
| pBT11/NEO | CM-1 | High, $4 \times 10^{-3}$ | 15 | 86 | 17% |
| pBT11/Z | CM-1 | High; $1 \times 10^{-3}$ | 0 | 325 | 0 |
| pBT11/NEO | CM-1 | Low; $1 \times 10^{-3}$ | 289 | 318 | 91% |
| pBT11/NEO | CM-1 | Low; $4 \times 10^{-3}$ | 74 | 106 | 70% |
| pBT11/Z | CM-1 | Low; $1 \times 10^{-3}$ | 0 | 270 | 0 |
| pBT11/NEO | CM-1 | High; $1 \times 10^{-3}$ | 261 | 378 | 69% |
| pBT11/NEO | CM-1 | High; $4 \times 10^{-3}$ | 72 | 90 | 80% |
| pBT11/Z | CM-1 | High; $1 \times 10^{-3}$ | 0 | 325 | 0 |

Cells were grown in either low or high phosphate liquid medium lacking tryptophan to select for the listed vector. Cultures were serially diluted in sterile water and 50 μL of the indicated dilution was plated onto SD, ade, leu, lys, ura plates to measure total cells or onto low or high phosphate plates lacking tryptophan and containing 5 mg/mL geneticin to measure G418-resistant cells. Cells were incubated at 30° C. Data in upper portion of Table are of cells scored 3 days after plating; data in lower portion of Table are of cells scored 4 days after plating.

Table VI displays results from experiments testing resistance to 5 mg/mL G418. pBT11/NEO confers G418 resistance to 68–88% of transformed CM-1 cells grown in low phosphate liquid medium and plated on low phosphate medium containing G418. In contrast, in pBT11/NEO bearing cells grown in high phosphate and plated on high phosphate medium containing G418, only 9–17% of cells are G418 resistant. These percentages may vary depending on the G418 concentration used. Colonies counted on high phosphate plates after a fourth day of incubation (see lower portion of Table III) show an increase in the number of G418 resistant colonies to 69–80%. The tn5 neo gene thus provides a positive selection for cells with an active PHO5 promoter, particularly when G418 resistance is assessed on or prior to the third day after plating. At no time was G418 resistance observed for cells transformed with an expression vector lacking a functional tn5 neo gene, indicating that the antibiotic resistance observed in high phosphate is due to low level background transcription of the neo gene. It is also noted that colonies appearing on high phosphate selective plates are distinctive by their small size relative to colonies arising on low phosphate selective plates.

TABLE VIIa

| | | | Colonies/plate | | |
|---|---|---|---|---|---|
| Vector | Strain | $P_i$ level; cell dilution | Colonies per plate, LEU2$^+$ | Colonies per plate, NO selection | % LEU2$^+$ colonies per plate |
| pBT12/LEU2 | YPH500 | Low; $1 \times 10^{-3}$ | 344 | 371 | 93% |
| pBT12/LEU2 | YPH500 | Low; $4 \times 10^{-3}$ | 96 | 108 | 89% |
| pBT12/LEU2 | YPH500 | High; $1 \times 10^{-3}$ | 25 | 506 | 5% |
| pBT12/LEU2 | YPH500 | High; $4 \times 10^{-3}$ | 8 | 128 | 6% |
| pBT12/LEU2 | YBT1 | Low; $1 \times 10^{-3}$ | 211 | 184 | 115% |
| pBT12/LEU2 | YBT1 | Low; $4 \times 10^{-3}$ | 36 | 61 | 60% |
| pBT12/LEU2 | YBT1 | High; $1 \times 10^{-3}$ | 89 | 84 | 106% |
| pBT12/LEU2 | YBT1 | High; $4 \times 10^{-3}$ | 28 | 25 | 112% |
| pBT11/Z | YPH500 | Low; $1 \times 10^{-3}$ | 0 | 393 | 0 |
| pBT11/Z | YPH500 | Low; $4 \times 10^{-3}$ | 0 | 86 | 0 |
| pBT11/Z | YPH500 | High; $1 \times 10^{-3}$ | 0 | 598 | 0 |
| pBT11/Z | YPH500 | High; $4 \times 10^{-3}$ | 0 | 109 | 0 |
| pBT11/Z | CM-1 | Low; $1 \times 10^{-3}$ | 221 | 212 | 104% |
| pBT11/Z | CM-1 | Low; $4 \times 10^{-3}$ | 58 | 50 | 116% |
| pBT11/Z | CM-1 | High; $1 \times 10^{-3}$ | 397 | 385 | 103% |
| pBT11/Z | CM-1 | High; $4 \times 10^{-3}$ | 101 | 58 | 174% |

The indicated yeast strains were grown in either low or high phosphate liquid medium lacking tryptophan to select for the listed vector. Cultures were serially diluted as indicated and plated onto SD, CAA, ade, ura plates to measure total cells or onto low or high phosphate plates lacking tryptophan and leucine to measure LEU2$^+$ cells. Colonies per plate represent the average of duplicate platings. Colonies on leucine selective plates were counted after 3 days incubation at 30° C.

TABLE VIIb

| | | | Colonies/plate | | |
|---|---|---|---|---|---|
| Vector | Strain | $P_i$ level; cell dilution | Colonies per plate, LEU2+ | Colonies per plate, NO Selection | % LEU2+ colonies per plate |
| pBT12/LEU2 | YPH500 | Low; $1 \times 10^{-3}$ | 356 | 382 | 93% |
| pBT11/LEU2 | YPH500 | Low; $4 \times 10^{-3}$ | 101 | 117 | 86% |
| pBT12/LEU2 | YPH500 | High; $1 \times 10^{-3}$ | 113 | 523 | 22% |
| pBT12/LEU2 | YPH500 | High; $4 \times 10^{-3}$ | 36 | 144 | 25% |
| pBT12/LEU2 | YBT1 | Low; $1 \times 10^{-3}$ | 221 | 193 | 114% |
| pBT12/LEU2 | YBT1 | Low; $4 \times 10^{-3}$ | 39 | 65 | 60% |
| pBT12/LEU2 | YBT1 | High; $1 \times 10^{-3}$ | 94 | 86 | 109% |
| pBT12/LEU2 | YBT1 | High; $4 \times 10^{-3}$ | 31 | 26 | 119% |

The plates from the experiment in Table VIIa were incubated for three additional days at 30° C. and additional colonies counted and added to the previous colony counts.

Table VIIa displays results from experiments testing phosphate dependence of the leucine prototropy (the ability to grow in media lacking leucine) in leu2⁻ cells transformed with pBT12/LEU2. When a yeast strain having a deletion of the chromosomal LEU2 gene (e.g. YPH500) is transformed with pBT12/LEU2, it exhibits leucine prototropy that is dependent on low phosphate concentrations. pBT12/LEU2 confers leucine prototropy to 89–93% of YPH500 cells grown in low phosphate liquid medium and plated onto low phosphate medium lacking leucine. Only 5–6% of the same pBT12/LEU2 transformed cells grow in high phosphate medium lacking leucine. As with the tn5 neo gene and G418 resistance, prolonged incubation (an additional three days) on high phosphate plates results in emergence of additional colonies (Table VIIb), indicating that selection appears to be most effective when carried out on or prior to the third day after plating. At no time was leucine prototropy observed for YPH500 cells transformed with pBT11/Z, an expression vector lacking a LEU2 gene, indicating that colonies emerging on high phosphate plates after prolonged incubation are due to background expression levels of the LEU2 gene. Table VIIa also shows that phosphate regulation of LEU2 expression from pBT12/LEU2 is dependent on PHO85, since phosphate dependence is not observed for YBT1 (leu2⁻pho85⁻) cells transformed with pBT12/LEU2.

The background gene expression detected under repressing conditions (high phosphate) may be reduced through adjustments to the plating regime. Pregrowth conditions in liquid culture, plate media composition and incubation conditions may be modified to reduce background. The basal level of transcription under repressed conditions may furthermore be reduced by modifying the reporter gene promoter and untranslated leader region.

Example 9
Identification of the Yeast Cyclin which is Required for the Function of the CK2-P85#2 Hybrid CDK S. cerevisiae strain YBT1 harboring plasmid pBT11/Z was transformed (Example 1) with BamHI digested pRS403ΔC/pho80::ADE2. HIS3 TRP1 ADE2 auxotrophs were selected on SD plates containing lysine, leucine and uracil. Strain YBT13 containing pBT11/Z was confirmed to be a pho85::HIS3 pho80::ADE2 double disruptant by PCR analysis of chromosomal DNA using appropriate primers (data not shown). This strain (YBT13; pBT11/Z) was transformed with either pBT1/PHO85 or pBT6/CK2-P85#2 (Examples 1 and 4) and selected for HIS3 TRP1 ADE2 URA3 auxotrophs on SD plates containing lysine and leucine.

Figure 9:
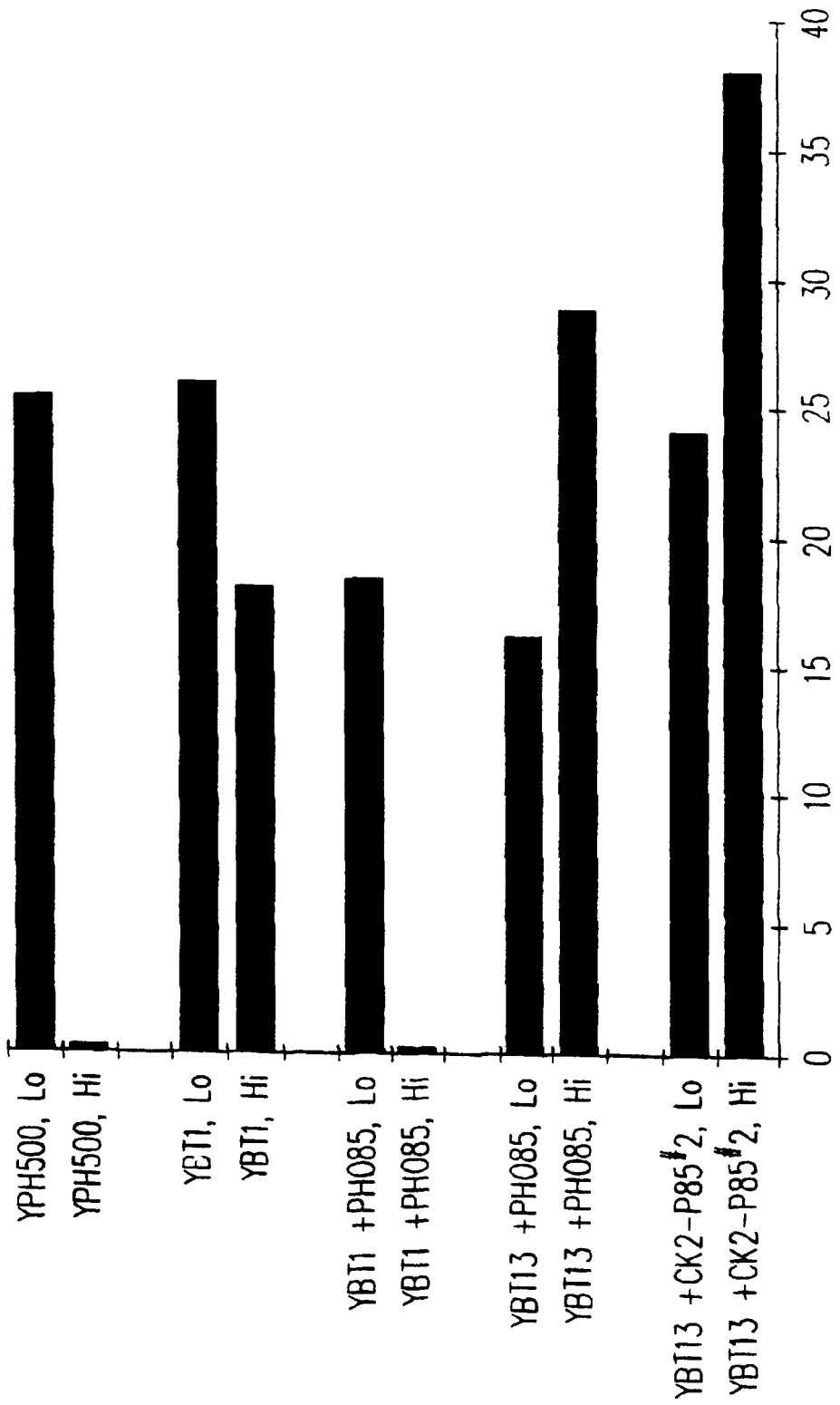
FIG. 9 is a graphical representation of β-galactosidase reporter gene activity produced in various cell lines containing a hybrid or a native CDK gene.

Strains containing the pBT11/Z reporter gene were grown in low or high phosphate medium and β-galactosidase measured on permeabilized cells (FIG. 9). Reporter gene expression in the wild type strain, YPH500, is repressed in high phosphate and derepressed in low phosphate while the pho85 disruption strain, YBT1, is not repressed in high phosphate. As observed in Examples 3 and 4, expression vector pBT1/PHO85 restores high phosphate repression to strain YBT1 since the plasmid expressed PHO85 gene is able to complement the pho85 chromosomal disruption. In contrast, pBT1/PHO85 does not restore high phosphate repression in strain YBT13. This failure to complement the chromosomal pho85 disruption is due to the lack in this strain of a functional cognate cyclin (PHO80p) for the PHO85p CDK. Although the expressed PHO85p is in this case from the plasmid, the phenotype is the same as that observed in YBT3 (Example 3) and confirms that PHO85p absolutely requires the PHO80p cyclin for activity. Expression vector pBT6/CK2-P85#2 also does not restore high phosphate repression of pBT11/Z in strain YBT13. Thus, the hybrid protein utilizes the PHO80p cyclin, and no other yeast cyclins are able to function in this capacity.

Example 10
SELECTION FOR COMPOUNDS FROM A COMBINATORIAL LIBRARY THAT INHIBIT CYCLIN/CDK.

S. cerevisiae strain YBT1 harboring plasmids pBT11/LEU2 and pBT6/CK2-P85#2 is utilized in this procedure. Samples from the combinatorial library to be screened are serially diluted in 50 μL volumes in 96 well microtiter plates. The combinatorial library samples are previously buffer-exchanged or diluted into high phosphate media selective for plasmid markers and for LEU2 expression (-trp, -ura, -leu). Approximately $1 \times 10^4$ to $1 \times 10^5$ cells in 50 μL high phosphate selective medium, are seeded into each well of the microtiter plates to give a final volume of 100 μL.

The microtiter plates are incubated at 30° C. for 12–48 hours. A compound that inhibits the CK2-P85#2 CDK derepresses the PHO5 promoter of pBT11/LEU2. Such cells are capable of growth in the absence of leucine. This results in an increase in optical density at 600 nm. The $OD_{600}$ of each well is measured in a microtiter plate reader. The following control cells, diluted into buffer without a test compound, are prepared for reference.

Negative controls: No cells.
YPH500 containing only pBT6/CK2-P85#2 (no LEU2 gene)
YPH500 containing pBT11/LEU2 (LEU2 gene

| Positive control: | repressed)<br>YBT1 containing only pBT11/LEU2 (LEU2 derepressed). |
|---|---|

Alternatively, the screen is performed utilizing, as a host, a yeast strain which has a disruption of the chromosomal pho81 gene. In this strain, the reporter gene remains repressed in low phosphate since a functional PHO81p CKI is not produced. This screen is performed in phosphate depleted medium.

Example 11
SCREEN OF COMBINATORIAL LIBRARY FOR CYCLIN/CDK INHIBITORS

S. cerevisiae strain YBT1 harboring plasmids pBT11/Z and pBT6/CK2-P85#2 is utilized in this procedure. Samples from the combinatorial library to be screened are serially diluted in 50 μL volumes in 96 well microtiter plates. The combinatorial library samples are previously buffer exchanged or diluted into high phosphate medium selective for plasmid markers (-trp, -ura). Approximately $1 \times 10^3$ to $1 \times 10^5$ cells, in 50 μL of high phosphate selective media, are seeded into each well of the microtiter plates to give a final volume of 100 μL.

The microtiter plates are incubated at 30° C. for 12–48 hours. A compound that inhibits the CK2-P85#2 CDK derepresses the PHO5 promoter of pBT11/Z. Such cells transcribe the LacZ gene and synthesize β-galactosidase. β-Galactosidase enzyme activity in each well is assayed with the Galacto-Light™ kit (Tropix; Bedford, Mass.). Quantitation of the following control cells, diluted into buffer without test compound, are prepared for reference.

| Negative controls: | No cells.<br>YBT1 containing only pBT6/CK2-P85#2 (no LacZ gene)<br>YPH500 containing pBT11/Z (LacZ gene repressed) |
|---|---|
| Positive control: | YBT1 containing only pBT11/Z (LacZ derepressed) |

Alternatively, the screen is performed utilizing, as a host, a yeast strain which has a disruption of the chromosomal pho81 gene. In this strain, the reporter gene remains repressed in low phosphate since a functional PHO81p CKI is not produced. Therefore, the screen in this host is performed in phosphate depleted medium.

Example 12
SELECTION FOR PEPTIDEs THAT INHIBIT CYCLIN/CDK FROM A CDNA LIBRARY

S. cerevisiae strain YBT1 harboring plasmids pBT11/LEU2 and pBT6/CK2-P85#2 is utilized in this procedure. The source material utilized is a human cDNA bank constructed using standard techniques (Ausubel et al., Current Protocols in Mol. Biol., Wiley Interscience, Publishers) from mRNA isolated from an appropriate tissue or cell line. The cDNA bank is constructed in a yeast expression vector such as p413-MET25 (Mumberg et al., 1994, Nucleic Acids Research 22:5767–5768). The cDNA bank is introduced into the above strain using selection on plates lacking histidine. The yeast library is grown in high phosphate liquid culture with selection for all three plasmids (-trp, -ura, -his) and in the absence of methionine (in order to derepress the MET25 promoter which controls expression of the cDNA). Any peptide encoded by a cDNA which inhibits the CK2-P85#2 will result in derepression of the PHO5 promoter of pBT11/LEU2, enabling such cells to grow in the absence of leucine. After growth of the population of cells for 12–48 hours, cells are plated for individual colonies which are leucine prototrophs on selective plates (-trp, -ura, -his, -met, -leu). Colonies are selected after at least 1 day, and less than 3 days, incubation at 30° C.

Colonies isolated in the above screen contain putative cDNA which encodes peptides capable of inhibiting the CK2-P85#2. These clones are subjected to secondary screens as follows. The cDNA in the p413MET25 vector in each isolated yeast clone is recovered by shuttling into E. coli and subsequently introduced into S. cerevisiae YBT1 cells containing plasmids pBT11/LEU2 and pBT1/PHO85. If this strain is now a leucine prototroph in high phosphate, then the isolated cDNA also inhibits PHO85p, and may be a general CDK inhibitor. If this secondary screen shows no effect of the expressed cDNA, then the inhibitory activity is specific for the human CDK2 epitopes incorporated into CK2-P85#2.

Alternatively, the screen is performed utilizing, as a host, a yeast strain which has a disruption of the chromosomal pho81 gene. In this strain, the reporter gene remains repressed in low phosphate since a functional PHO81p CKI is not produced. Therefore, the screen in this host is performed in phosphate depleted medium.

Example 13
SELECTION FOR PEPTIDES THAT INHIBIT CYCLIN/CDK FROM A RANDOM PEPTIDE LIBRARY Procedure is the same as in Example 10, except random peptide coding bank is used in the p413MET25 expression vector. This can be a free peptide bank or a structurally constrained peptide bank as described in Colas et al. (1996) Nature 380, 548–550.

Example 14
USE OF E2F MAMMALIAN CELL SYSTEM

Standard recombinant DNA techniques are utilized to place the E. coli LacZ gene under control of the chinese hamster ovary cell (CHO) dihydrofolate reductase gene (DHFR) promoter. CHO cells are stably transfected with this construct and clones selected by standard techniques (Ausubel et al.). Since the DHFR promoter is activated by E2F, monitoring LacZ expression in this cell line directly measures the availability of functional E2F and indirectly measures the activity of cell cycle regulatory proteins. E2F heterodimerizes with RB and in this form is incapable of activating promoters. Phosphorylation by cyclin E/CDK2 in late G1 phase causes dissociation of the heterodimer enabling E2F to activate responsive promoters. Subsequently, in S phase, cyclin A/CDK2 phosphorylates free E2F resulting in inactivation of its DNA binding activity. Thus, expression of the LacZ reporter gene under control of the DHFR gene in this cell line is cell cycle dependent.

Reporter gene expression is monitored using the Galacto-Light™ kit (Tropix; Bedford, Mass.). Lower levels of expression may be measured in asynchronous cultures since only approximately 20–30% of the population are expected to be in the phase of the cell cycle when transcriptionally competent free E2F is present. Synchronized cultures may be utilized and β-galactosidase assays performed at or near the beginning of S phase to optimize the reporter gene signal.

This cell line is utilized to screen for inhibitors of cyclin A/CDK2 as follows. The compound is administered to the cell line. A loss of reporter gene expression correlates with inhibition of cyclin E/CDK2. In the preferred embodiment of this invention, synchronized cell cultures are used and β-galactosidase assays performed at the time, and for the duration, previously determined to be optimal for reporter gene quantitation.

All publications and patent applications mentioned in this specification are herein incorporated by reference to the same extent as if each individual publication or patent application was specifically and individually indicated to be incorporated by reference.

I claim:

1. A method of screening for a compound that affects mammalian cell cycle regulatory proteins, comprising:
   a. administering a compound to a cell line, wherein said cell line comprises genetic information comprising
      i. a reporter gene operably linked to a gene expression control sequence, wherein said gene expression control sequence comprises an Upstream Activation Sequence and a promoter, and said Upstream Activation Sequence comprises a DNA region that binds to a transcription control factor that is regulated through phosphorylation by a cyclin/CDK phosphorylation system; and
      ii. an effector gene providing a gene product distinct from said transcription control factor and effective to permit normal cyclin/CDK regulation of said-transcription control factor; and
   b. analyzing expression of said reporter gene in said cell line, thereby determining whether said compound affects said normal regulation.

2. The method of claim 1, wherein said an effector gene is a hybrid gene comprising a first coding region from a gene native to said cell line and a second coding region from a second gene, wherein said native gene encodes a gene product that affects phosphorylation by said cyclin/CDK phosphorylation system, and said second gene is mammalian and is homologous to said native gene, and wherein said cell line further comprises a chromosomal mutation in said native gene.

3. The method of claim 2, wherein said hybrid gene is a cyclin-dependent kinase.

4. The method of clain 3, wherein said native gene is PHO85 and said transcription control factor is PHO4p.

5. The method of claim 4, wherein said second gene encodes a protein selected from the group consisting of hCDK2 and hCDK4.

6. The method of claim 1, wherein said effector gene is a mammalian gene.

7. The method of claim 6, wherein said mammalian gene is a cyclin-dependent kinase.

8. The method of claim 7, wherein said mammalan gene encodes hCDK2 and said transcription control factor is PHO4p.

9. The method of claim 7, wherein said mammalian gene encodes the amino terminus of hCDK2 and said cell line is YBT1.

10. The method of claim 1, wherein said cell line is a yeast cell line.

11. The method of claim 10, wherein said yeast cell line has a chromosomal mutation in a gene selected from the group consisting of PDR5, SN22, YOR1, PDR1 and PDR3.

12. A method of identifying a gene that affects mammalian cell cycle regulatory proteins, comprising:
   a. providing a cell line that comprises genetic information comprising
      i. a reporter gene operably linked to a gene expression control sequence, wherein said gene expression control sequence comprises an Upstream Activation Sequence and a promoter, and said Upstream Activation Sequence comprises a DNA region that binds to a transcription control factor that is regulated through phosphorylation by a cyclin/CDK phosphorylation system; and
      ii. an effector gene providing a gene product distinct from said transcription control factor and effective to permit normal cyclin/CDK regulation of said transcription control factor;
   b. introducing into said cell line expression of an exogenous gene; and
   c. analyzing expression of said reporter gene, thereby determining whether said exogenous gene affects said normal regulation.

13. The method of claim 12, wherein said an effector gene is a hybrid gene comprising a first coding region from a gene native to said cell line and a second coding region from a second gene, wherein said native gene encodes a gene product that affects phosphorylation by said cyclin/CDK phosphorylation system, and said second gene is mammalian and is homologous to said native gene, and wherein said cell line further comprises a chromosomal mutation in said native gene.

14. The method of claim 13, wherein said hybrid gene is a cyclin-dependent kinase.

15. The method of claim 14, wherein said native gene is PHO85 and said transcription control factor is PHO4p.

16. The method of claim 15, wherein said second gene encodes a protein selected from the group consisting of hCDK2 and hCDK4.

17. The method of claim 12, wherein said effector gene is a mammalian gene.

18. The method of claim 17, wherein said mammalian gene is a cyclin-dependent kinase.

19. The method of claim 18, wherein said mammalian gene encodes hCDK2 and said transcription control factor is PHO4p.

20. The method of claim 18, wherein said mammalian gene encodes the amino terminus of hCDK2 and said cell line is YBT1.

21. A method of identifying a gene that affects mammalian cell cycle regulatory proteins, comprising:
   a. providing a cell line that comprises genetic information comprising
      i. a reporter gene operably linked to a gene expression control sequence, wherein said gene expression control sequence comprises an Upstream Activation Sequence and a promoter, and said Upstream Activation Sequence comprises a DNA region that binds to a transcription control factor that is regulated through phosphorylation by a cyclin/CDK phosphorylation system; and
      ii. an effector gene providing a gene product distinct from said transcription control factor and effective to permit normal cyclin/CDK regulation of said transcription control factor;
   b. introducing a mutation in a chromosomal test gene; and
   c. analyzing expression of said reporter gene, thereby determining whether said test gene affects said normal regulation.

22. A cell line comprising genetic information comprising:
   i. a reporter gene operably linked to a gene expression control sequence, wherein said gene expression control sequence comprises an Upstream Activation Sequence and a promoter, and said Upstream Activation Sequence comprises a DNA region that binds to a transcription control factor that is regulated through phosphorylation by a cyclin/CDK phosphorylation system;
   ii. a hybrid gene comprising a first coding region from a gene native to said cell line and a secund coding region from a second gene, wherein said native gene encodes a gene product that affects phosphorylation by said cyclin/CDK phosphorylation system, and said second gene is mammalian and is homologous to said native gene, and said hybrid gene provides a gene product distinct from said transcription control factor and effective to permit normal cyclin/CDK regulation of said transcription control factor; and iii. a chromosomal mutation in said native gene.

23. The cell line of claim 22, wherein said cell line is a yeast cell line having a chromosomal mutation in a gene selected from the group consisting of PDR5, SN22, YOR1, PDR1 and PDR3.

24. A cell line comprising genetic information comprising:

i. a reporter gene operably linked to a gene expression control sequence, wherein said gene expression control sequence comprises an Upstream Activation Sequence and a promoter, and said Upstream Activation Sequence comprises a DNA region that binds to a transcription control factor that is regulated through phosphorylation by a cyclin/CDK phosphorylation system;

ii. a mammalian gene homologous to a gene native to said cell line, wherein said native gene encodes a gene product that affects phosphorylation by said cyclin/CDK phosphorylation system, and said mammalian gene provides a gene product distinct from said transcripton control factor and effective to permit normal cyclin/CDK regulation of said transcription control factor; and iii. a chromosomal mutation in said native gene.

25. The cell line of claim 24, wherein said cell line is a yeast cell line having a chromosomal mutation in a gene selected from the group consisting of PDR5, SN22, YOR1, PDR1 and PDR3.

26. The method of claim 2, wherein said native gene is selected from the group consisting of PHO85, PHO80 and PHO81 and said transcription control factor is PHO4p.

27. The method of claim 2, wherein said second gene encodes a gene product selected from the group consisting of CDK2 and CDK4, and said transcription control factor is PHO4.

28. The method of claim 2, wherein said second gene encodes a gene product selected from the group consisting of CDK2, cyclin A, cyclin E, p16$^{INK4a}$, CDK4 and cyclin D, and said transcription control factor is E2F.

29. The method of claim 2, wherein said second gene encodes a gene product selected from the group consisting of CDK4 and cyclin D, and said transcription control factor is DMP1.

30. The method of claim 13, wherein said native gene is selected from the group consisting of PHO85, PHO80 and PHO81 and said transcription control factor is PHO4p.

31. The method of claim 13, wherein said second gene encodes a gene product selected from the group consisting of CDK2 and CDK4, and said transcription control factor is PHO4.

32. The method of claim 13, wherein said second gene encodes a gene product selected from the group consisting of CDK2, cyclin A, cyclin E, p16$^{INK4a}$, CDK4 and cyclin D, and said transcription control factor is E2F.

33. Fhe method of claim 13, wherein said second gene encodes a gene product selected from the group consisting of CDK4 and cyclin D, and said transcription control factor is DMP1.

* * * * *

SEQUENCE LISTING (1) GENERAL INFORMATION:

(iii) NUMBER OF SEQUENCES: 57

(2) INFORMATION FOR SEQ ID NO:1:

(i) SEQUENCE CHARACTERISTICS:
      (A) LENGTH: 30
      (B) TYPE: nucleic acid
      (C) STRANDEDNESS:  single stranded
      (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:1:

GCGCGGATCC AAATAAATTG AATTGAATTG      30

(2) INFORMATION FOR SEQ ID NO:2:

(i) SEQUENCE CHARACTERISTICS:
      (A) LENGTH: 31
      (B) TYPE: nucleic acid
      (C) STRANDEDNESS: single stranded
      (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:2:

GCGCTCTAGT ACGAAACGCA GAATTTTCGA G      31

(2) INFORMATION FOR SEQ ID NO:3:

(i) SEQUENCE CHARACTERISTICS:
      (A) LENGTH: 28
      (B) TYPE: nucleic acid
      (C) STRANDEDNESS:  single stranded
      (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:3:

GCGCGAATTC AAAAGTCAAC CCCCTGCG      28

(2) INFORMATION FOR SEQ ID NO:4:

(i) SEQUENCE CHARACTERISTICS:
      (A) LENGTH: 28
      (B) TYPE: nucleic acid
      (C) STRANDEDNESS: single stranded
      (D) TOPOLOGY: linear

```
        (ii) MOLECULE TYPE: DNA (iii) HYPOTHETICAL: NO (iv) ANTI-SENSE: NO (xi) SEQUENCE DESCRIPTION: SEQ ID NO:4:

GCGCGGATCC GTAAGCGGAG GTGTGGAG                                        28

(2) INFORMATION FOR SEQ ID NO:5:

(i) SEQUENCE CHARACTERISTICS:
              (A) LENGTH: 47
              (B) TYPE: nucleic acid
              (C) STRANDEDNESS: single stranded
              (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:5:

GATCTCGAAT AAACACACAT AAATAAACAA ACTAGTATCT CGAGTAG                   47

(2) INFORMATION FOR SEQ ID NO:6:

(i) SEQUENCE CHARACTERISTICS:
              (A) LENGTH: 28
              (B) TYPE: nucleic acid
              (C) STRANDEDNESS: single stranded
              (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:6:

CGCGGTACCG CGCTTTTTCT TTGTCTGC                                        28

(2) INFORMATION FOR SEQ ID NO:7:

(i) SEQUENCE CHARACTERISTICS:
              (A) LENGTH: 36
              (B) TYPE: nucleic acid
              (C) STRANDEDNESS: single stranded
              (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:7:

CGCGGATCCG TCGACCGAAT TTGCTTGCTC TATTTG                               36

(2) INFORMATION FOR SEQ ID NO:8:

(i) SEQUENCE CHARACTERISTICS:
              (A) LENGTH: 28
              (B) TYPE: nucleic acid
              (C) STRANDEDNESS: single stranded
              (D) TOPOLOGY: linear (ii) MOLECULE TYPE: DNA
```

(iii) HYPOTHETICAL: NO (iv) ANTI-SENSE: NO (xi) SEQUENCE DESCRIPTION: SEQ ID NO:8:

CGCGTCGACG AAAACAGGGA CCAGAATC                                                       28

(2) INFORMATION FOR SEQ ID NO:9:

(i) SEQUENCE CHARACTERISTICS:
            (A) LENGTH: 27
            (B) TYPE: nucleic acid
            (C) STRANDEDNESS: single stranded
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:9:

CGCGGATCCT ATTAAAACAA TAAATTG                                                        27

(2) INFORMATION FOR SEQ ID NO:10:

(i) SEQUENCE CHARACTERISTICS:
            (A) LENGTH: 26
            (B) TYPE: nucleic acid
            (C) STRANDEDNESS: single stranded
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:10:

CGCAGATCTA TTATACGGGA GCTCCG                                                         26

(2) INFORMATION FOR SEQ ID NO:11:

(i) SEQUENCE CHARACTERISTICS:
            (A) LENGTH: 30
            (B) TYPE: nucleic acid
            (C) STRANDEDNESS: single stranded
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:11:

GCGCGGATCC AAAAATCAAC CTCGAGCTCT                                                     30

(2) INFORMATION FOR SEQ ID NO:12:

(i) SEQUENCE CHARACTERISTICS:
            (A) LENGTH: 30
            (B) TYPE: nucleic acid
            (C) STRANDEDNESS: single stranded
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:12:

GCGCGGATCC GTTTTTCGCT GACGGGCTGC                              30

(2) INFORMATION FOR SEQ ID NO:13:

(i) SEQUENCE CHARACTERISTICS:
        (A) LENGTH: 30
        (B) TYPE: nucleic acid
        (C) STRANDEDNESS: single stranded
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:13:

GCGCGGATCC GGAGACTCAT AGAAATCATC                              30

(2) INFORMATION FOR SEQ ID NO:14:

(i) SEQUENCE CHARACTERISTICS:
        (A) LENGTH: 30
        (B) TYPE: nucleic acid
        (C) STRANDEDNESS: single stranded
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:14:

GCGCGGATCC ATAATACCCC ACGAAAAATC                              30

(2) INFORMATION FOR SEQ ID NO:15:

(i) SEQUENCE CHARACTERISTICS:
        (A) LENGTH: 27
        (B) TYPE: nucleic acid
        (C) STRANDEDNESS: single stranded
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:15:

GCGGGATCCT CTCGAACTTA AGGCTAG                                 27

(2) INFORMATION FOR SEQ ID NO:16:

(i) SEQUENCE CHARACTERISTICS:
        (A) LENGTH: 25
        (B) TYPE: nucleic acid
        (C) STRANDEDNESS: single stranded
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:16:

```
CGCGGATCCA TTTCGAACCC CAGAG                                              25

(2) INFORMATION FOR SEQ ID NO:17:

(i) SEQUENCE CHARACTERISTICS:
        (A) LENGTH: 30
        (B) TYPE: nucleic acid
        (C) STRANDEDNESS: single stranded
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:17:

GCGGGATCCT ATATATTTCA AGGATATACC                                         30

(2) INFORMATION FOR SEQ ID NO:18:

(i) SEQUENCE CHARACTERISTICS:
        (A) LENGTH: 30
        (B) TYPE: nucleic acid
        (C) STRANDEDNESS: single stranded
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:18:

GCGGGATCCT AAAGTTTATG TACAAATATC                                         30

(2) INFORMATION FOR SEQ ID NO:19:

(i) SEQUENCE CHARACTERISTICS:
        (A) LENGTH: 31
        (B) TYPE: nucleic acid
        (C) STRANDEDNESS: single stranded
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:19:

GCGCAAGCTT CCCTAGAGGA AGTACGATAT C                                       31

(2) INFORMATION FOR SEQ ID NO:20:

(i) SEQUENCE CHARACTERISTICS:
        (A) LENGTH: 48
        (B) TYPE: nucleic acid
        (C) STRANDEDNESS: single stranded
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:20:

GCGCGGATCC TACTCGAGAT ACTAGTTATT TCTATGAGTC TCCAAAGG                     48
```

(2) INFORMATION FOR SEQ ID NO:21:

(i) SEQUENCE CHARACTERISTICS:
        (A) LENGTH: 29
        (B) TYPE: nucleic acid
        (C) STRANDEDNESS: single stranded
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:21:

CGCGAAGCTT GGCTTAACCA TTGAGGTCC                            29

(2) INFORMATION FOR SEQ ID NO:22:

(i) SEQUENCE CHARACTERISTICS:
        (A) LENGTH: 50
        (B) TYPE: nucleic acid
        (C) STRANDEDNESS: single stranded
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:22:

GCGCGGATCC TACTCGAGAT ACTAGTTATT GCTCAAGTTT GCCCAGTTTG        50

(2) INFORMATION FOR SEQ ID NO:23:

(i) SEQUENCE CHARACTERISTICS:
        (A) LENGTH: 21
        (B) TYPE: nucleic acid
        (C) STRANDEDNESS: single stranded
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:23:

GGCAATTATA CGAAGCTTGT G                                      21

(2) INFORMATION FOR SEQ ID NO:24:

(i) SEQUENCE CHARACTERISTICS:
        (A) LENGTH: 42
        (B) TYPE: nucleic acid
        (C) STRANDEDNESS: single stranded
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:24:

GCGCGGATCC AATAGGTACC ACGTTTATCT ATCTATGTTG CC                42

(2) INFORMATION FOR SEQ ID NO:25:

(i) SEQUENCE CHARACTERISTICS:

(A) LENGTH: 29
            (B) TYPE: nucleic acid
            (C) STRANDEDNESS: single stranded
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:25:

GCGCACTAGT ATGGAGAACT TCCAAAAGG                                            29

(2) INFORMATION FOR SEQ ID NO:26:

(i) SEQUENCE CHARACTERISTICS:
            (A) LENGTH: 21
            (B) TYPE: nucleic acid
            (C) STRANDEDNESS: single stranded
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:26:

AGCTCTGGCT AGTCCAAAGT C                                                    21

(2) INFORMATION FOR SEQ ID NO:27:

(i) SEQUENCE CHARACTERISTICS:
            (A) LENGTH: 39
            (B) TYPE: nucleic acid
            (C) STRANDEDNESS: single stranded
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:27:

GACTTTGGAC TAGCCAGAGC TTTCGGTATT CCGGTCAAC                                 39

(2) INFORMATION FOR SEQ ID NO:28:

(i) SEQUENCE CHARACTERISTICS:
            (A) LENGTH: 30
            (B) TYPE: nucleic acid
            (C) STRANDEDNESS: single stranded
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:28:

GCGCGGATCC GTTTTTCGCT GACGGGCTGC                                           30

(2) INFORMATION FOR SEQ ID NO:29:

(i) SEQUENCE CHARACTERISTICS:
            (A) LENGTH: 21
            (B) TYPE: nucleic acid
            (C) STRANDEDNESS: single stranded (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:29:

TAGGTCTCTT GGTGGTCGTT G                                                    21

(2) INFORMATION FOR SEQ ID NO:30:

(i) SEQUENCE CHARACTERISTICS:
            (A) LENGTH: 40
            (B) TYPE: nucleic acid
            (C) STRANDEDNESS: single stranded
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:30:

CAACGACCAC CAAGAGACCT AGATGAAGAT GGACGGAGCT                                 40

(2) INFORMATION FOR SEQ ID NO:31:

(i) SEQUENCE CHARACTERISTICS:
            (A) LENGTH: 27
            (B) TYPE: nucleic acid
            (C) STRANDEDNESS: single stranded
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:31:

GCGCGGATCC CGGGGGCTTC AAGAAGG                                              27

(2) INFORMATION FOR SEQ ID NO:32:

(i) SEQUENCE CHARACTERISTICS:
            (A) LENGTH: 29
            (B) TYPE: nucleic acid
            (C) STRANDEDNESS: single stranded
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:32:

GCGCGGATCC ATGGAGAACT TCCAAAAGG                                            29

(2) INFORMATION FOR SEQ ID NO:33:

(i) SEQUENCE CHARACTERISTICS:
            (A) LENGTH: 20
            (B) TYPE: nucleic acid
            (C) STRANDEDNESS: single stranded
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:33:

TCTGGCTAGT CCAAAGTCTG                                               20

(2) INFORMATION FOR SEQ ID NO:34:

(i) SEQUENCE CHARACTERISTICS:
           (A) LENGTH: 39
           (B) TYPE: nucleic acid
           (C) STRANDEDNESS: single stranded
           (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:34:

GCAGACTTTG GACTAGCCAG ATTCGGTATT CCGGTCAAC                           39

(2) INFORMATION FOR SEQ ID NO:35:

(i) SEQUENCE CHARACTERISTICS:
           (A) LENGTH: 24
           (B) TYPE: amino acid
           (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:35:

Ile Lys Leu Ala Asp Phe Gly Leu Ala Arg Ala Phe Gly Val Pro Val
1               5                   10                  15

Arg Thr Tyr Thr His Glu Val Val
            20

(2) INFORMATION FOR SEQ ID NO:36:

(i) SEQUENCE CHARACTERISTICS:
           (A) LENGTH: 24
           (B) TYPE: amino acid
           (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:36:

Leu Lys Leu Gly Asp Phe Gly Leu Ala Arg Ala Phe Gly Ile Pro Val
1               5                   10                  15

Asn Thr Phe Ser Ser Glu Val Val
            20

(2) INFORMATION FOR SEQ ID NO:37:

(i) SEQUENCE CHARACTERISTICS:
           (A) LENGTH: 19
           (B) TYPE: amino acid
           (D) TOPOLOGY: linear

```
        (ii) MOLECULE TYPE: peptide (iii) HYPOTHETICAL: NO (iv) ANTI-SENSE: NO (xi) SEQUENCE DESCRIPTION: SEQ ID NO:37:

Ile Lys Leu Ala Asp Phe Gly Leu Ala Arg Ala Phe Gly Ile Pro Val
1               5                  10                  15

Asn Thr Phe (2) INFORMATION FOR SEQ ID NO:38:

(i) SEQUENCE CHARACTERISTICS:
             (A) LENGTH: 10
             (B) TYPE: amino acid
             (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:38:

Lys Val Val Pro Pro Leu Asp Gly Glu Arg
1               5                  10

(2) INFORMATION FOR SEQ ID NO:39:

(i) SEQUENCE CHARACTERISTICS:
             (A) LENGTH: 11
             (B) TYPE: amino acid
             (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:39:

Gln Gln Arg Pro Pro Arg Asp Leu Arg Gln Val
1               5                  10

(2) INFORMATION FOR SEQ ID NO:40:

(i) SEQUENCE CHARACTERISTICS:
             (A) LENGTH: 9
             (B) TYPE: amino acid
             (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:40:

Gln Gln Arg Pro Pro Asp Gly Glu Arg
1               5

(2) INFORMATION FOR SEQ ID NO:41:

(i) SEQUENCE CHARACTERISTICS:
             (A) LENGTH: 47
             (B) TYPE: nucleic acid
             (C) STRANDEDNESS: single stranded
             (D) TOPOLOGY: linear
```

(ii) MOLECULE TYPE: DNA (iii) HYPOTHETICAL: NO (iv) ANTI-SENSE: NO (xi) SEQUENCE DESCRIPTION: SEQ ID NO:41:

GATCCTACTC GAGATACTAG TTTGTTTATT TATGTGTGTT TATTCGA                47

(2) INFORMATION FOR SEQ ID NO:42:

(i) SEQUENCE CHARACTERISTICS:
        (A) LENGTH: 30
        (B) TYPE: nucleic acid
        (C) STRANDEDNESS: single stranded
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:42:

CGCGGTACCC AATACAAACA AGGCCTCTCC                                   30

(2) INFORMATION FOR SEQ ID NO:43:

(i) SEQUENCE CHARACTERISTICS:
        (A) LENGTH: 37
        (B) TYPE: nucleic acid
        (C) STRANDEDNESS: single stranded
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:43:

AGATCTCGAC TCTAGAGGCC TCGGGCATTT TTGTCTA                           37

(2) INFORMATION FOR SEQ ID NO:44:

(i) SEQUENCE CHARACTERISTICS:
        (A) LENGTH: 43
        (B) TYPE: nucleic acid
        (C) STRANDEDNESS: single stranded
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:44:

GAGGCCTCTA GAGTCGAGAT CTAAGAACGG TAAACTCTCC AAG                    43

(2) INFORMATION FOR SEQ ID NO:45:

(i) SEQUENCE CHARACTERISTICS:
        (A) LENGTH: 31
        (B) TYPE: nucleic acid
        (C) STRANDEDNESS: single stranded
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:45:

CGGCAAGCTT GTACCGATGA GATAACCTAG G         31

(2) INFORMATION FOR SEQ ID NO:46:

(i) SEQUENCE CHARACTERISTICS:
            (A) LENGTH: 31
            (B) TYPE: nucleic acid
            (C) STRANDEDNESS: single stranded
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:46:

CGCGGTACCC AGACGCATAC CCTAAATGGA G         31

(2) INFORMATION FOR SEQ ID NO:47:

(i) SEQUENCE CHARACTERISTICS:
            (A) LENGTH: 40
            (B) TYPE: nucleic acid
            (C) STRANDEDNESS: single stranded
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:47:

AGATCTCGAC TCTAGATTCT TAGGTGTCAA GCCTCGCATC         40

(2) INFORMATION FOR SEQ ID NO:48:

(i) SEQUENCE CHARACTERISTICS:
            (A) LENGTH: 51
            (B) TYPE: nucleic acid
            (C) STRANDEDNESS: single stranded
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:48:

ACCTAAGAAT CTAGAGTCGA GATCTCTGTG GAGCGACGTT TATCCAGATA G         51

(2) INFORMATION FOR SEQ ID NO:49:

(i) SEQUENCE CHARACTERISTICS:
            (A) LENGTH: 32
            (B) TYPE: nucleic acid
            (C) STRANDEDNESS: single stranded
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:49:

CGCAAGCTTA GATTGTGGCG CCTTTACTGG TG                                              32

(2) INFORMATION FOR SEQ ID NO:50:

(i) SEQUENCE CHARACTERISTICS:
        (A) LENGTH: 29
        (B) TYPE: nucleic acid
        (C) STRANDEDNESS: single stranded
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:50:

GCGCACTAGT AGAATGGCTA CCTCTCGAT                                                  29

(2) INFORMATION FOR SEQ ID NO:51:

(i) SEQUENCE CHARACTERISTICS:
        (A) LENGTH: 18
        (B) TYPE: nucleic acid
        (C) STRANDEDNESS: single stranded
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:51:

TCTGGCCAGG CCAAAGTC                                                              18

(2) INFORMATION FOR SEQ ID NO:52:

(i) SEQUENCE CHARACTERISTICS:
        (A) LENGTH: 36
        (B) TYPE: nucleic acid
        (C) STRANDEDNESS: single stranded
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:52:

GACTTTGGCC TGGCCAGAGC TTTCGGTATT CCGGTC                                          36

(2) INFORMATION FOR SEQ ID NO:53:

(i) SEQUENCE CHARACTERISTICS:
        (A) LENGTH: 31
        (B) TYPE: nucleic acid
        (C) STRANDEDNESS: single stranded
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:53:

```
GCGCACTAGT ATGGCTTTCG GTATTCCGGT C                                      31

(2) INFORMATION FOR SEQ ID NO:54:

(i) SEQUENCE CHARACTERISTICS:
        (A) LENGTH: 34
        (B) TYPE: nucleic acid
        (C) STRANDEDNESS: single stranded
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:54:

GCGCGGATCC TTATAGGTCT CTTGGTGGTC GTTG                                   34

(2) INFORMATION FOR SEQ ID NO:55:

(i) SEQUENCE CHARACTERISTICS:
        (A) LENGTH: 30
        (B) TYPE: nucleic acid
        (C) STRANDEDNESS: single stranded
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:55:

GCGCACTAGT AAAAATCAAC CTCGAGCTCT                                        30

(2) INFORMATION FOR SEQ ID NO:56:

(i) SEQUENCE CHARACTERISTICS:
        (A) LENGTH: 34
        (B) TYPE: nucleic acid
        (C) STRANDEDNESS: single stranded
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:56:

GCGCGGATCC TTATCAACGG GCCAGACCGA AATC                                   34

(2) INFORMATION FOR SEQ ID NO:57:

(i) SEQUENCE CHARACTERISTICS:
        (A) LENGTH: 37
        (B) TYPE: nucleic acid
        (C) STRANDEDNESS: single stranded
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:57:

GCGCGGATCC TTATCAAGCT CTGGCTAGTC CAAAGTC                                37
```